(12) United States Patent
Rajgarhia et al.

(10) Patent No.: US 7,109,010 B2
(45) Date of Patent: Sep. 19, 2006

(54) METHODS AND MATERIALS FOR THE SYNTHESIS OF ORGANIC PRODUCTS

(75) Inventors: Vineet Rajgarhia, Hopkins, MN (US); Merja Penttilä, Helsinki (FI); Laura Ruohonen, Helsinki (FI); Marja Ilmén, Helsinki (FI); Kari Koivuranta, Helsinki (FI)

(73) Assignee: Nature Works LLC, Minneapolis, MN (US)

( * ) Notice: Subject to any disclaimer, the term of this patent is extended or adjusted under 35 U.S.C. 154(b) by 0 days.

(21) Appl. No.: 09/992,430

(22) Filed: Nov. 23, 2001

(65) Prior Publication Data

US 2003/0166179 A1    Sep. 4, 2003

Related U.S. Application Data

(60) Provisional application No. 60/252,541, filed on Nov. 22, 2000.

(51) Int. Cl.
  *C12N 9/04* (2006.01)
  *C12N 1/20* (2006.01)
  *C12N 15/00* (2006.01)
  *C12Q 1/68* (2006.01)
  *C70H 21/04* (2006.01)

(52) U.S. Cl. ............... 435/190; 435/4; 435/6; 435/252.3; 435/320.1; 435/69.1; 435/71.1; 435/440; 536/23.2; 536/23.74

(58) Field of Classification Search ............. 435/189, 435/252.3, 320.1, 71.1, 190, 440, 6, 69.1, 435/4; 536/23.2, 23.74
See application file for complete search history.

(56) References Cited

U.S. PATENT DOCUMENTS

| | | | |
|---|---|---|---|
| 4,275,234 A | 6/1981 | Baniel et al. | |
| 4,683,195 A | 7/1987 | Mullis et al. | |
| 4,859,596 A | 8/1989 | Hollenberg et al. | |
| 4,943,529 A | 7/1990 | Van den Berg et al. | |
| 5,510,526 A | 4/1996 | Baniel et al. | |
| 5,641,406 A | 6/1997 | Sarhaddar et al. | |
| 5,831,122 A | 11/1998 | Eyal | |
| 6,485,947 B1 * | 11/2002 | Rajgarhia et al. ......... 435/139 | |

FOREIGN PATENT DOCUMENTS

WO    WO 93/00440 A1    1/1993

OTHER PUBLICATIONS

Backer et al. "Transformation of Candida Albicans by Electroporation", 1999, *Yeast 15*: 1609-1618.
Becker and Guarente, "High-Efficiency Transformation of Yeast by Electroporation" *Methods in Enzymology* 194:182-187 (1991).
Chen et al., "Sequence Organization of the Circular Plasmid pKD1 from the yeast Kluyveromyces drosophilarum", 1986, *Nucleic Acids Res.* 14: 4471-4481.
Chien et al. "The two-hybrid system: A method to identify and clone genes for proteins that interact with a protein of interest", (*Proc. Natl Acad. Sci.*, 88:9578-9582 (1991).

(Continued)

*Primary Examiner*—Manjunath Rao
*Assistant Examiner*—Yong Pak
(74) *Attorney, Agent, or Firm*—McDonnell Boehnen Hulbert & Berghoff

(57) ABSTRACT

This invention provides biocatalysts that are recombinant yeast cells comprising recombinant expression vectors encoding heterologous lactate dehydrogenase genes for producing lactate.

19 Claims, 27 Drawing Sheets

OTHER PUBLICATIONS

Datta et al., "Technological and economic potential of poly (lactic acid) and lactic acid derivatives", 1995, *FEMS Microbiol. Rev.* 16: 221-231.

Durrens et al., "Expression of the avian gag-myc oncogene in *Saccharomyces cerevisiae*", *Curr Genet.* 18:7-12 (1990).

Franzblau & Sinclair, "Induction of fermentation in Crabtree-Negative Yeasts", 1983, *Mycopathologia* 82: 185-190.

Gellissen and Hollenberg,"Application of yeast in gene expression studies: a comparison of *Saccharomyces cerevisiae*, Hansenula polymoroha and Kluyveromyces lactis- a review", Gene, 19-:87-97.

Gietz et al., "Improved Method for High Efficiency Transformation of Intact Yeast Cells". 1992, *Nucleic Acids Res.* 20:1425.

Gunge and Kitada, *Eur. J. Epidemiol.*, 4:409-414 (1988.

Holdsworth et al. "Enzyme Activities in Oleoginous Yeasts Accumulating and Utilizing Exogenous or Endogenous Lipids", *J. Gen. Microbiol.*, 134:2907-2915(1998).

Hwang et al., "Characterization of the transcription activation function and the DNA binding domain of transcriptional enhancer factor-1" 1993, *EMBO J.*12: 2337-2348.

Kelly et al., "Affinity Chromatography of Bacterial Lactate dehydrogenases" Biochem J., 171:543-7.

Kiers et al., "Regulation of Alcoholic Fermentation in Batch and Chemostat Cultures of Kluyveromyces lactis CBX 2359" *Yeast*, 14, 459-469 (1998).

Kurtzman and Fell, (1998) "*The Yeasts, A Taxonomic Study*" pp. 240-241.

Mach et al. "Transformation of Trichoderma reesei based on Hygromycin B resistance using, homologous expression signals", 1994, *Curr. Genet.* 25, 567-570.

Bunch et al., "The IdhA gene encoding the fermentative lactate Dehydrogenase of *Escherichia coli*", *Microbiology*, 143:187-95.

Morsomme et al. "Single point mutation in various domains of a plant plasma membrane H+-ATPase Expressed in *Saccharomyces cerevisie* increase H+-pumping and permit growth at low pH", (*EMBO J.* 15:5513-5526 1996.

Postma et al., "Enzymic Analysis of the Crabtree Effect in Glucose-Limited Chemostat Cultures of *Saccharomyces cerevisiae*", *Appl Environ. Microbiol.* 53, 468-477 (1989).

Subden et al. "An L-lactic acid dehydrogenase based method for detecting microbial colonies performing a malo-lactic fermentation", (*Canadian J. Microbiol.*, 28:883-886 (1982).

Thomas et al., "Biocatalysis:applications and potentials for the chemical industry", 2002, *Trends Biotechnol.* 20: 238-42.

Turakainen et al., "Consideration of the Evolution of the *Saccharomyces cerevisiae* MEL Gene Family on the Basis of the Nucleotide Sequences of the Genes and Their Flanking Regions", 1994, *Yeast 10*: 1559-1568.

Ullhrich, "Yeast Pyruvate Decarboxylase (2-Oxoacid Carboxylyase, EC 4.1.1.1) Assay of Thiamine Pyrophosphate" *Methods in Enzymology* 18:109-115 (1970).

Vickroy, "Lactid Acid", 1985, *Comprehensive Biotechnology*, (Moo-Young, ed.), vol. 3, Chapter 38 Pergamon Press, Oxford.

Wesolowski-Louvel et al. "Kluyveromyces lactis", (Nonconventional Yeasts in Biotechnology: *Kluyveromyces Lactis*, ed. Klaus Wolf, Springer Verlag, Berlin, p. 138-201 (1996).

Danner et al., "Biotechnological Prodcution of Acrylic Acid from Biomass" Applied Biochemistry and Biotechnology 70-72:887-94 (1998).

Ito et al., "Transformation of Intact Yeast Cells Treated with Alkali Cations" Journal of Bacteriology 153(1)163-168 (1983).

Naumov et al., "A new family of polymorphic genes in *Saccharomyces cervisiae*:α-galactosidase genes MEL1-MEL7" Mol. Gen. Genet 224:119-128 (1990).

Witte et al., "Characterization of yeasts with high L[+]-lactic acid production: Lactic acid specific soft-agar overlay (LASSO) and TAFE-patterns" J. Basic Microbiol 29(10)707-716 (1989).

Danner et al., "Bacillus stearothermophilus for Thermophilic Production of L-Lactic Acid" Applied Biochemistry and Biotechnology 70-72:895-903 (1998).

Gunge et al., "Isolation and Characterization of Linear Deoxyribonucleic Acid Plasmids from Kluyveromyces lactis and the Plasmid-Associated Killer Character" Jour. of Bacteriology 145(1)382-90 (1981).

* cited by examiner

SEQUENCE LISTING

<160> NUMBER OF SEQ ID NOS: 65

<210> SEQ ID NO 1
<211> LENGTH: 92
<212> TYPE: DNA
<213> ORGANISM: artificial sequence
<220> FEATURE:
<223> OTHER INFORMATION: multiple cloning site
<220> FEATURE:
<221> NAME/KEY: misc_feature
<223> OTHER INFORMATION: multiple cloning site

<400> SEQUENCE: 1
cccaagcttg aattccccgg gggatccctg cagggtacca cgcgtagatc tactagtgcg    60
gccgcctcga gtctagaggg cccaagcttg gg                                  92

<210> SEQ ID NO 2
<211> LENGTH: 91
<212> TYPE: DNA
<213> ORGANISM: artificial sequence
<220> FEATURE:
<223> OTHER INFORMATION: multiple cloning site
<220> FEATURE:
<221> NAME/KEY: misc_feature
<223> OTHER INFORMATION: multiple cloning site

<400> SEQUENCE: 2
ccaagcttgg gccctctaga ctcgaggcgg ccgcactagt agatctacgc gtggtaccct    60
gcagggatcc cccggggaat tcaagcttgg g                                   91

<210> SEQ ID NO 3
<211> LENGTH: 31
<212> TYPE: DNA
<213> ORGANISM: Lactobacillus helveticus

<400> SEQUENCE: 3
ccgggatcca tggcaagaga ggaaaaacct c                                   31

<210> SEQ ID NO 4
<211> LENGTH: 32
<212> TYPE: DNA
<213> ORGANISM: Lactobacillus helveticus

<400> SEQUENCE: 4
ccaagatctt tattgacgaa ccttaacgcc ag                                  32

<210> SEQ ID NO 5
<211> LENGTH: 37
<212> TYPE: DNA
<213> ORGANISM: Pediococcus acidilactici

<400> SEQUENCE: 5
ccgggatcca tgtctaatat tcaaaatcat caaaaag                             37

<210> SEQ ID NO 6
<211> LENGTH: 33
<212> TYPE: DNA
<213> ORGANISM: Pediococcus acidilactici

<400> SEQUENCE: 6
ccaagatctt tatttgtctt gttttcagc aag                                  33

<210> SEQ ID NO 7
<211> LENGTH: 82
<212> TYPE: DNA
<213> ORGANISM: Kluyveromyces marxianus

<400> SEQUENCE: 7

```
taaacagtac aatcgcaaag aaaagctcca cacccaaacc aaataattgc aatgcaactt    60
cttttctttt tttttctttt ct                                            82
```

<210> SEQ ID NO 8
<211> LENGTH: 79
<212> TYPE: DNA
<213> ORGANISM: Kluyveromyces marxianus

<400> SEQUENCE: 8

```
ttataaaatc attaaaatcc aaaatcgtaa tttatctctt tatcctctcc ctctctacat    60
gccggtagag gtgtggtca                                                79
```

<210> SEQ ID NO 9
<211> LENGTH: 1736
<212> TYPE: DNA
<213> ORGANISM: kanamycin resistance gene

<400> SEQUENCE: 9

```
gtacaacttg agcaagttgt cgatcagctc ctcaaattgg tcctctgtaa cggatgactc    60
aacttgcaca ttaacttgaa gctcagtcga ttgagtgaac ttgatcaggt tgtgcagctg   120
gtcagcagca tagggaaaca cggcttttcc taccaaactc aaggaattat caaactctgc   180
aacacttgcg tatgcaggta gcaagggaaa tgtcatactt gaagtcggac agtgagtgta   240
gtcttgagaa attctgaagc cgtatttttta ttatcagtga gtcagtcatc aggagatcct   300
ctacgccgga cgcatcgtgg ccgacctgca gggggggggg gggcgctgag gtctgcctcg   360
tgaagaaggt gttgctgact cataccaggc ctgaatcgcc ccatcatcca gccagaaagt   420
gagggagcca cggttgatga gagctttgtt gtaggtggac cagttggtga ttttgaactt   480
ttgctttgcc acggaacggt ctgcgttgtc gggaagatgc gtgatctgat ccttcaactc   540
agcaaaagtt cgatttattc aacaaagccg ccgtcccgtc aagtcagcgt aatgctctgc   600
cagtgttaca accaattaac caattctgat tagaaaaact catcgagcat caaatgaaac   660
tgcaatttat tcatatcagg attatcaata ccatattttt gaaaaagccg tttctgtaat   720
gaaggagaaa actcaccgag gcagttccat aggatggcaa gatcctggta tcggtctgcg   780
attccgactc gtccaacatc aatacaacct ttaatttccc ctcgtcaaaa ataaggttat   840
caagtgagaa atcaccatga gtgacgactg aatccggtga gaatggcaaa agcttatgca   900
ttctttccag acttgttcaa caggccagcc attacgctcg tcatcaaaat cactcgcatc   960
aaccaaaccg ttattcattc gtgattgcgc ctgagcgaga cgaaatacgc gatcgctgtt  1020
aaaaggacaa ttacaaacag gaatcgaatg caaccggcgc aggaacactg ccagcgcatc  1080 aacaatatttt tcacctgaat caggatattc ttctaatacc tggaatgctg ttttcccggg  1140
gatcgcagtg gtgagtaacc atgcatcatc aggagtacgg ataaaatgct tgatggtcgg  1200
aagaggcata aattccgtca gccagtttag tctgaccatc tcatctgtaa catcattggc  1260
aacgctacct ttgccatgtt tcagaaacaa ctctggcgca tcgggcttcc catacaatcg  1320
atagattgtc gcacctgatt gcccgacatt atcgcgagcc catttatacc catataaatc  1380
agcatccatg ttggaattta atcgcggcct cgagcaagac gtttcccgtt gaatatggct  1440
```

-continued

| | |
|---|---|
| cataacaccc cttgtattac tgtttatgta agcagacagt tttattgttc atgatgatat | 1500 |
| atttttatct tgtgcaatgt aacatcagag attttgagac acaacgtggc tttccccccc | 1560 |
| cccctgcag gtcggcatca ccggcgccac aggtgcggtt gctggcgcct atatcgccga | 1620 |
| catcaccgat ggggaagatc gggctcgcca cttcgggctc atgagcgctt gtttcggcgt | 1680 |
| gggtatggtg gcaggccccg tggccggggg actgttgggc gccatctcct tgcatg | 1736 |

<210> SEQ ID NO 10
<211> LENGTH: 372
<212> TYPE: DNA
<213> ORGANISM: Kluyveromyces marxianus

<400> SEQUENCE: 10

| | |
|---|---|
| ccggttcttt ctcttactct tacaagacca agaacattgt cgaattccac tccgactaca | 60 |
| tcaaggtcag aaacgccact ttcccaggtg tccaaatgaa gttcgtcttg caaaagttgt | 120 |
| tgaccaaggt caaggatgct gctaagggtt acaagccagt tccagttcct cacgctccaa | 180 |
| gagacaacaa gccagttgct gactctactc cattgaagca agaatgggtc tggactcaag | 240 |
| tcggtaagtt cctacaagaa ggtgatgttg ttctaactga aaccggtacc tccgctttcg | 300 |
| gtatcaacca aacccacttc ccaaatgaca cctacggtat ctcccaagtc ttgtggggtt | 360 |
| ccattggttt ca | 372 |

<210> SEQ ID NO 11
<211> LENGTH: 747
<212> TYPE: DNA
<213> ORGANISM: Kluyveromyces thermotolerans

<400> SEQUENCE: 11

| | |
|---|---|
| ttaccactgt cttcggtctg ccaggtgact tcaatctgcg tctgttggac gagatctacg | 60 |
| aggtcgaggg tatgagatgg gccggtaact gtaacgagtt gaacgcttct tacgctgccg | 120 |
| acgcttacgc cagaatcaag ggtatgtcct gtttgatcac caccttcggt gtcggtgagt | 180 |
| tgtccgcttt gaacggtatc gccggttctt acgctgagca cgtcggtgtc ttgcacattg | 240 |
| tcggtgtccc atccgtctcc gcccaggcca agcagctatt gttgcaccac accttgggta | 300 |
| acggtgactt cactgtcttc cacagaatgt ccgccaacat ctctgagacc actgctatga | 360 |
| tcactgatct agctaccgcc ccatctgaga tcgacagatg tatcagaacc acctacatta | 420 |
| gacagagacc tgtctacttg ggtttgccat ctaacttcgt tgaccagatg gtcccagcct | 480 |
| ctctattgga cacccccaatt gacttggcct tgaagccaaa cgaccagcag gctgaggagg | 540 |
| aggtcatctc tactttgttg gagatgatca aggacgctaa gaacccagtc atcttggctg | 600 |
| acgcttgcgc ttccagacac gatgtcaagg ctgagaccaa gaagttgatt gacatcactc | 660 |
| agttcccatc tttcgttacc ccaatgggta agggttccat tgacgagaag cacccaagat | 720 |
| tcggtggtgt ctacgtcggt accttgt | 747 |

<210> SEQ ID NO 12
<211> LENGTH: 1738
<212> TYPE: DNA
<213> ORGANISM: kanalycin resistance gene fragment

<400> SEQUENCE: 12

| | |
|---|---|
| gtacaacttg agcaagttgt cgatcagctc ctcaaattgg tcctctgtaa cggatgactc | 60 |
| aacttgcaca ttaacttgaa gctcagtcga ttgagtgaac ttgatcaggt tgtgcagctg | 120 |
| gtcagcagca tagggaaaca cggcttttcc taccaaactc aaggaattat caaactctgc | 180 |

```
aacacttgcg tatgcaggta gcaagggaaa tgtcatactt gaagtcggac agtgagtgta      240
gtcttgagaa attctgaagc cgtattttta ttatcagtga gtcagtcatc aggagatcct      300
ctacgccgga cgcatcgtgg ccgacctgca gggggggggg gggcgctgag gtctgcctcg      360
tgaagaaggt gttgctgact cataccaggc ctgaatcgcc ccatcatcca gccagaaagt      420
gagggagcca cggttgatga gagctttgtt gtaggtggac cagttggtga ttttgaactt      480
ttgctttgcc acggaacggt ctgcgttgtc gggaagatgc gtgatctgat ccttcaactc      540
agcaaaagtt cgatttattc aacaaagccg ccgtcccgtc aagtcagcgt aatgctctgc      600
cagtgttaca accaattaac caattctgat tagaaaaact catcgagcat caaatgaaac      660
tgcaatttat tcatatcagg attatcaata ccatattttt gaaaaagccg tttctgtaat      720
gaaggagaaa actcaccgag gcagttccat aggatggcaa gatcctggta tcggtctgcg      780
attccgactc gtccaacatc aatacaacct attaatttcc cctcgtcaaa ataaggtta       840 tcaagtgaga aatcaccatg agtgacgact gaatccggtg agaatggcaa aagcttatgc      900
atttctttcc agacttgttc aacaggccag ccattacgct cgtcatcaaa atcactcgca      960
tcaaccaaac cgttattcat tcgtgattgc gcctgagcga gacgaaatac gcgatcgctg     1020
ttaaaaggac aattacaaac aggaatcgaa tgcaaccggc gcaggaacac tgccagcgca     1080
tcaacaatat tttcacctga atcaggatat tcttctaata cctggaatgc tgttttcccg     1140
gggatcgcag tggtgagtaa ccatgcatca tcaggagtac ggataaaatg cttgatggtc     1200
ggaagaggca taaattccgt cagccagttt agtctgacca tctcatctgt aacatcattg     1260
gcaacgctac ctttgccatg tttcagaaac aactctggcg catcgggctt cccatacaat     1320
cgatagattg tcgcacctga ttgcccgaca ttatcgcgag cccatttata cccatataaa     1380
tcagcatcca tgttggaatt taatcgcggc ctcgagcaag acgtttcccg ttgaatatgg     1440
ctcataaaac cccttgtatt actgtttatg taagcagaca gttttattgt tcatgatgat     1500 atattttat cttgtgcaat gtaacatcag agattttgag acacaacgtg gctttccccc       1560 cccccctgc aggtcggcat caccggcgcc acaggtgcgg ttgctggcgc ctatatcgcc        1620
gacatcaccg atggggaaga tcgggctcgc cacttcgggc tcatgagcgc ttgtttcggc      1680
gtgggtatgg tggcaggccc cgtggccggg ggactgttgg gcgccatctc cttgcatg       1738
```

<210> SEQ ID NO 13
<211> LENGTH: 17
<212> TYPE: DNA
<213> ORGANISM: artificial sequence
<220> FEATURE:
<223> OTHER INFORMATION: degenerate amplification primer
<220> FEATURE:
<221> NAME/KEY: misc_feature
<222> LOCATION: (1)..(17)
<223> OTHER INFORMATION: degenerate amplification primers

<400> SEQUENCE: 13
gtbatyggyt chggtac                                                      17

<210> SEQ ID NO 14
<211> LENGTH: 17
<212> TYPE: DNA
<213> ORGANISM: artificial sequence
<220> FEATURE:
<223> OTHER INFORMATION: degenerate amplification primer
<220> FEATURE:
<221> NAME/KEY: misc_feature
<222> LOCATION: (1)..(17)

```
<223> OTHER INFORMATION: degenerate amplification primers

<400> SEQUENCE: 14
swrtcdccrt gytcacc                                                    17

<210> SEQ ID NO 15
<211> LENGTH: 22
<212> TYPE: DNA
<213> ORGANISM: artificial sequence
<220> FEATURE:
<223> OTHER INFORMATION: amplification primer
<220> FEATURE:
<221> NAME/KEY: misc_feature
<222> LOCATION: (1)..(22)
<223> OTHER INFORMATION: amplification primer

<400> SEQUENCE: 15
gtacagttct ggatactgct cg                                              22

<210> SEQ ID NO 16
<211> LENGTH: 18
<212> TYPE: DNA
<213> ORGANISM: artificial sequence
<220> FEATURE:
<223> OTHER INFORMATION: amplification primer
<220> FEATURE:
<221> NAME/KEY: misc_feature
<222> LOCATION: (1)..(18)
<223> OTHER INFORMATION: amplification primers

<400> SEQUENCE: 16
acaggcatcg atgctgtc                                                   18

<210> SEQ ID NO 17
<211> LENGTH: 19
<212> TYPE: DNA
<213> ORGANISM: Kluyveromyces thermotolerans

<400> SEQUENCE: 17
gtgatgtcgg cgatatagg                                                  19

<210> SEQ ID NO 18
<211> LENGTH: 21
<212> TYPE: DNA
<213> ORGANISM: Kluyveromyces thermotolerans

<400> SEQUENCE: 18
ctacttggag ccactatcga c                                               21

<210> SEQ ID NO 19
<211> LENGTH: 21
<212> TYPE: DNA
<213> ORGANISM: Kluyveromyces thermotolerans

<400> SEQUENCE: 19
gatctcctgc taagctcttg c                                               21

<210> SEQ ID NO 20
<211> LENGTH: 20
<212> TYPE: DNA
<213> ORGANISM: Kluyveromyces thermotolerans

<400> SEQUENCE: 20
gcagttttgg atattcatgc                                                 20
```

<210> SEQ ID NO 21
<211> LENGTH: 972
<212> TYPE: DNA
<213> ORGANISM: Kluyveromyces thermotolerans

<400> SEQUENCE: 21

```
atgttccaag atacaaagtc tcaagcagta agaactgatg ccaaacagt  aaaagttgtg    60
gtagtgggag tgggaagtgt tgggtctgcc acagcgtata cgttgcttct cagcggcatc   120
gtttccgaga ttgtccttat cgacgtgaac aaagacaaag cagagggtga agcatggac    180
ttaaaccacg cagcaccttc aaatacaagg tctcgagcgg gtgattatcc tgactgcgct   240
ggcgcggcca ttgttattgt cacatgtggg attaaccaaa aaatggaca  aacaaggatg   300
gatcttgctg caaaaaatgc caacattatg ctggaaatca tccccaatgt tgccaaatat   360
gctcctgata ccatcctgct tattgccacg aatcctgtcg atgttttgac ctatattagc   420
tataaggcgt cagggtttcc actaagcaga gttatcggct caggtacagt tctggatact   480
gctcgtttta aatacatcct cggagagcac ttcaagatct catcggacag catcgatgcc   540
tgtgtaattg gagaacatgg tgattcgggt gtgcctgtct ggtctcttac caacatcgac   600
ggcatgaagc tccgggatta ctgcgaaaaa gccaaccaca tatttgatca gaatgcgttc   660
catagaatct ttgagcaaac gcgagacgct gcttacgata tcatcaagcg caaaggctat   720
acttcatatg gaatcgcagc gggattactt cgcatagtaa aggcgatttt agaggataca   780
ggatccacac ttacagtttc aaccgttggt gattattttg gggttgaaca aattgctata   840
agcgtcccta ccaaactcaa taaaagtggg gctcatcaag tggctgaact ttcactcgat   900
gagaaggaaa tagaattgat ggaaaaatca gctagtcaga tcaaatcagt gattgagcat   960
ctggagatca at                                                       972
```

<210> SEQ ID NO 22
<211> LENGTH: 323
<212> TYPE: PRT
<213> ORGANISM: Kluyveromyces thermotolerans

<400> SEQUENCE: 22

```
Met Phe Gln Asp Thr Lys Ser Gln Ala Val Arg Thr Asp Ala Lys Thr
1               5                   10                  15

Val Lys Val Val Val Gly Val Gly Ser Val Gly Ser Ala Thr Ala
            20                  25                  30

Tyr Thr Leu Leu Leu Ser Gly Ile Val Ser Glu Ile Val Leu Ile Asp
        35                  40                  45

Val Asn Lys Asp Lys Ala Glu Gly Glu Ser Met Asp Leu Asn His Ala
    50                  55                  60

Ala Pro Ser Asn Thr Arg Ser Arg Ala Gly Asp Tyr Pro Asp Cys Ala
65                  70                  75                  80

Gly Ala Ala Ile Val Ile Val Thr Cys Gly Ile Asn Gln Lys Asn Gly
                85                  90                  95

Gln Thr Arg Met Asp Leu Ala Ala Lys Asn Ala Asn Ile Met Leu Glu
            100                 105                 110

Ile Ile Pro Asn Val Ala Lys Tyr Ala Pro Asp Thr Ile Leu Leu Ile
        115                 120                 125

Ala Thr Asn Pro Val Asp Val Leu Thr Tyr Ile Ser Tyr Lys Ala Ser
    130                 135                 140

Gly Phe Pro Leu Ser Arg Val Ile Gly Ser Gly Thr Val Leu Asp Thr
145                 150                 155                 160
```

```
Ala Arg Phe Lys Tyr Ile Leu Gly Glu His Phe Lys Ile Ser Ser Asp
                165                 170                 175

Ser Ile Asp Ala Cys Val Ile Gly Glu His Gly Asp Gly Val Pro Val
            180                 185                 190

Trp Ser Leu Thr Asn Ile Asp Gly Met Lys Leu Arg Asp Tyr Cys Glu
                195                 200                 205

Lys Ala Asn His Ile Phe Asp Gln Asn Ala Phe His Arg Ile Phe Glu
            210                 215                 220

Gln Thr Arg Asp Ala Ala Tyr Asp Ile Ile Lys Arg Lys Gly Tyr Thr
225                 230                 235                 240

Ser Tyr Gly Ile Ala Ala Gly Leu Leu Arg Ile Val Lys Ala Ile Leu
                245                 250                 255

Glu Asp Thr Gly Ser Thr Leu Thr Val Ser Thr Val Gly Asp Tyr Phe
            260                 265                 270

Gly Val Glu Gln Ile Ala Ile Ser Val Pro Thr Lys Leu Asn Lys Ser
                275                 280                 285

Gly Ala His Gln Val Ala Glu Leu Ser Leu Asp Glu Lys Glu Ile Glu
            290                 295                 300

Leu Met Glu Lys Ser Ala Ser Gln Ile Lys Ser Val Ile Glu His Leu
305                 310                 315                 320

Glu Ile Asn

<210> SEQ ID NO 23
<211> LENGTH: 20
<212> TYPE: DNA
<213> ORGANISM: artificial sequence
<220> FEATURE:
<223> OTHER INFORMATION: degenerate amplification primer
<220> FEATURE:
<221> NAME/KEY: misc_feature
<223> OTHER INFORMATION: degenerate amplification primers

<400> SEQUENCE: 23
gtyggtgchg gtgchgthgg                                              20

<210> SEQ ID NO 24
<211> LENGTH: 17
<212> TYPE: DNA
<213> ORGANISM: artificial sequence
<220> FEATURE:
<223> OTHER INFORMATION: degenerate amplification primer
<220> FEATURE:
<221> NAME/KEY: misc_feature
<223> OTHER INFORMATION: degenerate amplification primers

<400> SEQUENCE: 24
swrtcdccrt gytcbcc                                                 17

<210> SEQ ID NO 25
<211> LENGTH: 27
<212> TYPE: DNA
<213> ORGANISM: artificial sequence
<220> FEATURE:
<223> OTHER INFORMATION: amplification primer
<220> FEATURE:
<221> NAME/KEY: misc_feature
<223> OTHER INFORMATION: amplification primers

<400> SEQUENCE: 25
atccacaaca gcttacacgt tattgag                                      27

<210> SEQ ID NO 26
```

-continued

```
<211> LENGTH: 28
<212> TYPE: DNA
<213> ORGANISM: artificial sequence
<220> FEATURE:
<223> OTHER INFORMATION: amplification primer
<220> FEATURE:
<221> NAME/KEY: misc_feature
<223> OTHER INFORMATION: amplification primers

<400> SEQUENCE: 26
gtttggttgc tggaagtggt gttgatag                                              28

<210> SEQ ID NO 27
<211> LENGTH: 27
<212> TYPE: DNA
<213> ORGANISM: artificial sequence
<220> FEATURE:
<223> OTHER INFORMATION: amplification primer
<220> FEATURE:
<221> NAME/KEY: misc_feature
<223> OTHER INFORMATION: amplification primers

<400> SEQUENCE: 27
aacattgaat agcttgctca ggttgtg                                               27

<210> SEQ ID NO 28
<211> LENGTH: 28
<212> TYPE: DNA
<213> ORGANISM: artificial sequence
<220> FEATURE:
<223> OTHER INFORMATION: amplification primer
<220> FEATURE:
<221> NAME/KEY: misc_feature
<223> OTHER INFORMATION: amplification primers

<400> SEQUENCE: 28
gataataaac gcgttgacat ttcagatg                                              28

<210> SEQ ID NO 29
<211> LENGTH: 939
<212> TYPE: DNA
<213> ORGANISM: Torulaspora pretoriensis
<220> FEATURE:
<221> NAME/KEY: CDS
<222> LOCATION: (1)..(939)
<223> OTHER INFORMATION:

<400> SEQUENCE: 29 atg cat aga tgt gct aaa gtg gcc atc gtc ggt gcc ggc caa gtt gga        48
Met His Arg Cys Ala Lys Val Ala Ile Val Gly Ala Gly Gln Val Gly
1               5                   10                  15 tcc aca aca gct tac acg tta tta ttg agt agt ttg gtt gct gaa gtg        96
Ser Thr Thr Ala Tyr Thr Leu Leu Leu Ser Ser Leu Val Ala Glu Val
                20                  25                  30 gtg ttg ata gat gtc gat aaa aga aag gtc gaa ggc caa ttt atg gat       144
Val Leu Ile Asp Val Asp Lys Arg Lys Val Glu Gly Gln Phe Met Asp
            35                  40                  45 ctg aac cac gcg gct cct tta acg aag gag tca cga ttc agt gct ggg       192
Leu Asn His Ala Ala Pro Leu Thr Lys Glu Ser Arg Phe Ser Ala Gly
        50                  55                  60 gac tat gaa agt tgt gct gat gct gcg gtt gta atc gta acg ggc ggg       240
Asp Tyr Glu Ser Cys Ala Asp Ala Ala Val Val Ile Val Thr Gly Gly
65                  70                  75                  80 gct aat cag aaa cct ggt caa act aga atg gag cta gcc gag agg aac       288
Ala Asn Gln Lys Pro Gly Gln Thr Arg Met Glu Leu Ala Glu Arg Asn
                85                  90                  95
```

| | | |
|---|---|---|
| gtt aaa atc atg cag gaa gtg atc cct aag att gtg aaa tac gcc ccc<br>Val Lys Ile Met Gln Glu Val Ile Pro Lys Ile Val Lys Tyr Ala Pro<br>100                          105                      110 | | 336 |
| aac gca att ttg ctg att gca aca aac cct gtc gat gta ctt acc tat<br>Asn Ala Ile Leu Leu Ile Ala Thr Asn Pro Val Asp Val Leu Thr Tyr<br>115                       120                      125 | | 384 |
| gct agt ttg aaa gcg tcg gga ttc cca gca agc cgg gtt att ggt tct<br>Ala Ser Leu Lys Ala Ser Gly Phe Pro Ala Ser Arg Val Ile Gly Ser<br>130                       135                      140 | | 432 |
| ggg aca gtt ctc gac tct gct cgt ata cag cac aac ctg agc aag cta<br>Gly Thr Val Leu Asp Ser Ala Arg Ile Gln His Asn Leu Ser Lys Leu<br>145                   150                      155                      160 | | 480 |
| ttc aat gtt tca tct gaa agt gtc aac gcg ttt att atc ggg gaa cat<br>Phe Asn Val Ser Ser Glu Ser Val Asn Ala Phe Ile Ile Gly Glu His<br>                         165                      170                      175 | | 528 |
| ggt gac tca agt gtg ccc gtc tgg tcg ctt gct gag att gcc ggc atg<br>Gly Asp Ser Ser Val Pro Val Trp Ser Leu Ala Glu Ile Ala Gly Met<br>                         180                      185                      190 | | 576 |
| aaa gtg gag gat tac tgt agg cag tcc aag aga aag ttt gac ccc agc<br>Lys Val Glu Asp Tyr Cys Arg Gln Ser Lys Arg Lys Phe Asp Pro Ser<br>                      195                      200                      205 | | 624 |
| att ctg acc aaa ata tat gag gag tcg cgt gac gcg gca gcc tac atc<br>Ile Leu Thr Lys Ile Tyr Glu Glu Ser Arg Asp Ala Ala Ala Tyr Ile<br>210                       215                      220 | | 672 |
| ata gaa cgc aaa ggc tat acc aat ttc ggg att gca gca ggt ttg gct<br>Ile Glu Arg Lys Gly Tyr Thr Asn Phe Gly Ile Ala Ala Gly Leu Ala<br>225                   230                      235                      240 | | 720 |
| agg ata gtg aga gct att ctg aga gat gaa ggt gcc cta tta act gtg<br>Arg Ile Val Arg Ala Ile Leu Arg Asp Glu Gly Ala Leu Leu Thr Val<br>                         245                      250                      255 | | 768 |
| tct act gta ggt gag cac ttt ggc atg aaa gat gtt tca ttg agt gtt<br>Ser Thr Val Gly Glu His Phe Gly Met Lys Asp Val Ser Leu Ser Val<br>                         260                      265                      270 | | 816 |
| cca act agg gta gac agg agc ggc gct cac cat gtc gtc gac ctt ctg<br>Pro Thr Arg Val Asp Arg Ser Gly Ala His His Val Val Asp Leu Leu<br>                      275                      280                      285 | | 864 |
| cta aac gac aag gag ctg gag caa att aaa aca tct gga gcc aag ata<br>Leu Asn Asp Lys Glu Leu Glu Gln Ile Lys Thr Ser Gly Ala Lys Ile<br>290                       295                      300 | | 912 |
| aag tca gcc tgt gat gaa ctt ggc att<br>Lys Ser Ala Cys Asp Glu Leu Gly Ile<br>305                      310 | | 939 |

<210> SEQ ID NO 30
<211> LENGTH: 313
<212> TYPE: PRT
<213> ORGANISM: Torulaspora pretoriensis

<400> SEQUENCE: 30

Met His Arg Cys Ala Lys Val Ala Ile Val Gly Ala Gly Gln Val Gly
1               5                   10                  15

Ser Thr Thr Ala Tyr Thr Leu Leu Ser Ser Leu Val Ala Glu Val
            20                  25                  30

Val Leu Ile Asp Val Asp Lys Arg Lys Val Glu Gly Gln Phe Met Asp
        35                  40                  45

Leu Asn His Ala Ala Pro Leu Thr Lys Glu Ser Arg Phe Ser Ala Gly
    50                  55                  60

Asp Tyr Glu Ser Cys Ala Asp Ala Ala Val Val Ile Val Thr Gly Gly
65                  70                  75                  80

-continued

```
Ala Asn Gln Lys Pro Gly Gln Thr Arg Met Glu Leu Ala Glu Arg Asn
            85                  90                  95

Val Lys Ile Met Gln Glu Val Ile Pro Lys Ile Val Lys Tyr Ala Pro
        100                 105                 110

Asn Ala Ile Leu Leu Ile Ala Thr Asn Pro Val Asp Val Leu Thr Tyr
            115                 120                 125

Ala Ser Leu Lys Ala Ser Gly Phe Pro Ala Ser Arg Val Ile Gly Ser
130                 135                 140

Gly Thr Val Leu Asp Ser Ala Arg Ile Gln His Asn Leu Ser Lys Leu
145                 150                 155                 160

Phe Asn Val Ser Ser Glu Ser Val Asn Ala Phe Ile Ile Gly Glu His
                165                 170                 175

Gly Asp Ser Ser Val Pro Val Trp Ser Leu Ala Glu Ile Ala Gly Met
            180                 185                 190

Lys Val Glu Asp Tyr Cys Arg Gln Ser Lys Arg Lys Phe Asp Pro Ser
        195                 200                 205

Ile Leu Thr Lys Ile Tyr Glu Glu Ser Arg Asp Ala Ala Tyr Ile
            210                 215                 220

Ile Glu Arg Lys Gly Tyr Thr Asn Phe Gly Ile Ala Ala Gly Leu Ala
225                 230                 235                 240

Arg Ile Val Arg Ala Ile Leu Arg Asp Glu Gly Ala Leu Leu Thr Val
                245                 250                 255

Ser Thr Val Gly Glu His Phe Gly Met Lys Asp Val Ser Leu Ser Val
            260                 265                 270

Pro Thr Arg Val Asp Arg Ser Gly Ala His His Val Val Asp Leu Leu
        275                 280                 285

Leu Asn Asp Lys Glu Leu Glu Gln Ile Lys Thr Ser Gly Ala Lys Ile
    290                 295                 300

Lys Ser Ala Cys Asp Glu Leu Gly Ile
305                 310
```

<210> SEQ ID NO 31
<211> LENGTH: 21
<212> TYPE: DNA
<213> ORGANISM: Bacillus megaterium

<400> SEQUENCE: 31
cctgagtcca cgtcattatt c                                         21

<210> SEQ ID NO 32
<211> LENGTH: 22
<212> TYPE: DNA
<213> ORGANISM: Bacillus megaterium

<400> SEQUENCE: 32
tgaagctatt tattcttgtt ac                                        22

<210> SEQ ID NO 33
<211> LENGTH: 27
<212> TYPE: DNA
<213> ORGANISM: Bacillus megaterium

<400> SEQUENCE: 33
gctctagatg aaaacacaat ttacacc                                   27

<210> SEQ ID NO 34
<211> LENGTH: 28
<212> TYPE: DNA

<213> ORGANISM: Bacillus megaterium

<400> SEQUENCE: 34
atggatcctt acacaaaagc tctgtcgc                                28

<210> SEQ ID NO 35
<211> LENGTH: 26
<212> TYPE: DNA
<213> ORGANISM: Rhizopus oryzae

<400> SEQUENCE: 35
ctttattttt ctttacaata taattc                                  26

<210> SEQ ID NO 36
<211> LENGTH: 19
<212> TYPE: DNA
<213> ORGANISM: Rhizopus oryzae

<400> SEQUENCE: 36
actagcagtg caaaacatg                                          19

<210> SEQ ID NO 37
<211> LENGTH: 29
<212> TYPE: DNA
<213> ORGANISM: Rhizopus oryzae

<400> SEQUENCE: 37
gctctagatg gtattacact caaaggtcg                               29

<210> SEQ ID NO 38
<211> LENGTH: 30
<212> TYPE: DNA
<213> ORGANISM: Rhizopus oryzae

<400> SEQUENCE: 38
gctctagatc aacagctact tttagaaaag                              30

<210> SEQ ID NO 39
<211> LENGTH: 28
<212> TYPE: DNA
<213> ORGANISM: artificial sequence
<220> FEATURE:
<223> OTHER INFORMATION: cloning site sequence

<400> SEQUENCE: 39
aaatctagat gagccatatt caacggga                                28

<210> SEQ ID NO 40
<211> LENGTH: 29
<212> TYPE: DNA
<213> ORGANISM: artificial sequence
<220> FEATURE:
<223> OTHER INFORMATION: cloning site sequence

<400> SEQUENCE: 40
ccggatcctt agaaaaactc atcgagcat                               29

<210> SEQ ID NO 41
<211> LENGTH: 36
<212> TYPE: DNA
<213> ORGANISM: Kluyveromyces thermotolerans

<400> SEQUENCE: 41
gctctagaat tatgttccaa gatacaaagt ctcaag                       36

<210> SEQ ID NO 42
<211> LENGTH: 34
<212> TYPE: DNA
<213> ORGANISM: Kluyveromyces thermotolerans

<400> SEQUENCE: 42

| | | | |
|---|---|---|---|
| ccggaattca tcctcaattg atctccagat gctc | | | 34 |

<210> SEQ ID NO 43
<211> LENGTH: 2229
<212> TYPE: DNA
<213> ORGANISM: Kluyveromyces thermotolerans

<400> SEQUENCE: 43

| | | | | | |
|---|---|---|---|---|---|
| gcggccgcgg | atcgctcttc | cgctatcgat | taattttttt | ttctttcctc | tttttattaa | 60 |
| ccttaatttt | tattttagat | tcctgacctt | caactcaaga | cgcacagata | ttataacatc | 120 |
| tgcacaatag | gcatttgcaa | gaattactcg | tgagtaagga | aagagtgagg | aactatcgca | 180 |
| tacctgcatt | taaagatgcc | gatttgggcg | cgaatccttt | attttggctt | caccctcata | 240 |
| ctattatcag | ggccagaaaa | aggaagtgtt | tccctccttc | ttgaattgat | gttaccctca | 300 |
| taaagcacgt | ggcctcttat | cgagaaagaa | attaccgtcg | ctcgtgattt | gttttgcaaaa | 360 |
| agaacaaaac | tgaaaaaacc | cagacacgct | cgacttcctg | tcttcctatt | gattgcagct | 420 |
| tccaatttcg | tcacacaaca | aggtcctagc | gacggctcac | aggttttgta | acaagcaatc | 480 |
| gaaggttctg | gaatggcggg | aaagggttta | gtaccacatg | ctatgatgcc | cactgtgatc | 540 |
| tccagagcaa | agttcgttcg | atcgtactgt | tactctctct | ctttcaaaca | gaattgtccg | 600 |
| aatcgtgtga | caacaacagc | ctgttctcac | acactctttt | cttctaacca | agggggtggt | 660 |
| ttagtttagt | agaacctcgt | gaaacttaca | tttacatata | tataaacttg | cataaattgg | 720 |
| tcaatgcaag | aaatacatat | ttggtctttt | ctaattcgta | gtttttcaag | ttcttagatg | 780 |
| cttctttttt | ctctttttta | cagatcatca | aggaagtaat | tatctacttt | ttacaacaaa | 840 |
| tctagaatta | tgttccaaga | tacaaagtct | caagcagtaa | gaactgatgc | caaaacagta | 900 |
| aaagttgtgg | tagtgggagt | gggaagtgtt | gggtctgcca | cagcgtatac | gttgcttctc | 960 |
| agcggcatcg | tttccgagat | tgtccttatc | gacgtgaaca | aagacaaagc | agagggtgaa | 1020 |
| agcatggact | taaaccacgc | agcaccttca | aatacaaggt | ctcgagcggg | tgattatcct | 1080 |
| gactgcgctg | cgcgcggcca | tgttattgtc | acatgtggga | ttaaccaaaa | aaatggacaa | 1140 |
| acaaggatgg | atcttgctgc | aaaaaatgcc | aacattatgc | tggaaatcat | ccccaatgtt | 1200 |
| gccaaatatg | ctcctgatac | catcctgctt | attgccacga | atcctgtcga | tgttttgacc | 1260 |
| tatattagct | ataaggcgtc | agggtttcca | ctaagcagag | ttatcggctc | aggtacagtt | 1320 |
| ctggatactg | ctcgttttaa | atacatcctc | ggagagcact | tcaagatctc | atcggacagc | 1380 |
| atcgatgcct | gtgtaattgg | agaacatggt | gattcgggtg | tgcctgtctg | gtctcttacc | 1440 |
| aacatcgacg | gcatgaagct | ccgggattac | tgcgaaaaag | ccaaccacat | atttgatcag | 1500 |
| aatgcgttcc | atagaatctt | tgagcaaacg | cgagacgctg | cttacgatat | catcaagcgc | 1560 |
| aaaggctata | cttcatatgg | aatcgcagcg | ggattacttc | gcatagtaaa | ggcgatttta | 1620 |
| gaggatacag | gatccacact | tacagtttca | accgttggtg | attattttgg | ggttgaacaa | 1680 |
| attgctataa | gcgtccctac | caaactcaat | aaaagtgggg | ctcatcaagt | ggctgaactt | 1740 |
| tcactcgatg | agaaggaaat | agaattgatg | gaaaaatcag | ctagtcagat | caaatcagtg | 1800 |

-continued

| | |
|---|---|
| attgagcatc tggagatcaa ttgaggatga attcggatcc ggtagataca ttgatgctat | 1860 |
| caatccagag aactggaaag attgtgtagc cttgaaaaac ggtgaaactt acgggtccaa | 1920 |
| gattgtctac agattttcct gatttgccag cttactatcc ttcttgaaaa tatgcactct | 1980 |
| atatctttta gttcttaatt gcaacacata gatttgctgt ataacgaatt ttatgctatt | 2040 |
| ttttaaattt ggagttcagt gataaaagtg tcacagcgaa tttcctcaca tgtagggacc | 2100 |
| gaattgttta caagttctct gtaccaccat ggagacatca aaaattgaaa atctatggaa | 2160 |
| agatatggac ggtagcaaca agaatatagc acgagccgcg gatttatttc gttacgcatg | 2220 |
| cgcggccgc | 2229 |

<210> SEQ ID NO 44
<211> LENGTH: 32
<212> TYPE: DNA
<213> ORGANISM: Candida sonorensis

<400> SEQUENCE: 44

| | |
|---|---|
| tggactagta aaccaacagg gattgcctta gt | 32 |

<210> SEQ ID NO 45
<211> LENGTH: 33
<212> TYPE: DNA
<213> ORGANISM: Candida sonorensis

<400> SEQUENCE: 45

| | |
|---|---|
| ctagtctaga gatcattacg ccagcatcct agg | 33 |

<210> SEQ ID NO 46
<211> LENGTH: 37
<212> TYPE: DNA
<213> ORGANISM: Candida albicans

<400> SEQUENCE: 46

| | |
|---|---|
| gcgatctcga ggtcctagaa tatgtatact aatttgc | 37 |

<210> SEQ ID NO 47
<211> LENGTH: 36
<212> TYPE: DNA
<213> ORGANISM: Candida albicans

<400> SEQUENCE: 47

| | |
|---|---|
| acttggccat ggtgatagtt attcttctgc aattga | 36 |

<210> SEQ ID NO 48
<211> LENGTH: 20
<212> TYPE: DNA
<213> ORGANISM: Saccharomyces cerevisiae

<400> SEQUENCE: 48

| | |
|---|---|
| tgtcatcact gctccatctt | 20 |

<210> SEQ ID NO 49
<211> LENGTH: 20
<212> TYPE: DNA
<213> ORGANISM: Saccharomyces cerevisiae

<400> SEQUENCE: 49

| | |
|---|---|
| ttaagccttg gcaacatatt | 20 |

<210> SEQ ID NO 50
<211> LENGTH: 37

```
<212> TYPE: DNA
<213> ORGANISM: Candida albicans

<400> SEQUENCE: 50
gcgatctcga ggtcctagaa tatgtatact aatttgc                                37

<210> SEQ ID NO 51
<211> LENGTH: 39
<212> TYPE: DNA
<213> ORGANISM: Candida albicans

<400> SEQUENCE: 51
cgcgaattcc catggttagt ttttgttgga aagagcaac                              39

<210> SEQ ID NO 52
<211> LENGTH: 32
<212> TYPE: DNA
<213> ORGANISM: Candida sonorensis

<400> SEQUENCE: 52
tggactagta aaccaacagg gattgcctta gt                                     32

<210> SEQ ID NO 53
<211> LENGTH: 33
<212> TYPE: DNA
<213> ORGANISM: Candida sonorensis

<400> SEQUENCE: 53
ctagtctaga gatcattacg ccagcatcct agg                                    33

<210> SEQ ID NO 54
<211> LENGTH: 44
<212> TYPE: DNA
<213> ORGANISM: Candida sonorensis

<400> SEQUENCE: 54
ccggaattcg atatctgggc wggkaatgcc aaygarttra atgc                        44

<210> SEQ ID NO 55
<211> LENGTH: 44
<212> TYPE: DNA
<213> ORGANISM: Candida sonorensis
<220> FEATURE:
<221> NAME/KEY: misc_feature
<222> LOCATION: (33)..(33)
<223> OTHER INFORMATION: primer that does not encode amino acid
<220> FEATURE:
<221> NAME/KEY: misc_feature
<222> LOCATION: (21)..(21)
<223> OTHER INFORMATION: primer that does not encode amino acid

<400> SEQUENCE: 55
cgcggattca ggcctcagta ngaraawgaa ccngtrttra artc                        44

<210> SEQ ID NO 56
<211> LENGTH: 10
<212> TYPE: PRT
<213> ORGANISM: Candida sonorensis

<400> SEQUENCE: 56

Trp Ala Gly Asn Ala Asn Glu Leu Asn Ala
 1               5                  10

<210> SEQ ID NO 57
<211> LENGTH: 10
```

```
<212> TYPE: PRT
<213> ORGANISM: Candida sonorensis

<400> SEQUENCE: 57

Asp Phe Asn Thr Gly Ser Phe Ser Tyr Ser
1               5                   10

<210> SEQ ID NO 58
<211> LENGTH: 18
<212> TYPE: DNA
<213> ORGANISM: Candida sonorensis

<400> SEQUENCE: 58
tctgttmcct acrtaaga                                                        18

<210> SEQ ID NO 59
<211> LENGTH: 20
<212> TYPE: DNA
<213> ORGANISM: Candida sonorensis

<400> SEQUENCE: 59
gtyggtggtc acgaaggtgc                                                      20

<210> SEQ ID NO 60
<211> LENGTH: 36
<212> TYPE: DNA
<213> ORGANISM: Candida sonorensis

<400> SEQUENCE: 60
gcgatctcga gaaagaaacg acccatccaa gtgatg                                    36

<210> SEQ ID NO 61
<211> LENGTH: 68
<212> TYPE: DNA
<213> ORGANISM: Candida sonorensis

<400> SEQUENCE: 61
tggactagta catgcatgcg gtgagaaagt agaaagcaaa cattgtatat agtcttttct          60
attattag                                                                   68

<210> SEQ ID NO 62
<211> LENGTH: 34
<212> TYPE: DNA
<213> ORGANISM: Candida sonorensis

<400> SEQUENCE: 62
gcgatctcga gaaaatgtta ttataacact acac                                      34

<210> SEQ ID NO 63
<211> LENGTH: 75
<212> TYPE: DNA
<213> ORGANISM: Candida sonorensis

<400> SEQUENCE: 63
tggactagta catgcatgcg gtgagaaagt agaaagcaaa catttgttt gatttgtttg           60 ttttgttttt gtttg                                                           75

<210> SEQ ID NO 64
<211> LENGTH: 36
<212> TYPE: DNA
<213> ORGANISM: Candida sonorensis

<400> SEQUENCE: 64
```

```
gcgatctcga gaaagaaacg acccatccaa gtgatg                                    36

<210> SEQ ID NO 65
<211> LENGTH: 35
<212> TYPE: DNA
<213> ORGANISM: Candida sonorensis

<400> SEQUENCE: 65
acttggccat ggtatatagt cttttctatt attag                                    35
```

METHODS AND MATERIALS FOR THE SYNTHESIS OF ORGANIC PRODUCTS

This application claims priority to U.S. Provisional Application Ser. No. 60/252,541, filed Nov. 22, 2000.

BACKGROUND OF THE INVENTION

1. Technical Field

The invention relates to methods and materials involved in the production of organic products.

2. Background Information

Organic products such as lactic acid have many important industrial uses. For example, organic acids can be used to synthesize plastic materials as well as other products. To meet the increasing need for organic products, more efficient and cost effective production methods are being developed. One such method involves the use of bacteria. Specifically, certain bacteria can produce large quantities of particular organic products under certain fermentation conditions. The use of living bacteria as factories, however, is limited by the inability of the bacteria to grow as the organic product accumulates in the growth media. To circumvent such limitations, various product purification techniques have been employed during product synthesis. In addition, the use of microorganisms other than bacteria has been attempted. In fact, *Saccharomyces cerevisiae*, which is known to be acid tolerant, has been genetically modified in an attempt to produce lactic acid. Specifically, *S. cerevisiae* cells were modified by providing the cells with a bovine lactate dehydrogenase cDNA and disrupting endogenous pyruvate decarboxylase genes (PDC1, PDC5, and PDC6). While these modified *S. cerevisiae* cells produced some lactic acid, cell growth was suppressed leading to the conclusion that both cell growth and lactic acid production need improvement.

SUMMARY OF THE INVENTION

The present invention relates generally to methods and materials for producing organic products. Specifically, the invention provides yeast cells, methods for culturing yeast cells, methods for making yeast cells, nucleic acid constructs, and methods and materials for producing various organic products. The invention is based on the discovery that particular microorganisms (e.g., bacterial and fungal microorganisms) can be genetically manipulated to have the ability, under specific culture conditions, to grow, utilize various carbon sources for growth as well as product production, and produce a desired organic product for commercial purposes. For example, the yeast cells provided herein can grow and produce an organic product when cultured at low pH and high temperature. Having the ability to grow rapidly and produce an organic product efficiently under, for example, low pH and high temperature conditions is particularly advantageous. Specifically, the ability of a microorganism to tolerate low pH obviates the need to maintain a neutral pH environment, which can be difficult and expensive during large-scale production processes. In addition, the methods and materials needed to recover the desired organic product from a low pH broth can be more practical and efficient than those required to recover the same organic product from a broth having a more neutral pH. For example, certain organic acid products can precipitate out of solution as the pH drops below the product's $pK_a$ value, making recovery quite simple. Further, the ability of a microorganism to tolerate high temperatures obviates the need to maintain cool temperatures during the growth and production phases. Clearly, reducing the need to lower the temperature in a large volume tank of broth during large-scale production processes makes the overall process more efficient and less expensive. Moreover, the ability of a microorganism to tolerate both low pH and high temperature provides a convenient method for preventing contamination by other less tolerant microorganisms during the large-scale production processes.

It is important to note that a critical aspect relating to the ability to produce a desired organic product for commercial purposes can be the specific productivity at which that desired organic product is produced. For example, providing a high specific productivity using the methods and materials as described herein can allow a microorganism to generate the energy needed for cell maintenance when exposed to culture conditions such as low pH and high temperature. This required energy can be generated via a fermentation pathway under substantially anaerobic conditions, rather than relying on the generation of energy via the respiratory pathway. Obtaining energy via a fermentation pathway is particularly advantageous when producing an organic product that does not require the respiratory pathway since essentially all of the provided carbon source can be used to produce the desired organic product.

The invention also is based on the discovery that the utilization of a carbon source by certain genetically manipulated microorganisms can be controlled and directed predominately towards the production of either biomass or a desired organic product. In general terms, the invention involves two types of culturing processes. One culturing process involves culturing microorganisms under specific culture conditions, depending on the microorganism and desired outcome, that promote biomass production, while the other involves a different set of culture conditions, also dependent upon the microorganism and desired outcome, that promotes the production of a desired organic product. Clearly, having the ability to manipulate the utilization of a carbon source during large-scale production processes provides manufacturers with greater flexibility and more control than is otherwise possible.

In addition, the invention is based on the discovery that certain microorganisms can be genetically manipulated such that most, if not all, of a carbon source is utilized for the production of either biomass or a desired organic product. Specifically, the invention provides yeast cells that are modified such that biosynthesis pathways that divert the utilization of a carbon source away from the production of biomass or the desired organic product are inactivated. Inactivating such biosynthesis pathways provides microorganisms that can efficiently grow and produce the desired product.

In general, the invention features a yeast cell containing an exogenous nucleic acid molecule, with the exogenous nucleic acid molecule encoding a polypeptide having enzymatic activity within the cell. The nucleic acid can be incorporated into the genome of the cell. The enzymatic activity leads to the formation of an organic product that, in some embodiments, is secreted from the cell. The cell further has a crabtree-negative phenotype and produces the organic product. The cell can be, for example, from the genus *Kluyveromyces, Pichia, Hansenula, Candida, Trichosporon,* or *Yamadazyma*. The organic product can be, for example, a fermentation product, a pyruvate-derived product, an organic acid, or a carboxylate such as lactate. In one embodiment, the polypeptide can have lactate dehydrogenase activity. For example, the exogenous nucleic acid can encode a bacterial lactate dehydrogenase or fungal lactate dehydrogenase such as a *K. lactis* fungal lactate dehydrogenase.

In another embodiment, the cell contains four exogenous nucleic acid molecules, each of the four exogenous nucleic acid molecules encoding a different polypeptide. For example, the first of the four exogenous nucleic acid molecules can encode a first polypeptide having lactate dehydrogenase activity, the second can encode a second polypeptide having CoA-transferase activity, the third can encode a third polypeptide having lactyl-CoA dehydratase activity, and the fourth can encode a fourth polypeptide having acrylyl-CoA hydratase activity. Such a cell can produce acrylate as the carboxylate product. Alternatively, the first of the four exogenous nucleic acid molecules can encode a first polypeptide having 2-dehydro-3-deoxy-D-pentanoate aldolase activity, the second can encode a second polypeptide having xylonate dehydratase activity, the third can encode a third polypeptide having xylonolactonase activity, and the fourth can encode a fourth polypeptide having D-xylose dehydrogenase activity. Such a cell can produce a carbohydrate, such as D-xylose, as the organic product.

In yet another embodiment, the cell contains six exogenous nucleic acid molecules, each of the six exogenous nucleic acid molecules encoding a different polypeptide. For example, the first of the six exogenous nucleic acid molecules can encode a first polypeptide having 2,5-dioxovalerate dehydrogenase activity, the second can encode a second polypeptide having 5-dehydro-4-deoxy-D-glucarate dehydrogenase activity, the third can encode a third polypeptide having glucarate dehydratase activity, the fourth can encode a fourth polypeptide having aldehyde dehydrogenase activity, the fifth can encode a fifth polypeptide having glucuronolactone reductase activity, and the sixth can encode a sixth polypeptide having L-gulonolactone oxidase activity. Such a cell can produce a vitamin, for example L-ascorbate, as the organic product.

The organic product can contain more than three carbon atoms, and can be, for example, an amino acid.

In another embodiment, the cell is able to catabolize a pentose carbon such as ribose, arabinose, xylose, and lyxose.

In another embodiment the cell has reduced pyruvate decarboxylase activity or reduced alcohol dehydrogenase activity. For example, the cell can lack all pyruvate decarboxylase activity. The reduced pyruvate decarboxylase activity can be due to a disrupted genetic locus, where the locus normally has the nucleic acid sequence that encodes pyruvate decarboxylase. Alternatively, the cell could contain an antisense molecule, such as a ribozyme, that corresponds to an endogenous nucleic acid sequence, where the antisense molecule reduces the pyruvate decarboxylase activity. The cell can also contain an additional exogenous nucleic acid molecule that functions as a killer plasmid.

In another embodiment, the enzymatic activity of the polypeptide encoded by the exogenous nucleic acid leads to the formation of the organic product in an NADH-consuming manner.

In another embodiment, the cell produces at least about 60 grams of the organic product for every 100 grams of glucose consumed when the cell is cultured under optimal conditions for the production of the organic product.

In another aspect, the invention features a cell, e.g., a yeast cell, containing an exogenous nucleic acid molecule, where the exogenous nucleic acid molecule encodes a polypeptide that promotes catabolism of a pentose carbon by the cell. The polypeptide can be, for example, xylose reductase, xylitol dehydrogenase, or xylulokinase, and the pentose carbon can be, for example, ribose, arabinose, xylose, and lyxose. The cell can further catabolize a hexose carbon and can, if desired, simultaneously catabolize the hexose carbon and the pentose carbon. The hexose carbon can be, for example, allose, altrose, glucose, mannose, gulose, iodose, fructose, galactose, and talose.

In another aspect, the invention features a yeast cell containing an exogenous nucleic acid molecule, where the exogenous nucleic acid molecule encodes a polypeptide that promotes accumulation of acetyl-CoA in the cytoplasm of the cell.

The polypeptide can be a polypeptide that has citrate lyase activity, or can be a mitochondrial membrane polypeptide that promotes acetyl-CoA permeability across the mitochondrial membrane. The cell can have reduced pyruvate decarboxylase activity or reduced alcohol dehydrogenase activity. Alternatively, the yeast cell can lack ethanol production, and can have a growth rate under culture conditions lacking ethanol and acetate that is greater than the growth rate observed for a comparable yeast cell lacking ethanol production.

In yet another aspect, the invention features a yeast cell having reduced activity of a mitochondrial polypeptide, where the cell has a crabtree-negative phenotype. Such a cell can be from, for example, the genus *Kluyveromyces, Pichia, Hansenulo, Candida, Trichosporon,* or *Yamadazyma*. The cell can completely lack the activity. The cell can contain a disrupted locus, where the locus normally includes a nucleic acid sequence that encodes the mitochondrial polypeptide. The mitochondrial polypeptide can be a Krebs cycle enzyme. Further, the cell can accumulate a Krebs cycle product. The cell can include an exogenous nucleic acid molecule, where the exogenous nucleic acid molecule encodes a polypeptide having enzymatic activity within the cell, with the enzymatic activity leading to formation of an organic product, such that the cell produces the organic product. The organic product can be, for example, citrate, alpha-ketoglutarate, succinate, fumarate, malate, and oxaloacetate. The polypeptide can be a polypeptide that participates in the catabolism of lactate or acetate.

In another aspect, the invention features a method for producing an organic product. The method includes providing yeast cells, where the cells include an exogenous nucleic acid molecule that encodes a polypeptide having enzymatic activity within the cells, where the enzymatic activity leads to the formation of the organic product, and where the cells have a crabtree-negative phenotype, and culturing the cells with culture medium such that the organic product is produced. The yeast cells can be from within the genus *Kluyveromyces, Pichia, Hansenula, Candida, Trichosporon,* or *Yamadazyma*. The organic product can be a fermentation product, a pyruvate-derived product, an organic product containing more than three carbon atoms, a carboxylate, carbohydrate, amino acid, vitamin, or lipid product. The organic product further can be lactate, glycerol, acrylate, xylose, ascorbate, citrate, isocitrate, alpha-ketoglutarate, succinyl-CoA, succinate, fumarate, malate, or oxaloacetate. In some embodiments, the organic product is secreted by the cells. The method can result in cells having reduced pyruvate decarboxylase activity or reduced alcohol dehydrogenase activity. The enzymatic activity can lead to the formation of the organic product in an NADH-consuming manner.

Cells made by these methods can produce at least about 60 grams of the organic product for every 100 grams of glucose consumed when the culturing step is optimal for production of the organic product. The culture medium, which can be liquid, can include an inhibitor of cellular respiration, such as antimycin A, cyanide, or azide. The culturing step can include growing the cells under aerobic growth conditions followed by contacting said cells with an inhibitor of cellular respiration.

In an alternative embodiment, the culturing step includes incubating the cells under anaerobic culture conditions. In a further alternative embodiment, the culturing step includes growing the cells under aerobic growth conditions followed by incubating the cells under anaerobic culture conditions. The culturing step can also include culturing the cells at a temperature greater than about 35° C.

In one embodiment, the culture medium has an organic pH value less than about 3.0, and/or an inorganic pH value less than about 3.0. In another embodiment, the medium contains a pentose carbon such as ribose, arabinose, xylose, or lyxose. The medium also can include a corn fiber hydrolysate having, for example, a pH value between about 2.0 and about 6.5.

In another aspect, the invention features a method for producing an organic product, the method including a) providing yeast cells containing an exogenous nucleic acid molecule encoding a polypeptide that promotes catabolism of a pentose carbon by the cell, where the cell contains an enzymatic activity that leads to the formation of said organic product, and b) culturing the cells with culture medium such that the organic product is produced.

In yet another aspect, the invention features a method for producing an organic product, the method including a) providing yeast cells, where the cells include an exogenous nucleic acid molecule encoding a polypeptide that promotes accumulation of acetyl-CoA in the cytoplasm of the cell, and where the cell contains an enzymatic activity that leads to the formation of the organic product, and b) culturing the cells with culture medium such that the organic product is produced.

In another aspect, the invention features a method for producing an organic product, the method including a) providing yeast cells having reduced activity of a mitochondrial enzyme, wherein reduction of the activity leads to the accumulation of the organic product, and b) culturing said cells with culture medium such that said organic product is produced.

In another aspect, the invention features a method for culturing yeast cells having a crabtree-negative phenotype, the method including culturing the cells with culture medium, where the culture medium has an organic pH value less than about 3.0 and/or an inorganic pH value less than about 3.0. The culturing step can include culturing the cells at a temperature greater than about 35° C. The culture medium can include an inhibitor of cellular respiration. The culture medium also can include a pentose carbon. In another embodiment, the culture medium can include a corn fiber hydrolysate.

In another aspect, the invention features a method for culturing yeast cells having a crabtree-negative phenotype, the method including culturing the cells with culture medium, where the culture medium includes a corn fiber hydrolysate.

In another aspect, the invention features a method for culturing yeast cells having a crabtree-negative phenotype, the method including culturing the cells with culture medium at a temperature greater than about 35° C., with the culture medium having an inorganic pH value less than about 3.0.

In another aspect, the invention features a method for culturing yeast cells having a crabtree-negative phenotype, the method including culturing the cells with culture medium at a temperature greater than about 35° C., with the culture medium including a pentose carbon.

In another aspect, the invention features a method for culturing yeast cells having a crabtree-negative phenotype, the method including culturing the cells with culture medium at a temperature greater than about 35° C., with the culture medium including a corn fiber hydrolysate.

In another aspect, the invention features a nucleic acid construct that includes a recombination sequence and a selected sequence, with the recombination sequence corresponding to a genomic sequence of a cell having a crabtree-negative phenotype, with the genomic sequence encoding an enzyme expressed by the cell, and with the selected sequence encoding an enzyme that leads to the formation of an organic product within the cell. The selected sequence can be within the recombination sequence such that the selected sequence is flanked on each end by the recombination sequence.

In another aspect, the invention features a method for making a recombinant yeast cell, including providing a yeast cell having a crabtree-negative phenotype, selecting an end product, identifying which exogenous enzyme or enzymes need to be added to the cell to produce the end product, identifying which endogenous enzyme or enzymes whose activity is to be reduced in said cell to allow production of said end product within said cell, adding the identified exogenous enzyme or enzymes to the provided yeast cell, and reducing the activity of the identified endogenous enzyme or enzymes in the provided yeast cell such that the cell produces the end product under culture conditions.

In another aspect, the invention features a corn fiber hydrolysate, the hydrolysate having a pH value between about 2.0 and about 6.5. The hydrolysate can include glucose, xylose, and arabinose. The hydrolysate can include about 40 grams/L glucose, about 40 grams/L xylose, and about 20 grams/L arabinose. Alternatively, the hydrolysate can include about 38.7 grams/L-glucose, about 39.1 grams/L-xylose, about 20.7 grams/L-arabinose, and about 1.6 grams/L-furfural.

In another aspect, the invention features a method for making an organic product, including a) culturing a microorganism under culture conditions, where the microorganism has reduced enzymatic activity; the enzymatic activity can be pyruvate decarboxylase, alcohol dehydrogenase, aldehyde dehydrogenase, or acetyl-CoA synthase activity; the microorganism exhibits a growth rate in the absence of ethanol and acetate that is at least about 30 percent of that observed for a corresponding microorganism not having said reduced enzymatic activity, and b) changing the culture conditions to promote production of the organic product.

In another aspect, the invention features a method for making an organic product, including a) culturing a microorganism under culture conditions that promote cellular respiration, where the microorganism has reduced enzymatic activity; the enzyme activity can be pyruvate decarboxylase, alcohol dehydrogenase, aldehyde dehydrogenase, or acetyl-CoA synthase activity, with the microorganism exhibiting a growth rate in the absence of ethanol and acetate that is at least about 30 percent of that observed for a corresponding microorganism not having such reduced enzymatic activity, and b) changing the culture conditions to reduce cellular respiration, thereby promoting production of the organic product.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DETAILED DESCRIPTION OF PREFERRED EMBODIMENTS

Figure 1:
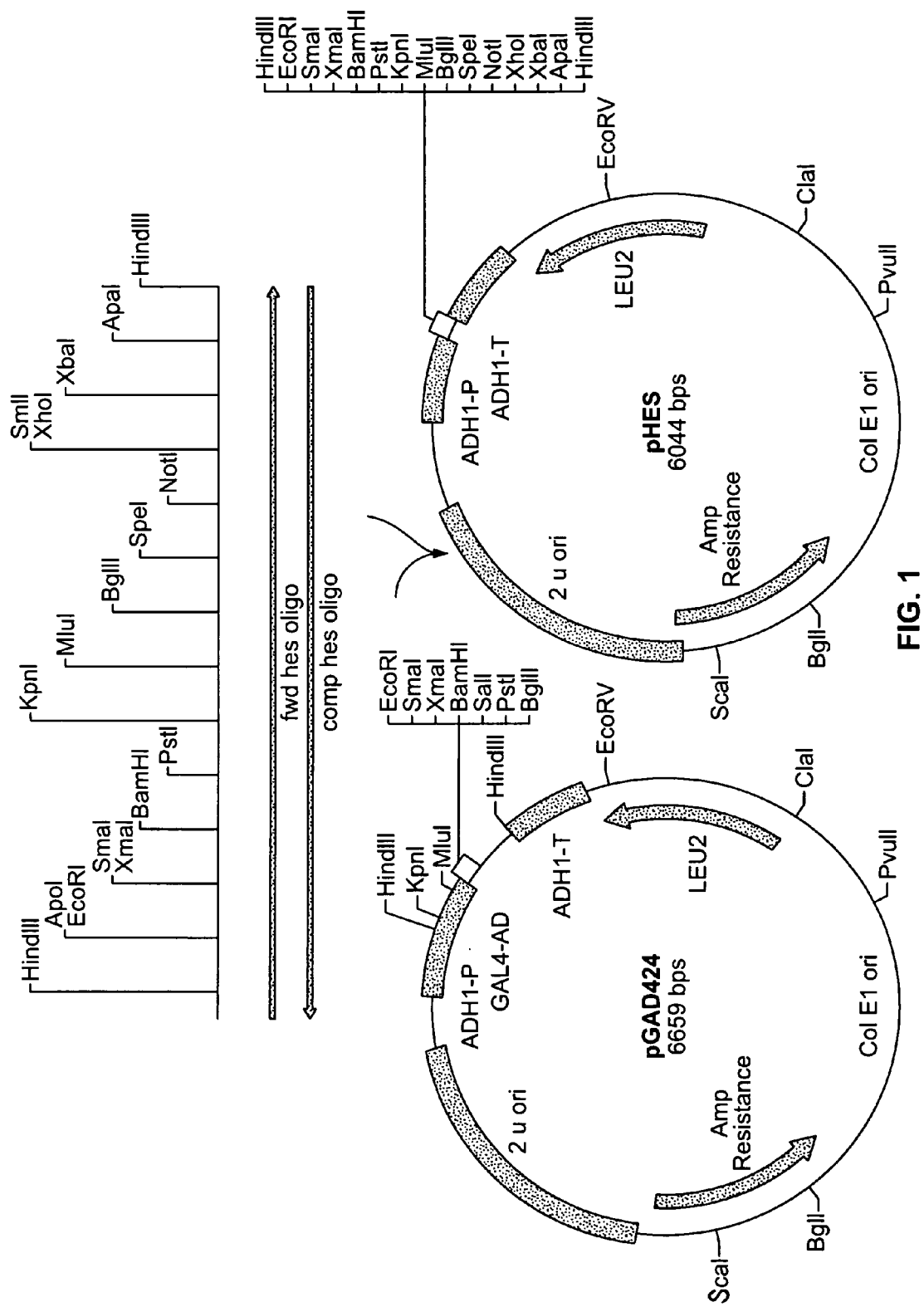
FIG. 1 is a diagram depicting the pHES plasmid.

The invention provides methods and materials related to the production of organic products. Specifically, the invention provides yeast cells, methods for culturing yeast cells, methods for making yeast cells, nucleic acid constructs, and methods and materials for producing various organic products.

The yeast cells provided herein can be used to produce organic products. Such organic products can be used in a wide range of applications. For example, organic products produced by the yeast cells described herein can be used as preservatives or additives in food, pharmaceutical, or cosmetic products, and can be used to make plastic as well as other products.

For the purpose of this invention, an organic product is any compound containing a carbon atom. For example, carboxylates (e.g., lactate, acrylate, citrate, isocitrate, alpha-ketoglutarate, succinate, fumarate, malate, oxaloacetate), carbohydrates (e.g., D-xylose), alditols (e.g., xylitol, arabitol, ribitol), amino acids (e.g., glycine, tryptophan, glutamate), lipids, esters, vitamins (e.g., L-ascorbate), polyols (e.g., glycerol, 1,3-propanediol, erythritol), aldehydes, alkenes, alkynes, and lactones are organic products. Thus, an organic product can contain one, two, three, four, five, six, seven, eight, nine, ten or more carbon atoms. In addition, organic products can have a molecular weight that is less than about 1,000 (e.g., less than about 900, 800, 700, 600, 500, 400, 300, 200, or 100). For example, D-xylose ($C_5H_{10}O_5$) is an organic product that has a molecular weight of 150. Further, organic products can be fermentation products. The term "fermentation product" as used herein refers to any organic compound that is produced by a fermentation process.

In general terms, a fermentation process involves the anaerobic enzymatic conversion of organic compounds such as carbohydrates to compounds such as ethyl alcohol, resulting in energy in the form of adenosine triphosphate (ATP). Thus, fermentation differs from cellular respiration in that organic products rather than molecular oxygen are used as electron acceptors. Examples of fermentation products include, without limitation, acetate, ethanol, butyrate, and lactate.

Organic products also can be pyruvate-derived products. The term "pyruvate-derived product" as used herein refers to any compound that is synthesized from pyruvate within no more than fifteen enzymatic steps. An enzymatic step is any chemical reaction or series of reactions catalyzed by a polypeptide having enzymatic activity. The term "polypeptide having enzymatic activity" as used herein refers to any polypeptide that catalyzes a chemical reaction of other substances without itself being destroyed or altered upon completion of the reaction or reactions. Typically, an enzymatic polypeptide catalyzes the formation of one or more products from one or more substrates. Such polypeptides can have any type of enzymatic activity including, without limitation, the enzymatic activity associated with an enzyme such as aconitase, isocitrate dehydrogenase, ketoglutarate dehydrogenase, succinate thiokinase, succinate dehydrogenase, fumarase, malate dehydrogenase, citrate synthase, 2,5-dioxovalerate dehydrogenase, 5-dehydro-4-deoxy-D-glucarate dehydratase, glucarate dehydratase, aldehyde dehydrogenase, glucuronolactone reductase, L-gulonolactone oxidase, 2-dehydro-3-deoxy-D-pentanoate aldolase, xylonate dehydratase, xylonolactonase, D-xylose dehydrogenase, lactate dehydrogenase, CoA-transferase, lactyl-CoA dehydratase, or acrylyl-CoA hydratase.

It is important to note that a polypeptide having a particular enzymatic activity can be a polypeptide that is either naturally-occurring or non-naturally-occurring. A naturally-occurring polypeptide is any polypeptide having an amino acid sequence as found in nature, including wild-type and polymorphic polypeptides. Such naturally-occurring polypeptides can be obtained from any species including, without limitation, mammalian, fungal, and bacterial species. A non-naturally-occurring polypeptide is any polypeptide having an amino acid sequence that is not found in nature. Thus, a non-naturally-occurring polypeptide can be a mutated version of a naturally-occurring polypeptide, or an engineered polypeptide. For example, a non-naturally-occurring polypeptide having citrate synthase activity can be a mutated version of a naturally-occurring polypeptide having citrate synthase activity that retains at least some citrate synthase activity. A polypeptide can be mutated by, for example, sequence additions, deletions, and/or substitutions.

An organic product is not a pyruvate-derived product if that product is synthesized from pyruvate requiring more than fifteen enzymatic steps. Examples of pyruvate-derived products include, without limitation, citrate, alpha-ketoglutarate, succinate, fumarate, malate, oxaloacetate, 2-dehydro-3-deoxy-D-xylonate, D-xylonate, D-xylonolactone, D-xylose, acrylate, acetate, ethanol, butyrate, and lactate.

For purposes of this invention, carboxylate products, which can be in a "free acid" or "salt" form, will be referred to using the salt form nomenclature. For example, lactic acid will be referred to as lactate. Thus, in this case, it will be appreciated that the term "lactate" includes lactic acid as well as lactate.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear. The term "exogenous" or "heterologous" as used herein with reference to a nucleic acid molecule and a particular cell refers to any nucleic acid molecule that does not originate from that particular cell as found in nature. Thus, all non-naturally-occurring nucleic acid molecules are considered to be exogenous to a cell once introduced into the cell. It is important to note that non-naturally-occurring nucleic acid molecules can contain nucleic acid sequences or fragments of nucleic acid sequences that are found in nature provided the nucleic acid molecule as a whole does not exist in nature. For example, a nucleic acid molecule containing a genomic DNA sequence within an expression vector is considered to be a non-naturally-occurring nucleic acid molecule, and thus is considered lobe exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be a non-naturally-occurring nucleic acid molecule. It follows that genomic DNA fragments produced by PCR or restriction endonuclease treatment as well as cDNA's are considered to be non-naturally-occurring nucleic acid molecules since they exist as separate molecules not found in nature. It also follows that any nucleic acid molecule containing a promoter sequence and polypeptide-encoding sequence (e.g., cDNA or genomic DNA) in an arrangement not found in nature is considered to be a non-naturally-occurring nucleic acid molecule.

The term "endogenous" refers to genomic material that is not exogenous. Generally, endogenous genomic material develops within an organism, tissue, or cell, and is not inserted or modified by recombinant technology. Endogenous genomic material does include within its scope naturally occurring variations.

It also is important to note that a nucleic acid molecule that is naturally-occurring can be exogenous to a particular cell. For example, an entire chromosome isolated from a cell of person X would he considered an exogenous nucleic acid molecule with respect to a cell of person Y once that chromosome is introduced into Y's cell.

As used herein, the phrase "genetically modified" refers to an organism whose genome has been modified, for example, by addition, substitution or deletion of genetic material. Methods for adding or deleting genetic material are known and include, but are not limited to, random mutagenesis, point mutations, including insertions, deletions and substitutions, knock-out technology, and transformation of an organism with a nucleic acid sequence using recombinant technology, including both stable and transient transformants. The yeast cells may also catabolize starch, either naturally or because of a genetic modification, and may even be genetically modified to catabolize cellulosics through the addition of, for example, fungal based cellulases.

1. Yeast Cells Having a Crabtree-Negative Phenotype

The invention provides a variety of genetically manipulated yeast cells that have a crabtree-negative phenotype. Such recombinant yeast cells can be used to produce organic products. For example, the invention provides a yeast cell that has a crabtree-negative phenotype, and contains an exogenous nucleic acid molecule that encodes a polypeptide having enzymatic activity that leads to the formation of an organic product. Such yeast cells are within the scope of the invention provided they produce the organic product. It is noted that the produced organic product can be secreted from the yeast cell, eliminating the need to disrupt the cell membrane to retrieve the organic product. Typically, the yeast cells of the invention produce the organic product with the yield being at least about 40 grams (e.g., at least about 45, 50, 55, 65, 70, 75, 80, 85, 90, or 95 grams) of organic product for every 100 grams of glucose consumed when cultured under optimal conditions for product production. When determining the yield of organic product production for a particular yeast cell, any method can be used. See, e.g, Kiers et al., *Yeast*, 14(5):459–469 (1998). It also is noted that the enzymatic activity of the encoded polypeptide can lead to the formation of the organic product in an NADH-consuming manner. In other words, the production of the organic compound can require NADH as an energy source. The term "NAD" refers to the co-factors that act as electron and hydrogen carriers in particular oxidation-reduction reactions, while the term "NADH" refers to the reduced form of NAD. Examples of organic products whose synthesis requires NADH include, without limitation, lactate, ethanol, acetate, and acrylate. Typically, the yeast cells within the scope of the invention catabolize a hexose carbon such as glucose. However, such yeast cells also can catabolize a pentose carbon (e.g., ribose, arabinose, xylose, and lyxose). In other worth, a yeast cell within the scope of the invention can either naturally utilize a pentose carbon, or can be engineered to utilize a pentose carbon. For example, a yeast cell can be given an exogenous nucleic acid molecule that encodes xylose reductase, xylitol dehydrogenase, and/or xylulokinase such that xylose can be catabolized. The yeast cells may also catabolize starch, either naturally or because of a genetic modification, and may even be genetically modified to catabolize cellulosics through the addition of, for example, fungal based cellulases. A yeast cell having a crabtree-negative phenotype is any yeast cell that does not exhibit the crabtree effect. The term "crabtree-negative" refers to both naturally occurring and genetically modified organisms. Briefly, the crabtree effect is defined as the inhibition of oxygen consumption by a microorganism when cultured under aerobic conditions due to the presence of a high glucose concentration (e.g., 50 grams of glucose/L). In other worth, a yeast cell having a crabtree-positive phenotype continues to ferment irrespective of oxygen availability due to the presence of glucose, while a yeast cell having a crabtree-negative phenotype does not exhibit glucose mediated inhibition of oxygen consumption. Examples of yeast cells typically having a crabtree-negative phenotype include, without limitation, yeast cells from the following genera: *Kluyveromyces, Pichia, Hansenulo, Candida, Trichosporon,* and *Yamadaryrna.*

As described herein, the invention provides many different types of recombinant yeast cells capable of producing a wide variety of different organic products. For example, a yeast cell can contain an exogenous nucleic acid molecule that encodes a polypeptide having lactate dehydrogenase activity such that lactate is produced. Examples of such a polypeptide include, without limitation, bovine lactate dehydrogenase, bacterial lactate dehydrogenase, and fungal lactate dehydrogenase (e.g., *K. lactis* or *K. thermotolerans* fungal lactate dehydrogenase). Again, polypeptides having enzymatic activity such as a lactate dehydrogenase activity can be naturally-occurring or non-naturally-occurring. It is important to note that the yeast cells described herein can contain a single copy, or multiple copies (e.g., about 5, 10, 20, 35, 50, 75, 100 or 150 copies), of a particular exogenous nucleic acid molecule. For example, a yeast cell can contain about 50 copies of exogenous nucleic acid molecule X. It also is important to note that the yeast cells described herein can contain more than one particular exogenous nucleic acid molecule. For example, a yeast cell can contain about 50 copies of exogenous nucleic acid molecule X as well as about 75 copies of exogenous nucleic acid molecule Y. In these eases, each different nucleic acid molecule can encode a different polypeptide having its own unique enzymatic activity. For example, a yeast cell can contain four different exogenous nucleic acid molecules such that acrylate is produced. In this example, such a yeast cell can contain a first exogenous nucleic acid molecule that encodes a polypeptide having lactate dehydrogenase activity, a second that encodes a polypeptide having CoA-transferase activity, a third that encodes a polypeptide having lactyl-CoA dehydratase activity, and a fourth that encodes a polypeptide having acrylyl-CoA hydratase activity. In another example, a yeast cell can contain four different exogenous nucleic acid molecules such that D-xylose is produced. Specifically, such a yeast cell can contain a first exogenous nucleic acid molecule that encodes a polypeptide having 2-dehydro-3-deoxy-D-pentanoate aldolase activity, a second that encodes a polypeptide having xylonate dehydratase activity, a third that encodes a polypeptide having xylonolactonase activity, and a fourth that encodes a polypeptide having D-xylose dehydrogenase activity. In yet another example, a yeast cell can contain six different exogenous nucleic acid molecules such that the vitamin, L-ascorbate, is produced. Specifically, such a yeast cell can contain a first exogenous nucleic acid molecules that encodes a polypeptide having 2,5-dioxovalerate dehydrogenase activity, a second that encodes a polypeptide having 5-dehydro-4-deoxy-D-glucarate dehydrogenase activity, a third that encodes a polypeptide having glucarate dehydratase activity, a fourth that encodes a polypeptide having aldehyde dehydrogenase activity, a fifth that encodes a polypeptide having glucuronolactone reductase activity, and a sixth that encodes a polypeptide having L-gulonolactone oxidase activity.

It is important to note that enzymatic polyp peptides can be used such that the desired organic product is optically pure (e.g., about 90, 95, 99% pure). For example, a polypeptide having an (L)-lactate dehydrogenase activity can be used to produce (L)-lactate.

Yeast cells within the scope of the invention also can have reduced enzymatic activity such as reduced pyruvate decarboxylase and/or alcohol dehydrogenase activity. The term "reduced" as used herein with respect to a cell and a particular enzymatic activity refers to a lower level of enzymatic activity than that measured in a comparable yeast cell of the same species. Thus, a yeast cell lacking pyruvate decarboxylase activity is considered to have reduced pyruvate decarboxylase activity since most, if not all, comparable yeast cells have at least some pyruvate decarboxylase activity. Such reduced enzymatic activities can be the result of lower enzyme concentration, lower specific activity of an enzyme, or combinations thereof. Many different methods can be used to make a yeast cell having reduced enzymatic activity. For example, a yeast cell can be engineered to have a disrupted enzyme-encoding locus using common mutagenesis or knock-out technology. See, *Methods in Yeast Genetics* (1997 edition), Adams, Gottschling, Kaiser, and Stems, Cold Spring Harbor Press (1998). Alternatively, antisense technology can be used to reduce enzymatic activity. For example, a yeast cell can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axhead structures, provided the molecule cleaves RNA.

Yeast cells having a reduced enzymatic activity can be identified using any method. For example, a yeast cell having reduced pyruvate decarboxylase activity can be easily identified using common methods. See, Ulhrich, *Methods in Enzymology* 18:109–115 (1970).

2. Yeast Cells Having a Crabtree-Positive or Crabtree-Negative Phenotype

The invention also provides a variety of genetically manipulated yeast cells that need not have a crabtree-negative phenotype, i.e., such cells can be either crabtree-positive or crabtree-negative. Such recombinant yeast cells can be used to produce organic products. For example, the invention provides a yeast cell containing an exogenous nucleic acid molecule that encodes a polypeptide that promotes catabolism of a pentose carbon (e.g., ribose, arabinose, xylose, and lyxose) by the cell. Specifically, a yeast cell can have an exogenous nucleic acid molecule that encodes xylose reductase, xylitol dehydrogenase, and/or xylulokinase such that xylose can be metabolized in a more efficient manner. In addition, the yeast cells capable of catabolizing a pentose carbon also can be capable of catabolizing a hexose carbon (e.g., allose, altrose, glucose, mannose, gulose, iodose, galactose, and talose) either sequentially or simultaneously. For example, a yeast cell can be engineered such that xylose and glucose are catabolized simultaneously. It is noted that yeast cells having an increased ability to catabolize a pentose carbon can be used to engineer yeast cells that can produce organic products from pentose carbon sources. This characteristic is particularly advantageous since pentose carbon sources such as xylose are generally less expensive than hexose carbon sources such as glucose. Other carbon sources that can be catabolized include, without limitation, melibiose, sucrose, fructose, raffinose, stachyose, starch (e.g., corn starch and wheat starch), and hydrolysate (e.g., corn fiber hydrolysate and other cellulosic hydrolysates).

In addition, the invention provides a yeast cell containing an exogenous nucleic acid molecule that encodes a polypeptide that promotes accumulation of acetyl-CoA in the cytoplasm of the cell. For example, a yeast cell can have an exogenous nucleic acid molecule that encodes a polypeptide having citrate lyase activity. Alternatively, a yeast cell can have an exogenous nucleic acid molecule that encodes a mitochondrial membrane polypeptide that promotes acetyl-CoA permeability across the mitochondrial membrane. It is noted that many yeast cells lacking the ability to produce ethanol cannot grow in the absence of ethanol and acetate. Typically, a yeast cell will lack the ability to produce ethanol when either pyruvate decarboxylase or alcohol dehydrogenase activity is lacking in some manner. For example, crabtree-positive yeast (e.g., *Saccharomyces*) lacking pyruvate decarboxylase activity grow poorly in the absence of ethanol and acetate.

Thus, manipulation of such crabtree-positive yeast in a manner that reduces ethanol production in order to redirect the utilization of pyruvate to other organic products (e.g., lactate and acrylate) results in poor growth characteristics when ethanol and acetate are absent, particularly since crabtree-positive yeast limit cellular respiration when in the presence of glucose. As described herein, yeast cells that can promote accumulation of cytoplasmic acetyl-CoA in some manner other than that which relies on cytoplasmic acetate concentration and acetyl-CoA synthase activity can grow in the absence of ethanol and acetate even when unable to produce ethanol. It is noted that yeast cells having the ability to grow in the absence of ethanol and acetate while lacking the ability to produce ethanol can redirect the utilization of pyruvate to produce organic products other than ethanol.

Any type of yeast can contain an exogenous nucleic acid molecule that encodes a polypeptide that promotes accumulation of acetyl-CoA in the cytoplasm of the cell. For example, a yeast cell having a crabtree-negative or crabtree-positive phenotype can contain an exogenous nucleic acid molecule that encodes a polypeptide that promotes accumulation of acetyl-CoA in the cytoplasm of the cell. Typically, such yeast cells can be identified by (1) manipulating the cell that contains the exogenous nucleic acid molecule such that it lacks pyruvate decarboxylase or alcohol dehydrogenase activity, (2) determining the growth characteristics of the cell while culturing the cell in the presence of titrating amounts of a respiratory inhibitor (e.g., antimycin A, cyanide, or azide), and (3) comparing those growth characteristics to those observed for a comparable yeast cell that does not contain the exogenous nucleic acid molecule, yet that also was manipulated to lack pyruvate decarboxylase or alcohol dehydrogenase activity. Yeast cells determined to have more favorable growth characteristics due to the presence of the exogenous nucleic acid molecule by such a comparison are considered to contain an exogenous nucleic acid molecule that encodes a polypeptide that promotes accumulation of acetyl-CoA in the cytoplasm of the cell.

Yeast cells containing an exogenous nucleic acid molecule that encodes a polypeptide that promotes accumulation of acetyl-CoA in the cytoplasm of the cell also can have reduced enzymatic activity, such as reduced pyruvate decarboxylase and/or alcohol dehydrogenase activity. For example, a yeast cell can lack the ability to produce ethanol. Typically, such yeast cells have a growth rate under culture conditions lacking ethanol and acetate that is greater (e.g., about 5, 10, 20, 35, 50, 75, 100, 150, 200 percent, or more) than the growth rate observed for comparable yeast cells (i.e., yeast cells lacking the ability to produce ethanol) that do not contain the exogenous nucleic acid, yet were cultured under similar conditions (i.e., culture conditions lacking ethanol and acetate).

The invention also provides a yeast cell having reduced activity of a polypeptide. Such yeast cells can have a crabtree-positive or crabtree-negative phenotype. For example, a yeast cell within the scope of the invention can have reduced activity of a plasma membrane polypeptide (e.g., a plasma membrane transporter), a cytoplasmic polypeptide (e.g., pyruvate decarboxylase), and/or a mitochondrial polypeptide (e.g., pyruvate dehydrogenase). The term "plasma membrane transporter" refers to polypeptides that facilitate the movement of organic products across the plasma membrane. Examples of such a polypeptide include, without limitation, carboxylic acid transporters such as JEN1 in *S. cerevisiae* (Genbank accession number U241 55). The term "mitochondrial polypeptide" refers to any polypeptide that functions within the mitochondria including, without limitation, pyruvate dehydrogenase, polypeptides that participate in the catabolism of lactate or acetyl-CoA (e.g., cytochrome b2 polypeptides), and Krebs cycle enzymes. Krebs cycle enzymes include aconitase, isocitrate dehydrogenase, ketoglutarate dehydrogenase, succinate thiokinase, succinate dehydrogenase, fumarase, malate dehydrogenase, and citrate synthase. As described herein, a yeast cell having a reduced enzyme activity includes a yeast cell that completely lacks a particular enzymatic activity. it is important to note that the term "reduced" as used herein with respect to a yeast cell and polypeptide activity refers to a lower level of activity than that measured in a comparable yeast cell of the same species under similar conditions. Thus, a yeast cell lacking a particular transport activity is considered to have reduced transport activity if a comparable cell has at least some transport activity. Such reduced polypeptide activities can be the result of lower polypeptide concentration, lower specific activity of the polypeptide, or combinations thereof. Any of various methods can be used to make a yeast cell having reduced polypeptide activity. For example, the locus having a nucleic acid sequence that encodes a mitochondrial polypeptide can be rendered inactive by, for example, common mutagenesis or knock-out technology.

It is noted that yeast cells having reduced activity of a mitochondrial enzyme can accumulate Krebs cycle products (e.g., citrate, isocitrate, alpha-ketoglutarate, succinyl-CoA, succinate, fumarate, malate, and oxaloacetate). For example, yeast cells having reduced fumarase activity can accumulate fumarate. In addition, the yeast cell can contain an exogenous nucleic acid molecule that encodes a polypeptide having enzymatic activity that leads to the formation of an organic product such that the cell produces the organic product.

It is important to note that some Krebs cycle products cannot permeate the mitochondrial membrane (e.g., alpha-ketoglutarate and succinyl-CoA). Thus, reducing the activity of particular Krebs cycle enzymes will result in the accumulation of certain Krebs cycle products within the lumen of the mitochondria. In these cases, yeast cells having a reduced activity of a Krebs cycle enzyme can be engineered to contain one or more different exogenous nucleic acid molecules, each of which encode a polypeptide having a different enzymatic activity, such that the desired Krebs cycle product accumulates within the cytoplasm. For example, reducing the activity of ketoglutarate dehydrogenase will lead to an accumulation of alpha-ketoglutarate, which in turn will lead to an accumulation of isocitrate. Alpha-ketoglutarate cannot permeate the mitochondrial membrane, whereas isocitrate can permeate the mitochondrial membrane. Thus, isocitrate can accumulate within the cytoplasm of the cell. However, yeast cells that also contain an exogenous nucleic acid molecule that encodes a polypeptide having isocitrate dehydrogenase activity, and express that functional polypeptide within the cytoplasm can produce cytoplasmic alpha-ketoglutarate. Thus, reducing the activity of particular Krebs cycle enzymes while providing exogenous nucleic acid molecules that encode the same (or different) Krebs cycle enzymes that are functional within the cytoplasm can lead to the production of various Krebs cycle products (or products derived from Krebs cycle products) within the cytoplasm.

Further, the invention provides a yeast cell having reduced activity of an enzyme that diverts the utilization of a carbon source away from the production of either biomass or the desired organic product. For example, enzymes within the glycerol or certain pathways can be disrupted and the carbon source within the culture medium is utilized predominately for the production of biomass or the desired organic product. Examples of glycerol pathway enzymes include, without limitation, dihydroxyacetone phosphate reductase. Examples of certain pathway enzymes include, without limitation, alpha-acetolactate synthase and alpha-acetolactate decarboxylase. Again, any method can be used to reduce the activity of an enzyme.

Moreover, any of the yeast cells provided herein can contain an exogenous nucleic acid molecule that functions as a killer plasmid. The term "killer plasmid" as used herein refers to a nucleic acid molecule that provides one species of yeast with the ability to kill another species of yeast. For example, yeast cells from the genus *Kluyveromyces* containing a killer plasmid can prevent the growth of yeast from the genus *Saccharomyces*. Thus, yeast cells having a killer plasmid can be used to prevent contamination problems that arise during large-scale production processes. In addition, any type of killer plasmid can be given to a yeast cell. For example, a killer plasmid isolated from *K. thetis* can be given to a *K. marxianus* yeast cell. Yeast cells containing a killer plasmid can be easily identified using common methods. See, e.g., Gunge et al., *J. Bacteriol.* 145:382–390 (1981); Gunge and Kitada, *Eur. J. Epidemiol.*,4:409–414 (1988); and Wesolowski-Louvel et al., *Nonconventional yeasts in Biotechnology; Kluyveromyces lactis*, ed Klaus Wolf, Springer Verlag, Berlin, p. 138–201 (1996).

Likewise, any of the yeast cells provided herein can contain an exogenous nucleic acid molecule that encodes a polypeptide having an ATPase activity modified such that the yeast cell becomes more tolerant to low pH environments. For example, a yeast cell can he given an ATPase that effectively maintains a low cytoplasmic proton concentration when the extracellular proton concentration is high. Such polypeptides can be engineered as described by Morsomme et al. (*EMBO J.* 15:5513–5526 (1996)).

It is important to note that any of the recombinant yeast cells described herein can contain any combination of the described genetic manipulations. For example, a yeast cell having a crabtree-positive phenotype can contain an exogenous nucleic acid molecule that encodes a polypeptide having citrate lyase activity as well as an exogenous nucleic acid molecule that encodes a polypeptide having enzymatic activity that leads to the formation of an organic product.

3 Suitable Organisms

A variety of organisms are suitable for use in accordance with the invention. In addition to crabtree negative and crabtree positive yeast microorganisms such as *Saccharomyces* Sp., including *S. cerevisiae* and *S. uvarum*, *Kluyveromyces*, including *K. thermotolerans*, *K. lactis*, and *K. marxianus*, *Pichia*, *Hansenula*, including *H. polymorpha*, *Candidia*, *Trichosporon*, *Yamadazyma*, including *Y. styptic.*, or *Torulaspora pretoriensis*, organisms from a wide array of microbial species could also serve as hosts for lactic acid production. For example, an organism such as *Rhizopus oryzae*, a natural producer of lactic acid, could be genetically modified for acid tolerance, yield improvement, and optically pure lactic acid. *Aspergillus* spp. are also known to produce a variety of organic acids, such as citric acid, and tolerate low pH. Methods for genetically modifying *Aspergillus* spp. to produce lactic acid are available. Moreover, fungi such as *Rhizopus* and *Aspergillus* spp. produce enzymes that enable them to degrade starch and other carbohydrate polymers to monomer carbohydrates for use as a carbon source.

Prokaryotes such as *Escherichia coli*, *Zymomonas mobilis*, and *Bacillus* spp. have been or can be genetically modified for lactic acid production. Microorganisms that have been identified as *Bacillus coagulans* are also natural producers of lactic acid that could be further genetically modified to improve low pH lactic acid production. Additionally, extremeophile organisms from the family Archea can tolerate extremely low pH and high temperatures. Genetic modification of selected species from this family could provide a lactic acid producing strain.

4. Genetic Aspects

A nucleic acid molecule encoding a polypeptide having enzymatic activity can be identified and obtained using any method. For example, standard nucleic acid sequencing techniques and software programs that translate nucleic acid sequences into amino acid sequences based on the genetic code can be used to determine whether or not a particular nucleic acid has any sequence homology with known enzymatic polypeptides. Sequence alignment software such as MEGALIGN® (DNASTAR, Madison, Wis., 1997) can be used to compare various sequences. In addition, nucleic acid molecules encoding known enzymatic polypeptides can be mutated using common molecular cloning techniques (e.g., site-directed mutagenesis). Possible mutations include, without limitation, deletions, insertions, and base substitutions, as well as combinations of deletions, insertions, and base substitutions. Further, nucleic acid and amino acid databases (e.g., GenBank®) can be used to identify a nucleic acid sequence that encodes a polypeptide having enzymatic activity. Briefly, any amino acid sequence having some homology to a polypeptide having enzymatic activity, or any nucleic acid sequence having some homology to a sequence encoding a polypeptide having enzymatic activity can be used as a query to search GenBank®. The identified polypeptides then can be analyzed to determine whether or not they exhibit enzymatic activity.

Nucleic acid molecules that encode a polypeptide having enzymatic activity can be identified and obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Further, nucleic acid hybridization techniques can be used to identify and obtain a nucleic acid molecule that encodes a polypeptide having enzymatic activity. Briefly, any nucleic acid molecule that encodes a known enzymatic polypeptide, or fragment thereof can be used as a probe to identify a similar nucleic acid molecules by hybridization under conditions of moderate to high stringency. Such similar nucleic acid molecules then can be isolated, sequenced, and analyzed to determine whether the encoded polypeptide has enzymatic activity. Hybridization can be done by Southern or Northern analysis to identify a DNA or RNA sequence, respectively, which hybridizes to a probe. The probe can be labeled with a radioisotope such as $^{32}P$, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al, (1989) *Molecular Cloning*, second edition, Cold Spring Harbor Laboratory, Plainview, N.Y. Typically, a probe is at least about 20 nucleotides in length. For example, a probe corresponding to a 20 nucleotide sequence that encodes a mammalian citrate lyase can be used to identify a nucleic acid molecule that encodes a fungal polypeptide having citric lyase activity. In addition, probes longer or shorter than 20 nucleotides can be used.

Any method can be used to introduce an exogenous nucleic acid molecule into a cell. In fact, many methods for introducing nucleic acid into yeast cells are well known to those skilled in the art. For example, transformation, electroporation, conjugation, and fusion of protoplasts are common methods for introducing nucleic acid into yeast cells. See, e.g., Ito et al., *J. Bacterol.* 153:163–168 (1983); Durrens et al., *Curr Genet.* 18:7–12 (1990); and Becker and Guarente, *Methods in Enzymology* 194:182–187 (1991).

It is important to note that the exogenous nucleic acid molecule contained within a yeast cell of the invention can be maintained within that cell in any form. For example, exogenous nucleic acid molecules can be integrated into the genome of the cell or maintained in an episomal state. In other words, a cell of the invention can be a stable or transient transformant. In addition, the yeast cells described herein can contain a single copy, or multiple copies (e.g., about 5, 10, 20, 35, 50, 75, 100 or 150 copies), of a particular exogenous nucleic acid molecule as described above. Methods for expressing an amino acid sequence from an exogenous nucleic acid molecule are well known to those skilled in the art. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Moreover, methods for expressing a polypeptide from an exogenous nucleic acid molecule in yeast are well known to those skilled in the art. For example, nucleic acid constructs that are capable of expressing exogenous polypeptides within *Kluyveromyces* are well known. See, e.g., U.S. Pat. Nos. 4,859,596 and 4,943,529.

As described herein, yeast cells within the scope of the invention contain an exogenous nucleic acid molecule that, for example, encodes a polypeptide having enzymatic activity that leads to the formation of an organic product. Methods of identifying cells that contain exogenous nucleic acid are well known to those skilled in the art. Such methods include, without limitation, PCR and nucleic acid hybridization techniques such as Northern and Southern analysis. In some cases, immunohistochemistry and biochemical techniques can be used to determine if a cell contains a particular nucleic acid by detecting the expression of the encoded enzymatic polypeptide encoded by that particular nucleic acid molecule. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting an organic product produced as a result of the expression of the enzymatic polypeptide.

For example, detection of lactate after introduction of an exogenous nucleic acid molecule that encodes a polypeptide having lactate dehydrogenase activity into a yeast cell that does not normally express such a polypeptide can indicate that that yeast cell not only contains the introduced exogenous nucleic acid molecule but also expresses the encoded enzymatic polypeptide from that introduced exogenous nucleic acid molecule. Methods for detecting specific enzymatic activities or the presence of particular organic products are well known to those skilled in the art. For example, the presence of lactate can be determined as described elsewhere. See, Witte et al., *J. Basic Microbiol.* 29:707–716 (1989).

The invention also provides a nucleic acid construct containing a recombination sequence and a selected sequence. The term "recombination sequence" as used herein refers to any nucleic acid sequence that corresponds to a genomic sequence found within a cell. The recombination sequences described herein can be used to direct recombination events during the generation of knock-out organisms. In other words, a recombination sequence can be used to specifically disrupt a locus containing a nucleic acid sequence that encodes a particular enzyme.

The term "selected sequence" as used herein includes any nucleic acid sequence. Typically, a selected sequence encodes a polypeptide having enzymatic activity that leads to the formation of an organic product within a cell. Thus, the nucleic acid constructs of the invention can be used to knockout an endogenous enzyme activity and add an exogenous enzyme activity in a single step. In most cases, the selected sequence is within the recombination sequence such that the selected sequence is flanked on each end by the recombination sequence.

5. Organic Product Production and Culturing Methods

The invention provides methods for producing organic products using any of the yeast cells or other microbial cells provided herein. Such methods involve providing yeast cells and culturing the provided yeast cells with culture medium such that an organic product (e.g., glycerol, acrylate, xylose, ascorbate, lactate, citrate, isocitrate, alpha-ketoglutarate, succinyl-CoA, succinate, fimarate, malate, and oxaloacetate) is produced. In general terms, the culture media and/or culture conditions can be classified into one of two categories: those that promote cellular respiration and/or the production of biomass and those that reduce cellular respiration. Typically, culture media and/or culture conditions that promote cellular respiration are used in situations where rapid growth is needed, or where the organic product to be produced cannot be produced without cellular respiration. Such organic products can include, without limitation, Krebs cycle products. On the other hand, culture medium and/or culture conditions that reduce cellular respiration are used in situations where rapid growth is not needed or not desired, or where the organic product to be produced can be produced without cellular respiration. Such organic products include, without limitation, lactate, acrylate, and xylose.

As used herein, the phrase "promote cellular respiration" or "promote biomass production" when referring to a culture conditions, means that the cell culture conditions are maintained such that the carbon source within the culture medium is predominantly metabolized by oxidative respiration or to produce biomass. As used herein, the term "biomass" refers to the dry weight of the organism. As used herein, the phrase "predominantly metabolized to produce biomass" means that at least about 0.3 grams biomass is produced per gram carbon source (in the form of carbohydrate) consumed (e.g., at least about 0.4, 0,45, 0.5 or 0.6 grams biomass). Generally, between about 0.3 to about 0.6 grams biomass is produced per gram carbon source. Methods for determining the amount of biomass (cell dry weight) in a culture are known and include, for example, the methods described by Postma et al, "Enzymic analysis of the Crabtree effect in glucose-limited chemostat cultures of *Saccharomyces cerevisiae,*" Appl Environ. Microbiol 53, 468–477 (1989); and Kliers et al., "Regulation of alcoholic fermentation in batch and chemostat cultures of *Kluyveromyces lactis* CBS 2359," *Yeast,* 14, 459–469 (1998). Methods for determining the amount of carbon source consumed are known, and include, for example HPLC methodologies.

It should be noted that the efficiency of carbon source utilization may depend on the carbon source and the organism. Thus, while a complex growth media that includes carbon sources other than carbohydrate may be used, the amount of biomass produced per gram carbon source refers only to the amount of biomass produced per gram carbohydrate carbon source consumed.

In general, culture medium containing an inhibitor of cellular respiration (e.g., antimycin A, cyanide, and aside) can reduce cellular respiration, while the absence of such inhibitors can promote cellular respiration. Likewise, anaerobic culture conditions can reduce cellular respiration, while aerobic culture conditions can promote cellular respiration. An aerobic condition is any condition where oxygen is introduced or occurs naturally and serves as a substrate for the respiratory pathway. Generally, the term "aerobic" refers to a culture condition in which the culture media is maintained under an air flow of at least 0.1 VVM (volume air/volume liquid/minute) (e.g., greater than 0.2, 0.3, 0.4, 0.5, 1.0, 1.5 or 2.0 VVM).

If a gas other than air is used then the nominal VVM is adjusted to an air equivalent based on oxygen content of the gas. Alternately, "aerobic" can be defined as a culture media that has a dissolved oxygen content of at least 2 percent (e.g., at least 5, 10, 20, 30, 40, 50, 60, 75 or 80 percent) relative to the amount present at saturated conditions with air at atmospheric pressure. An anaerobic condition is any condition where oxygen is purposely or naturally made essentially unavailable to the respiratory pathway, leading to, for example, the production of a reduced product such as ethanol. Generally, a condition where culture medium has a dissolved oxygen (DO) content less than about 2.0% (e.g., less than about 1.5, 1.0, or 0.5%, or equal to about 0%) is considered an anaerobic condition. Likewise, a condition having a VVM (volume air/volume liquid/minute) less than about 0.1 (e.g., less then about 0.05,or equal to about 0) is considered an anaerobic condition. Typically, the term "air" as used herein with respect to VVM refers to air as it exists in the atmosphere. Other culture conditions that can influence cellular respiration include, without limitation, pH, temperature, and the presence of particular carbon sources (e.g., glucose). It is important to note that some culture media and/or culture conditions that promote cellular respiration within one species of yeast can reduce cellular respiration within another species. For example, the presence of glucose within culture medium reduces cellular respiration in yeast cells having a crabtree-positive phenotype while having little or no effect on cellular respiration in yeast cells having a crabtree-negative phenotype.

Directed manipulation of culture conditions during a commercial production can be an important step in achieving optimal levels of a desired organic product as described herein. Typically, a yeast cell within the scope of the invention is grown under culture conditions that promote cellular respiration to produce a significant cell density. For example, yeast cells can be placed into a culture vessel, and given an abundance of glucose and oxygen. Typically, under conditions that promote cellular respiration, the doubling time for the microorganisms provided herein is less than about 10 hours (e.g., less than about 8, 5, or 3 hours). Once the cells reach a significant density, the culture conditions can be switched to conditions that reduce cellular respiration such that an organic product not requiring cellular respiration is produced. For example, the yeast cells can be transferred to a culture vessel and given an abundance of glucose, but no oxygen. In this case, directly manipulating the culture conditions such that they are switchedfrom aerobic to anaerobic can produce optimal levels of a desired organic product. Alternatively, in some cases, the cells can be cultured solely under conditions that promote cellular respiration such that an organic product requiring cellular respiration is produced. It is noted that the cell mass within the production vessel typically is greater than about 2 g/L (e.g., greater than about 4, 6, or 8 g/L).

During culturing, the temperature can be greater than about 35° C. (e.g., greater than about 36, 37, 38, 39, 40, 41,42, 43, 44, or 45° C.). In addition, the culture medium can be liquid. The culture media typically contains a carbon source. Generally, the carbon source includes carbohydrate containing raw materials. Typically, the nutrient media also contains a nitrogen source. Preferably the nitrogen source includes a combination of organic and inorganic nitrogenous compounds. In one mode of operation, it may be desired to fill a large fermentation vessel with a culture medium including all of the nutrients required and all of the carbohydrate, sufficient both for biomass production and for the production of the desired product. The vessel can be operated under conditions such that biomass production is promoted initially, for example, by providing aerobic conditions, and then switched to anaerobic conditions for the production of the desired product in an alternate mode of operation, a smaller vessel is used for biomass production, with a high level of nutrients and sufficient carbohydrate to produce, for example, about 100 g/L biomass. The contents of this vessel can then be transferred to a larger vessel, containing a second culture media that contains less nutrients, for example, only glucose as a carbon source or other carbohydrate carbon source in water. This vessel may be operate under anaerobic conditions for the production of the desired organic product. Biomass growth is reduced due to the reduced level of nutrients and the anaerobic conditions.

In a preferred embodiment, the nutrient media is kept to only the required materials in order to simplify recovery of the desired product. Use of aerobic growth can allow a simplified media to be used, relative to that needed if growth under anaerobic conditions was needed. Many of the yeast described herein can be grown, under aerobic conditions, on a media consisting only of sugar, an inorganic nitrogen source, trace minerals, and some vitamins. Before addition of organic product to the culture medium as a result of fermentation or other processes, the culture medium generally has a pH between about 5.0 and 7.0. However, as organic products such as organic acids are secreted into the culture medium by the microorganism, the pH of the culture medium tends to decrease. The term "organic pH" as used herein refers to the pH of the culture 20 medium attributed to organic compounds present in the medium such as carboxylates, for example, lactic acid. The term "inorganic pH" as used herein refers to the pH attributed to inorganic compounds such as HCl and $H_2SO_4$. The culture medium can have an organic pH value less than about 3.0 (e.g., less than about 2.9, 2.8, 2.7, 2.6, 2.5, 2.4, 2.3, 2.2, 2.1, 2.0, 1.9, 1.8, 1.7, 1.6, or 1.5), or an inorganic pH value less than about 3.0 (e.g., less than about 2.9, 2.8, 2.7, 2.6, 2.5, 2.4, 2.3, 2.2, 2.1, 2.0, 1.9, 1.8, 1.7, 1.6, or 1.5). Any carbon source can be used during the culturing procedure. For example, medium containing a pentose carbon (e.g., ribose, arabinose, xylose, and lyxose) can be used. In addition, medium containing a corn fiber hydrolysate can be used. A corn fiber hydrolysate can have a pH value between 2.0 and 6.5. Typically, a corn fiber hydrolysate contains glucose, xylose, and arabinose. For example, a corn fiber hydrolysate can contain about 40 grams/L glucose, about 40 grams/L xylose, and about 20 grams/L arabinose. For large-scale production processes, the following methods can be used. First, a large tank (e.g., a 50-, 100-, 200-, or more gallon tank) containing appropriate culture medium with, for example, hexose and/or pentose carbons is inoculated with a particular microorganism. After inoculation, the culture conditions can be manipulated such that the carbon source is used predominately to produce biomass. For example, the culture medium can be manipulated to have a pH value of about 7.0, a temperature of about 35° C., and a dissolved oxygen content that creates an aerobic environment throughout the tank. It is noted that the desired organic product can be produced during this biomass production phase. Once a sufficient biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose and arabinose, while the second tank contains medium with glucose.

Once transferred, the culture conditions within the second tank can be manipulated such that the carbon source is used predominately to produce organic product wherein "organic product" includes, among other things, pyruvate-derived products and carbon dioxide ($CO_2$) but does not includes biomass (i.e., cell dry weight). As used herein, the phrase "predominately produce a "selected organic product" or a "selected pyruvate-derived product" when referring to a culture conditions, means that the carbon source within the culture medium is metabolized, typically by a fermentation process (although not necessarily), to form at least 0.5 grains organic product per gram carbon source consumed (e.g., at least 0.6, 0.75 or 0.8 grains organic product). Methods for determining the amount of organic product produced and/or carbon source consumed are known and include, for example, HPLC.

As described earlier, the efficiency of carbon source utilization may vary depending on the substrate and organism. Thus, while a complex growth media which includes carbon sources other than carbohydrate (e.g., amino acids) may be used, the amount of organic product or pyruvate-derived product produced per gram carbon source refers only to the amount of organic product or pyruvate-derived product produced per gram carbohydrate carbon source consumed. Preferably, at this stage, no more than 0.3 grams biomass per gram carbon source is produced (e.g., no more than 0.2, 0.1, or 0.05 grams biomass). For example, the culture medium can be manipulated to have a dissolved oxygen content that creates an anaerobic environment throughout the tank, or to contain an inhibitor of cellular respiration. In addition, the culture medium can be manipulated such that a particular pH value (e.g., an acidic, neutral, or basic pH 10 value) is maintained. Alternatively, the pH of the culture can be adjusted periodically without maintaining any particular pH value. Typically, when producing an organic acid, the pH value of the culture medium is maintained above at least about 1.5 (e.g., at least about 2.0, 2.5, 3.0, 3.5, 4.0, 4.5, 5.0, 5.5, 6.0, 6.5, or 7.0). Further, as the microorganism catabolizes the provided carbon sources, the temperature within the tank will increase. Thus, the culture medium can be manipulated such that a particular temperature is maintained. Alternatively, the temperature of the culture medium can he adjusted periodically without maintaining any particular temperature. Typically, a temperature less than about 35° C. (e.g., less than about 34, 33, 32, 31, or 30° C.) is maintained when using heat sensitive microorganisms, while a temperature less than about 45° C. (e.g., less than about 44, 43, 42, 41, 40, 39, 38, 37, 36, or 35° C.) is maintained when using heat insensitive microorganisms. It is noted that biomass can be produced during this organic product production phase. In addition, the culture conditions within the second tank can be switched from those that promote product production to those that promote biomass production, and vice versa, one or more times. For example, the culture conditions within the second tank can be anaerobic the majority of the time with brief pulses of dissolved oxygen such that aerobic conditions periodically exist.

In another method, the anaerobic culture conditions may be modified to increase the metabolic energy of the cultured microorganism, for example, by the addition of a terminal electron acceptor. As used herein, the term "metabolic energy" refers to the energy (in terms of ATP) derived by the organism from an energy source (such as a carbon source). Under some conditions, the amount of metabolic energy obtained by the organism from the metabolism of a carbon source is greater than the amount of energy obtained from the same carbon source under different conditions.

Living cells are highly ordered and must create order within themselves in order to survive and grow. To maintain order within the organism, thousands of different chemical reactions are occurring within the organism at any instant in time. For example, cells need energy for biosynthetic reactions such as DNA, RNA and protein polymerization reactions and formation of metabolic products. Cells also need energy to bring substrates into the cell, keep metabolites within the cell, maintain a proper turgor pressure and internal pH, and for motility. Because energy cannot be created or destroyed, the cell requires an. input of energy from the environment to maintain the order. Energy is generally supplied from the environment in the form of electromagnetic radiation or chemical energy. The energy obtained from the environment is harnessed by the cell used by one of two general biochemical mechanisms: substrate level phosphorylation and electron transport. Generally, under anaerobic conditions, ATP (the "cellular currency' for energy) is produced by substrate level phosphorylation. In substrate level phosphorylation, energy is released from chemical bonds and is stored mainly in the form of ATP. An example of substrate level formation is the conversion of glucose to pyruvate through glycolysis:

Glucose=2 Pyruvate+2 *ATP*+2 $H_2$

Pyruvate can be then be converted into lactic acid:

Pyruvate+2 $H_2$=Lactate

The net energy produced by the above transformation is equivalent to 2 ATP.

Pyruvate can be further processed to tricarboxylic acid (TCA) cycle and generate additional energy and hydrogen atoms:

Pyruvate-3$H_2$O=3$CO_2$+*ATP*+5$H_2$

The net reaction for glucose respiration:

Glucose+6$H_2$O=6$CO_2$-4*ATP*+12$H_2$

Thus, by substrate level phosphorylation, the complete respiration of glucose to $CO_2$ will provide a net energy equivalent of 4 ATP and 24 hydrogen atoms. In "electron transport", the oxidation-reduction potentials of the compounds that constitute members of an "electron transport chain" are poised such that each member can be reduced by the reduced form of the preceding member. Thus, reducing power, as electrons, can flow through the chain of carrier molecules to a terminal electron acceptor such as oxygen ($O_2$), nitrate (NO3), and fumarate. Addition of a terminal electron acceptor such as oxygen, nitrate or fumarate to a culture medium can provide the microorganism with increased metabolic energy (e.g., increased ATP production for the same amount of carbon source consumed).

Oxygen is the most preferred terminal electron acceptor. For example, if oxygen is used as a terminal electron acceptor, hydrogen can be processed through the electron transport chain and provide the cell with an additional 1.5 ATP per hydrogen atom and 3 ATP per oxygen atom. Generally, the amount of metabolic energy can be determined by measuring the ratio of the amount of oxygen consumed to the amount of glucose consumed. Table 1 presents expected maximum and minimum improvements of energy yield (moles ATP per moles glucose) when oxygen is added during production as a function of the product yield which is decreasing due to loss of pyruvate to TCA cycle (and, consequently to respiration). Maximum % improvement was calculated assuming a P/O ratio of 3 whereas minimum % improvement assumed a P/O ratio of 0.5. Table 2 shows the estimated maximum amount oxygen consumed per mole glucose consumed. Addition of oxygen can promote minimal growth that will sequester carbon to biosynthesis leaving a small amount of carbon available for respiration (and, therefore, oxygen utilization).

TABLE 1

| Product Yield (g-lactate/g-glucose) | Maximum % improvement in energy yield | Minimum % improvement in energy yield |
|---|---|---|
| 1.0 | 0% | 0% |
| 0.9 | 160% | 35% |
| 0.8 | 320% | 70% |
| 0.7 | 480% | 105% |
| 0.6 | 640% | 140% |
| 0.5 | 800% | 175% |
| 0.4 | 960% | 210% |
| 0.3 | 1120% | 245% |
| 0.2 | 1280% | 280% |
| 0.1 | 1440% | 315% |
| 0.0 | 1600% | 350% |

TABLE 2

| Product Yield (g-lactate/g-glucose) | mole oxygen per mole glucose |
|---|---|
| 1.0 | 0.0 |
| 0.9 | 0.6 |
| 0.8 | 1.1 |
| 0.7 | 1.6 |
| 0.6 | 2.1 |
| 0.5 | 2.6 |
| 0.4 | 3.1 |
| 0.3 | 3.6 |
| 0.2 | 4.1 |
| 0.1 | 4.6 |
| 0.0 | 5.1 |

Thus, to improve the metabolic energy of the microorganisms in the cell culture, oxygen can be added to the cell culture as a terminal electron acceptor. Whereas the maximum molar yield of lactic acid from glucose is 2 mole lactate per mole glucose and the molar yield of ATP from glucose is 2 mole ATP per mole glucose, addition of oxygen as a terminal electron acceptor allows some of the pyruvate to be channeled to the citric acid (TCA) cycle where it is converted to $CO_2$ and energy. Thus, supplying a terminal electron acceptor "increases the metabolic energy' of the microorganism.

Diverting pyruvate to the TCA cycle will tend to reduce the amount of other pyruvate-derived products (such as lactic acid) produced. For example, a 10% reduction in yield may result in the generation of 2.6 times more metabolic energy for the microorganism, a 20% reduction in yield may result in the generation of 4.2–5 times more metabolic energy for the microorganism, and a 50% reduction in yield may result in the generation of 9 times more metabolic energy for the microorganism.

It is anticipated that in the later stages of a process, when high levels of metabolic products such as lactic acid are present, that the cell may require more metabolic energy to maintain function.

Thus, it may be desirable to expose the microorganisms within an anaerobic culture medium to brief pulses of dissolved oxygen. Preferably, the brief pulse of dissolved oxygen' results in the culture medium having a dissolved oxygen concentration of no greater than 0.5 percent, preferably between about 0.1 and 0.5 percent. Alternately, the growth rate or cellular maintenance of the microorganisms during anaerobic fermentation can be increased by the addition of other terminal electron acceptors such as nitrate or fumarate. The oxygen is added at a level just sufficient to increase the metabolic energy of the microorganism while maintaining productivity at a desired level. Care must be used to avoid excessive yield loss. This technique may also be used to help consume residual sugars and thereby to further simplify recovery processes.

6. Organic Product Purification Methods

Once produced, any method can be used to isolate the desired product. For example, common separation techniques can be used to remove the biomass from the broth, and common isolation procedures (e.g., extraction, distillation, and ion-exchange procedures) can be used to obtain the organic product from the microorganism-free broth. See, U.S. Pat. No. 4,275,234; U.S. Pat. No. 5,510,526; U.S. Pat. No. 5,831,122; U.S. Pat. No. 5,641,406; and International Patent Application Number WO 93/00440. In addition, the desired organic product can be isolated while it is being produced, or it can be isolated from the broth after the product production phase has been terminated. It is important to note that the culture conditions within the second tank can be manipulated such that the isolation process is improved. For example, the pH and temperature within the second tank can be manipulated such that the desired organic product precipitates out of solution, or is in a form more amenable to isolation. Specifically, the pH value of organic acids can precipitate out of solution when the pH of the broth is less than the pKa value for the organic acid. For example, the culture conditions while producing glutamic acid can be such that the pH is less than 2.19, which is the pKa value for glutamic acid. Thus, manipulating the pH, temperature, and content of the broth can facilitate organic product isolation. In addition, particular genetically manipulated yeast can be selected and/or specific culture conditions can be manipulated such that any byproducts within the broth are such that they do not interfere with the recovery of the desired organic product.

It will be appreciated that the methods and materials described herein can be adapted and used in any type of culturing process including, without limitation, the processes commonly referred to as "continuous fermentation" and "batch fermentation" processes. In addition, the microorganisms used during one production process can be recovered and reused in subsequent production processes. For example, the microorganisms can be reused multiple times to produce a desired organic product. Further, any carbon source can be used. For example, allose, altrose, glucose, mannose, gulose, iodose, galactose, talose, melibiose, sucrose, fructose, raffinose, stachyose, ribose, arabinose, xylose, lyxose, starches such as corn starch and wheat starch, and hydrolysates such as corn fiber hydrolysates and other cellulosic hydrolysates can be used as a carbon source for the production of either biomass or the desired organic product. Moreover, any medium can be used. For example, standard culture media (e.g., yeast minimal medium and YP medium (yeast extract 10 g/L, peptone broth 20 g/L)) as well as media such as corn steep water and corn steep liquor can be used. A significant advantage of the present invention is that the preferred microorganisms, especially when grow In under aerobic conditions, can utilize minimal media. The anaerobic production typically will not require additional nutrients, so the final product can be isolated from a relatively clean fermentation broth using any of a variety of separation techniques. Liquid-liquid extraction is a well-known technique for the separation of organic acids from fermentation broths, and results in considerable purification. With the present invention it is believed that simpler, less costly, less energy-consuming systems may also be useful.

In one embodiment, the present invention uses genetically modified yeast having a crabtree-negative phenotype in a train-type process that induces a "switch" in the metabolic pathway after a critical cell density has been reached and at which time it is desired to dramatically increase the specific productivity of the desired organic product. A typical method for inducing the metabolic pathway switch is by moving the biomass from a highly aerated vessel to a substantially anaerobic vessel, causing oxygen starvation. It is noted that a common carbohydrate (e.g., glucose or xylose) can be used as the carbon source during both the growth phase and the production phase. The use of a genetically modified yeast cell having a crabtree-negative phenotype can be critical to the success of this embodiment. In addition, the specific productivity of the desired organic product can be critical to success. The term "specific productivity" as used herein reflects the amount of product produced and is represented as the number of grams of organic product produced per gram of biomass (dry weight) per hour, i.e., g/(g*hour). Typically, the specific productivity for organic products such as lactate and acrylate is greater than about 0.1 g/(g * hour), for example, greater than about 0.2 g/(g * hour), or greater than about 0.5 g/(g * hour). By providing a high specific productivity as described herein, the energy required for cell maintenance may be obtained via the fermentative product pathway under substantially anaerobic conditions, rather than relying on aeration to generate high amounts of energy via the respiratory pathway.

It is noted that substantially anaerobic vessels are aerated at a rate of less than about 0.1 VVM. Under certain production situations, no aeration will be used. In addition, the yield (i. e., g organic product/g carbon source consumed) in this embodiment typically is greater than about 70 wt %, and is produced without the addition of carbon sources such as ethanol and acetate. In some cases, in order to achieve the specific productivity required to generate the required energy for cell maintenance, it may be necessary to enhance the pathway from glucose to pyruvate in addition to providing the necessary enzymes to produce the desired product.

In another embodiment, the train-type process can be designed such that only the highly aerated growth vessel is equipped with sterilization capability. The anaerobic production vessel is typically operated at temperatures greater than about 35° C. (e.g., greater than about 36, 37, 38, 39, 40, 41, 42, 43, 44, or 45° C.). Few wild-type yeast will be able to survive and compete with the genetically modified yeast at such temperatures as the pH drops during product production, especially since they will not have an enhanced fermentation pathway that can generate energy for cell maintenance, in addition, the yeast can be engineered to contain "killer plasmids" as described herein, which can prevent yeast from other species from surviving. The invention also provides various methods for culturing yeast cells. For example, a yeast cell having a crabtree-negative phenotype can be cultured with culture medium either having an organic ph value less than about 3.0, or containing a corn fiber hydrolysate. Other methods for culturing yeast cells include, without limitation, culturing yeast cells having a crabtree-negative phenotype at a temperature greater than about 35° C. with culture medium either having an inorganic pH value less than about 3.0, or containing a pentose carbon or corn fiber hydrolysate.

Further, the invention provides a process for making an organic product. This process includes growing a microorganism under culture conditions, and changing the culture conditions to promote production of the organic product. In this process, the microorganism has reduced pyruvate decarboxylase, alcohol dehydrogenase, aldehyde dehydrogenase, and/or acetyl-CoA synthase activity, and exhibits a growth rate in the absence of ethanol and acetate that is at least about 30 percent (e.g., about 35, 40, 50, 75, 100, 150, 200 percent, or more) of that observed in a corresponding microorganism not having reduced pyruvate decarboxylase, alcohol dehydrogenase, aldehyde dehydrogenase, and/or acetyl-CoA synthase activity. Typically, culture conditions that promote cellular respiration are used in situations where rapid growth is needed, or where the organic product to be produced cannot be produced without cellular respiration, while culture conditions that reduce cellular respiration are used in situations where rapid growth is not needed, or where the organic product to be produced can be produced without cellular respiration.

The invention will be further described in the following examples, which do not limit the scope of the invention described in the claims.

EXAMPLES

Example 1

Figure 2:
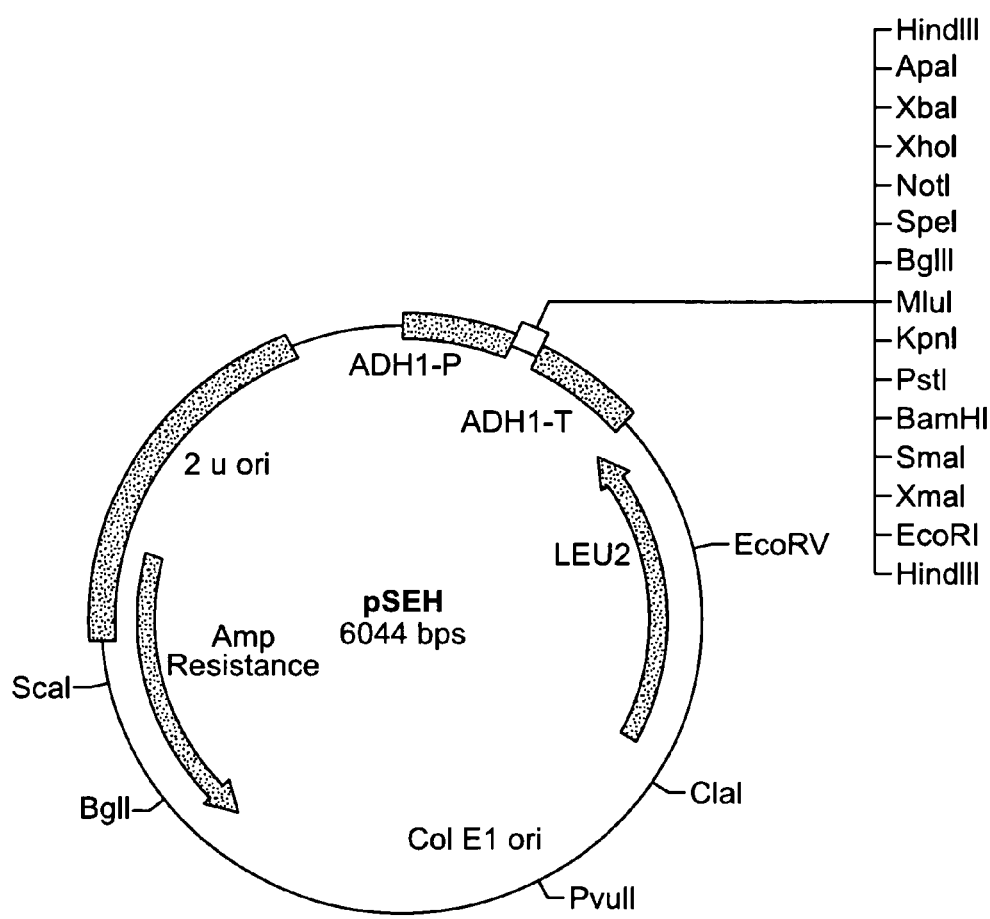
FIG. 2 is a diagram depicting the pSEH plasmid.

Recombinant Plasmid pHES/pSEH 0.5 ug of plasmid pGAD424 described by Chien et al. (*Proc. Natl Acad. Sci.*, 88:9578–9582 (1991)) was digested with the restriction enzyme HindIII. The digested mixture was separated by gel electrophoresis on a 0.8% agarose gel using TBE buffer. A 5.9 kbp fragment was then purified from the gel as described in Sambrook et al., (ibid.). A complementary pair of 92 bp synthetic oligomers with multiple restriction enzyme recognition sites was designed. The first was designated fwd HES oligo and has the following sequence:
5'-CCCAAGCTTGAATTCCCCGGGGGATC-CCTGCAGGGTACCACGCGTAGA TCTACTAGT-GCGGCCGCCTCGAGTCTAGAGGGC-CCAAGCTTGGG-3' (SEQ ID NO: 1). The second was designated camp hes oligo and has the following sequence:
5'-CCAAGCTTGGGCCCTCTAGACTCGAG-GCGGCCGCACTAGTAGATCTAC GCGTGGTAC-CCTGCAGGGATCCCCCGGGGAAT-TCAAGCTTGGG-3' (SEQ ID NO:2). 500 nmoles of the two complementary oligomers were annealed to each other by boiling for ten minutes and cooling gradually to room temperature. The double stranded 92 bp DNA was digested with HindIII and ligated to the HindIII digested 5.9 kbp pGAD424. The ligation mixture was used to transform *E. coli* DH10B (electromax cells, Life Technologies, Rockville, Md.) by electroporation as described in Sambrook et al. (ibid.). Recombinant *E. coli* was plated on Luria-Bertani broth plates, and cells containing plasmid were selected using 100 µg/mL of the antibiotic ampicillin. The plasmid DNA from ampicillin resistant *E. coli* clones were screened to obtain the two plasmids pHES and pSEH (FIGS. 1 and 2). The two plasmids differ in the orientation of the synthetic oligomer with respect to the alcohol dehydrogenase—ADHI promoter on the vector.

Example 2

PCR Amplification of Nucleic Acid Encoding Lactate Dehydrogenase from *Lactobacillus helveticus* and *Pediococcus acidilactici*

Genomic DNA was isolated from overnight cultures of *Lactobacillus helveticus* (ATCC 10797) and *Pediococcus acidilactici* (ATCC 25741) using PUREGENE® genomic DNA isolation kit (Gentra systems, Minneapolis, Minn.). PCR primers were designed to isolate lactate dehydrogenase-encoding nucleic acid from *L. helveticus* (lh-ldh oligos) and *P. acidilactici* (pa-ldh oligos) genomic DNA. These primers were designed based on the available gene sequences for lactate dehydrogenases in the Genbank databases, and have the following sequences:
5' lh-ldh, 5'-CCGGGATCCATGGCAAGAGAG-GAAAAACCTC-3' (SEQ ID NO:3);
3' lh-ldh, 5-CCAAGATCTTTATTGACGAACCT-TAACGCCAG-3' (SEQ ID NO:4);
5' pa-ldh:
5'-CCGGGATCCATGTCTAATATTCAAAAT-CATCAAAAAG-3' (SEQ ID NO:5); and
3' pa-ldh, 5'-CCAAGATCTTTATTTGTCT-TGTTTTTCAGCAAG-3' (SEQ ID NO:6). The primers were optimized using Primer Designer software obtained from Sci-ed software (Durham, N.C.). One umole of the genomic DNA was used along with 100 nmoles of primers. Pfu DNA polymerase (New England Biolabs) was used to PCR amplify lactate dehydrogenase (LDH) nucleic acid as described in Sambrook et al. (ibid.).

A similar strategy is employed to isolate L-lactate dehydrogenase-encoding nucleic acid from genomic DNA from microorganisms such as *Bacillus* sp., for example, *Bacillus megaterium* (ATCC 6458) or *Rhizopus oryzae* (ATCC 76275) or any other lactate producing organism (including microorganisms such as fungi and bacteria and multicellular organisms such mammals) or from tissue from a lactate producing organism. Genomic DNA is isolated from a growing culture of the organism using PUREGENE® genomic DNA isolation kit (Gentra systems, Minneapolis, Minn.). Suitable PCR primers are designed to isolate the lactate dehydrogenase-encoding nucleic acid based on the LDH gene sequences for these species available from Genbank. Generally, one µmole of the genomic DNA is used along with 100 nmoles of the appropriate primers. Pfu DNA polymerase (New England Biolabs) or any other suitable DNA polymerase is used to amplify lactate dehydrogenase (LDH) nucleic acid from the respective genomic DNA using PCR technology, for example, as described in Sambrook et al. (ibid.).

Alternately, lactate dehydrogenase-encoding nucleic acid is isolated from *Kluyveromyces thermotolerans* (ATCC 52709), *Trichoderma reesci* (ATCC 13631), *Torulaspora pretoriensis* (ATCC 36245), or any other lactate dehydrogenase producing organism using the any of the following methodologies.

1) A genomic cDNA library from one of these organisms is cloned into an standard *E. coli* expression vector such as pUC19 using standard techniques (Sambrook et at. (ibid.). An. *E. coli* (ldh pfi) mutant strain NZNI 11 (Bunch et al., (1997) "The ldhA gene encoding the fermentative lactate dehydrogenase of *Escherichia coli,*" *Microbiology*, 143: 187–95) is transformed with this library and the cells are grown under anaerobic conditions in M9 medium supplemented with casamino acid. Any *E. coli.* that grows under these conditions encodes either a lactate dehydrogenase or is a revertant in ldh or pfl. Positives (colonies that form under the anaerobic growth conditions) are screened for LDH activity using a calorimetric assay of lactic-acid specific soft-agar overlay (LASSO) that is capable of differentiating between (L)-LDH and (D)-LDH (Witte et al., 1989, *Basic Microbiol.* 29:707–716 (1989)). Plasmid DNA from clones suspected of expressing l-lactate dehydrogenase are then isolated and sequenced.

2) *K. thermotolerans* ATCC 52709, *T reesei* ATCC 13631 and *Torulaspora pretoriensis* ATCC 36245 are all eukaryotes that produce L-lactic acid when cultured under anaerobic conditions (Wine et al. (*Basic Microbiol.* 29:707–716 (1989)), Thus, according to this method, at least one of these strains is grown under anaerobic conditions to induce lactate dehydrogenase enzyme activity. cell free extracts is then obtained using standard methods and subjected to known protein purification strategies to isolate the lactate dehydrogenase enzyme. Methods for purifying lactate dehydrogenase are known (Kelly et al., (1978), Affinity chromatography of bacterial lactate dehydrogenases," *Biochem J.*, 171: 543–7). After the protein is purified, it is partially cleaved and sequenced to determine the amino acid sequence. This amino acid sequence is then used to design degenerate primers to isolate the gene encoding lactate dehydrogenase from the genomic DNA.

An eukaryotic LDH, such as the one isolated from *K. thermotolerans* or *Trichoderma reesei* or *Torulaspora pretoriensis*, may function better (in terms of 15 transcriptional efficiency, translational efficiency and/or protein activity) in the yeast *K. marxianus* compared to an LDH from bacterial sources such as *Bacillus* or *Lactobacillus*.

3) Using the known eukaryotic lactate dehydrogenase gene sequences available from Genbank, degenerate primers are designed to isolate the gene for lactate dehydrogenase from genomic DNA of *K. thermotolerans* ATCC 52709, *T. reesei* ATCC 13631 or *Torulospora pretoriensis* ATCC 36245. The conserved NAD+ binding site and pyruvate binding site among LDH gene sequences is used to design degenerate primers. One µmole of genomic DNA is used along with 100 nmoles of primers. Pfu DNA polymerase (New England Biolabs), or any other suitable DNA polymerase, is used to amplify fragments of the L-lactate dehydrogenase (LDH) nucleic acid according to known PCR methods, for example, those described in Sambrook et al. (ibid.).

Example 3

Cloning of *L. helveticus* and *P. acidilactici* LDH Genes into pCRII Vector

Figure 3:
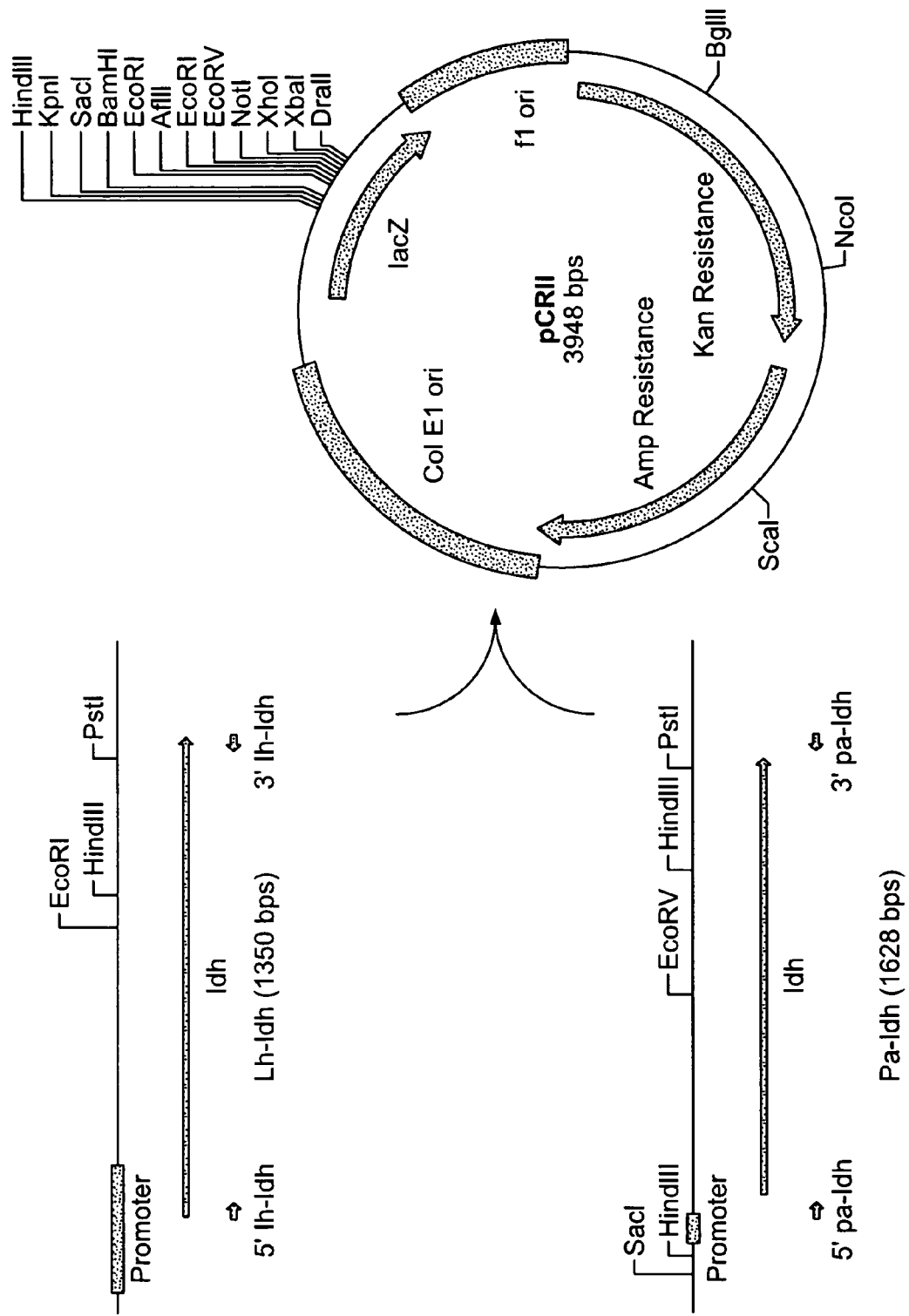
FIG. 3 is a diagram depicting the generation of pCRII plasmids containing either Lh-LDH or Pa-LDH.
Figure 4:
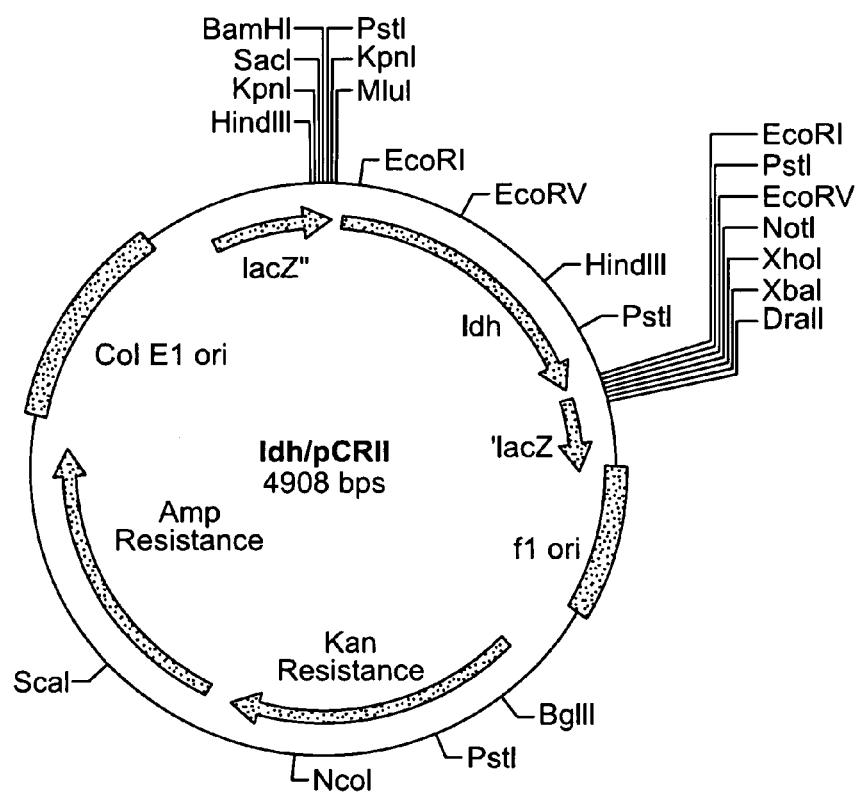
FIG. 4 is a diagram depicting the LDH/pCRII plasmids.

PCR amplified LDH DNA products were ligated with pCRII vectors (FIGS. 3 and 4) using the TA cloning kit obtained from Invitrogen (Carlsbad, Calif.). The ligation mixture was then used to transform *E. coli* DH1OB using methods described in Sambrook et al. (ibid.). The pCRII vectors supplied with the kit allowed for quick cloning of the PCR products according the manufacture's instructions. The pCRII vectors with the LDH genes from *L. helveticus* and *P. acidilactici* are depicted in FIG. 4.

Example 4

Figure 5:
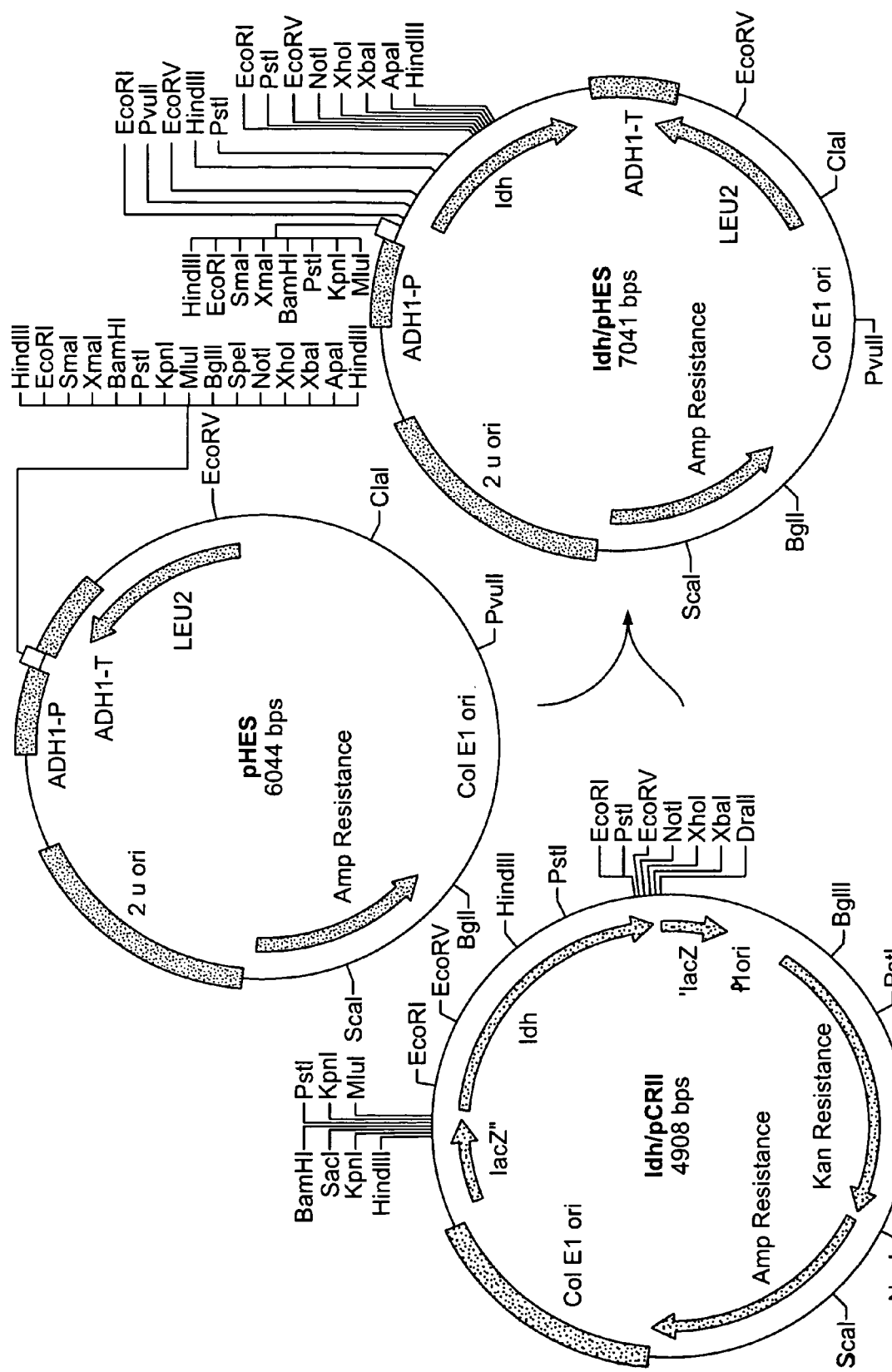
FIG. 5 is a diagram depicting the generation of pHES plasmids containing Lh-LDH or Pa-LDH.

Recombinant Plasmid pLh ldh-HES/pPa ldh-HES Having *L. helveticus* and *P. acidilactici* LDH Genes in pHES Vector The pCRII vectors containing LDH gene from *L. helveticus* and *P. acidilactici* were digested with the appropriate restriction endonucleases. The pHES vector was similarly digested with the same restriction endonucleases. A 1 kbp insert containing LDH from pCRII vectors was then ligated to the 6.0 kbp pHES vector using T4 DNA ligase as described in Sambrook et al. (ibid.). The ligation mixture was used to transform *E. coli* DH1OB (electromax cells, Life Technologies, Rockville, Md.), and recombinant clones were selected for ampicillin resistance. DNA isolated from recombinant clones was analyzed to confirm the pLh ldh-HES and pPa ldh-HES vectors (FIG. 5). These vectors contain the genes encoding LDH from *L. helveticus* and *P. acidilactici* in the pHES vector under the control of the yeast alcohol dehydrogenase promoter (ADH1).

Example 5

Cloning of *Bacillus* sp., *Rhizopus oryzae*, *K thermotolerans*, *Trichoderma reesei* or *Torulaspora pretoriensis* LDH Gene for Expression Using the *Saccharomyces* PDC1 Gene Promoter Although it is possible to use the lactate dehydrogenase promoter found in *Rhizopus oryzae*, *K thermotolerans*, *Trichoderma reesei* or *Torulaspora pretoriensis* to control expression of a lactate dehydrogenase gene cloned in *K. marxianus*, the PDC1 promoter from *Saccharomyces cerevisiae* may be used to control expression of the isolated lactate dehydrogenase gene. *Saccharomyces cerevisiae* glycolytic promoters have been successfully used to express genes in *Kluyveromyces* strains. (Gellissen and Hollenberg, (1997) "Application of yeasts in gene expression studies: a comparison of *Saccharomyces cerevisiae*, *Hansenula polymorpha* and *Kluyveromyces lactis*—a review," *Gene*, 190: 87–97).

Figure 14:
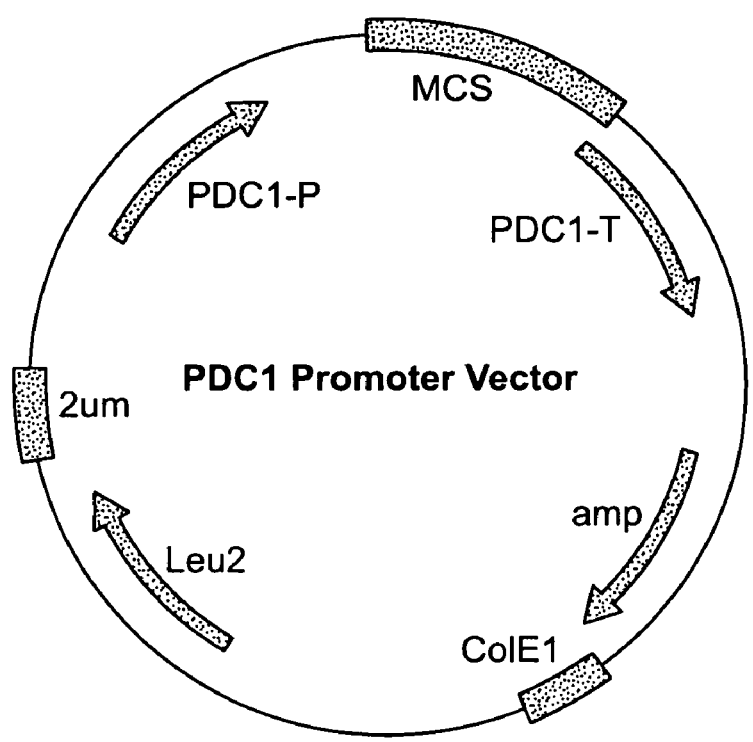
FIG. 14 is a plasmid map of PDCI promoter vector.

Accordingly, the PDC1 promoter from *Saccharomyces cerevisiae* is obtained by designing suitable oligomeric primers using the *Saccharomyces cerevisiae* genome sequence, available in Genbank. The PDC1 gene sequence and 1 Kb regions surrounding the PDC1 gene are amplified by PCR technologies. The resulting 4 Kb DNA fragment contains both the promoter and terminators that control PDCI gene expression. Multiple restriction enzyme sites are included between the promoter and terminators that control the PDCI gene expression such that a variety of LDH genes can be inserted under the control of the PDCI promoter and terminators. The 4 Kb DNA fragment is inserted into a suitable vector, such as a pUC 19 based *Saccharomyces cerevisiae* or *E. coli* shuttle vector. The LDH gene is then introduced into the vector at one of the multiple cloning sites under the control of the promoter and terminators such that lactate dehydrogenase gene expression is controlled by the PDC1 promoter and terminator. (FIG. 14).

Alternately, other *Saccharomyces* glycolytic promoters such as those that control the expression of the *Saccharomyces cerevisiae* glyceraldehyde-3 phosphate dehydrogenase or the phosphoglycerate kinase genes may be used similarly to express the cloned LDH gene in *K marxianus*.

Example 6

Amplification of Linear Fragments of Homologous DNA for Gene Disruptions of Pyruvate Decarboxylase An 82 bp oligomeric primer (5'kmPDC1Ko) was designed to contain 51 bp identical to the 5' end of the pyruvate decarboxylase (PDC) from *K. marxianus* and 30 bp identical to the 5' end of the ADH1 promoter from pHES vectors. The sequence of 5'KmPDC1Ko is as follows:
5'-TAAACAGTACAATCGCAAAGAAAAGCTC-CACACCCAAACCAAATAA TTGCAATGCAACT-TCTTTTCTTTTTTTTTCTTTTCT-3' (SEQ ID NO: 7). The sequence for the PDC genes from yeasts (*K. marxianus* or *Y. stipitis* or *H. polymorpha*) was obtained from the submitted Genbank sequence. Similarly, a reverse 79 bp oligomer (3'kmPDC1Ko) was designed to contain 54 bp that were identical to the 3' end of the PDC gene and 22 bp that were identical to the 3' end of the ADHI terminator. The sequence of 3'kmPDC1Ko is as follows:
5'-TTATAAAATCATTAAAATCCAAAATCG-TAATTTATCTCTTTATCCTC TCCCTCTCTACATGC-CGGTAGAGGTGTGGTCA-3' (SEQ ID NO:8).

The primers were designed to amplify a linear DNA fragment from the pLh-ldh-HES and pPa-ldh-HES plasmids wherein the fragment contained the entire lactate dehydrogenase gene along with the ADH1 promoter and terminator (FIG. 6). The PCR amplified product also contains ends that were homologous to sequences from either *K. marxianus* PDC1, *Yamadazyma stipitis* PDC1 and PDC2, and *Hansenula polymorpha* PDCI and PDC2. The amplification reaction was performed using Pfu DNA polymerase (New England Biolabs; Beverly, Mass.). 100 ng of pLh-ldh-HES or 5 pPa-ldh-HES was used in the reaction along with 5 units of polymerase and 100 nmoles of the oligomers. The reaction was carried out according to protocols described in Sambrook et al. (ibid.). FIG. 6 depicts the final linear product with the described homologies.

Alternate constructs were prepared to improve the likelihood of obtaining a pdc negative strain of *K. marxianus*. To prepare these constructs, a 5.5 kbp fragment surrounding the *K. marxianus* 1.7 kbp PDC1 gene was isolated (FIG. 6*b*) using PCR and genome walking techniques (Clonetech). The 5.5 kbp fragment was then cloned into the pCRII TA cloning vector (Invitrogen) using standard methods. A portion of approximately 370 bp near the middle of the 1.7 kbp coding region of PDCI was removed from the *K. marxianus* 5.5 kbp fragment by restriction digestion (Sambrook et al., ibid.). The removed fragment has the following sequence:
CCGGTTCTTTCTCTTACTCTTACAAGAC-CAAGAACATTGTCGAATTCCAC TCCGACTACAT-CAAGGTCAGAAACGCCACTTTCCAGGT-GTCCAAATGA AGTTCGTCTTGCAAAAGTTGTTGAC-CAAGGTCAAGGATGCTGCTAAGGG TTACAAGC-CAGTTCCAGTTCCTCACGCTCCAAGAGA-CAACAAGCCAGTT GCTGACTCTACTCCATTGAAGCAA-GAATGGGTCTGGACTCAAGTCGGTA AGTTCCTA-CAAGAAGGTGATGTTGTTCTAACT-GAAACCGGTACCTCCGCT TTCGGTATCAACCAAACCCACTTC-CCAAATGACACCTACGGTATCTCCA AGTCT-TGTGGGGTTCCATTGGTTTCA (Sequence ID No. 10).

A kanamycin resistance gene and its promoter was then isolated from a pPIC9K vector (Invitrogen) using standard restriction technology (See Sambrook et al.), and cloned into the site in the 5.5 kbp from which above-identified fragment was removed. The pPIC9K (Invitrogen) kanamycin resistance gene and its promoter were inserted such that the sequence of the inserted region was as follows:
GTACAACTTGAGCAAGTTGTCGAT-CAGCTCCTCAAATTGGTCCTCTGTAA CGGAT-GACTCAACTTGCACATTAACTTGAAGCT-CAGTCGATTGAGTGAAC TTGATCAGGTTGTGCAGCTGGTCAGCAG-CATAGGGAAACACGGCTTTTCC TACCAAACT-CAAGGAATTATCAAACTCTGCAACACT-TGCGTATGCAGGT AGCAAGGGAAATGTCATACTTGAAGTCG-GACAGTGAGTGTAGTCTTGAG AAATTCTGAAGC-CGTATTTTTATTATCAGTGAGTCAGT-CATCAGGAGATC CTCTACGCCGGACGCATCGTGGCCGAC-CTGCAGGGGGGGGGGGGCGCT GAGGTCTGC-CTCGTGAAGAAGGTGTTGCTGACTCAT-ACCAGGCCTGAAT CGCCCCATCATCCAGCCAGAAAGTGAGG-GAGCCACGGTTGATGAGAGCT TGTTGTAGGTG-GACCAGTTGGT-GATTTTGAACTTTTGCTTTGCCACGGA ACGGTCTGCGTTGTCGGGAAGATGCGT-GATCTGATCCTTCAACTCAGCAA AAGTTCGATT-TATTCAACAAAGCCGCCGTCCCGT-CAAGTCAGCGTAATGC TCTGCCAGTGTTACAACCAATTAAC-CAATTCTGATTAGAAAAACTCATCG AGCAT-CAAATGAAACTGCAATTTATTCATAT-CAGGATTATCAATACCATA TTTTTGAAAAAGCCGTTTCTGTAAT-GAAGGAGAAAACTCACCGAGGCAG TTCCATAG-GATGGCAAGATCCTGGTATCGGTCTGC-GATTCCGACTCGTCC AACATCAATACAACCTTTAATTTC-CCTCGTCAAAAATAAGGTTATCAA GTGAGAAATCACCATGAGTGACGACT-GAATCCGGTGAGAATGGCAAAAGC TTATGCAT-TCTTTCCAGACTTGTTCAACAGGCCAGC-CATTACGCTCGT CATCAAAATCACTCGCATCAACCAAAC-CGTTATTCATTCGTGATTGCGCC TGAGCGAGAC-GAAATACGCGATCGCTGTTAAAAGGA-CAATTACAAACAG GAATCGAATGCAACCGGCGCAGGAA-CACTGCCAGCGCATCAACAATATT TTCACCT-GAATCAGGATATTCTTCTAATACCTG-GAATGCTGTTTTCCCGGG GATCGCAGTGGTGAGTAACCATGCAT-CATCAGGAGTACGGATAAAATG CTTGATGGTCG-GAAGAGGCATAAATTCCGTCAGCCAGTT-TAGTCTGACCA TCTCATCTGTAACATCATTGGCAACGC-TACCTTTGCCATGTTTCAGAAAC AACTCTGGCG-CATCGGGCTTCCCATACAATCGATAGAT-TGTCGCACCTGA TTGCCCGACATTATCGCGAGCCCATT-TATACCCATATAAATCAGCATCCA TGTTGGAATT-TAATCGCGGCCTCGAGCAAGACGTTTC-CCGTTGAATATGG CTCATAACACCCCTTGTATTACTGTT-TATGTAAGCAGACAGTTTTATTGTT CATGAT-GATATATTTTTATCTTGTGCAATGTAA-CATCAGAGATTTTGAGA CACAACGTGGCTTTCCCCCCCCCCCTG-CAGGTCGGCATCACCGGCGCCA CAGGTGCGGT-TGCTGGCGCCTATATCGCCGACATCAC-CGATGGGGAAGA TCGGGCTCGCCACTTCGGGCTCAT-GAGCGCTTGTTTCGGCGTGGGTATGG TGGCAG-GCCCGTGGCCGGGGGACTGTTGGGCGC-CATCTCCTTGCATG (Sequence ID No. 9).

Figure 6A:
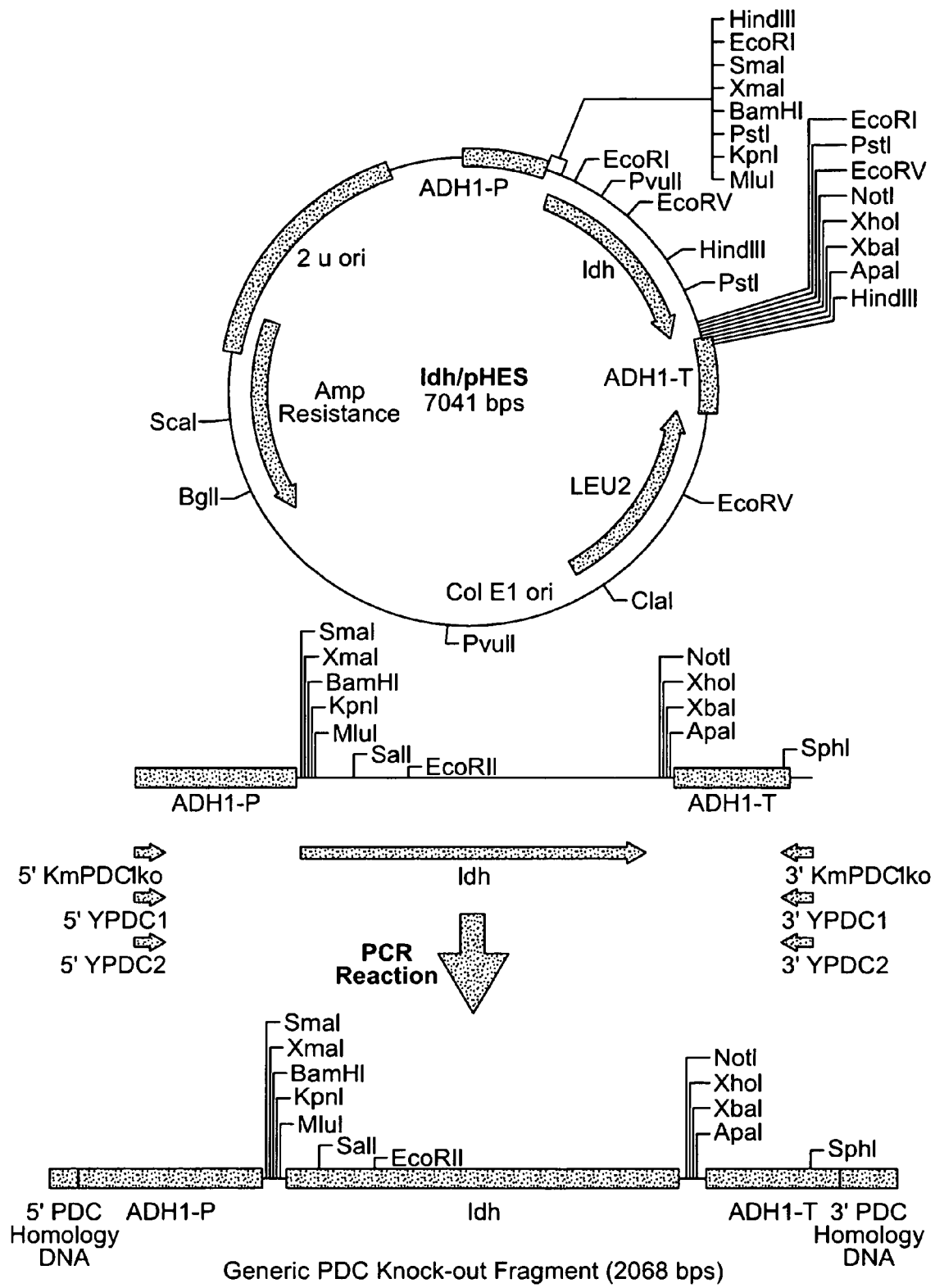
FIG. 6a is a diagram depicting the generation of pyruvate decarboxylase (PDC) knockout fragment
Figure 6B:
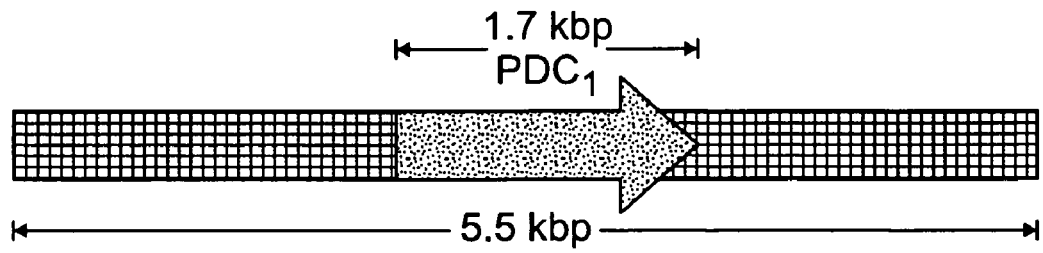
FIG. 6b is a diagram depicting the 5.5 kbp fragment surrounding the K marxianus 1.7 kbp PDC1.
Figure 6C:
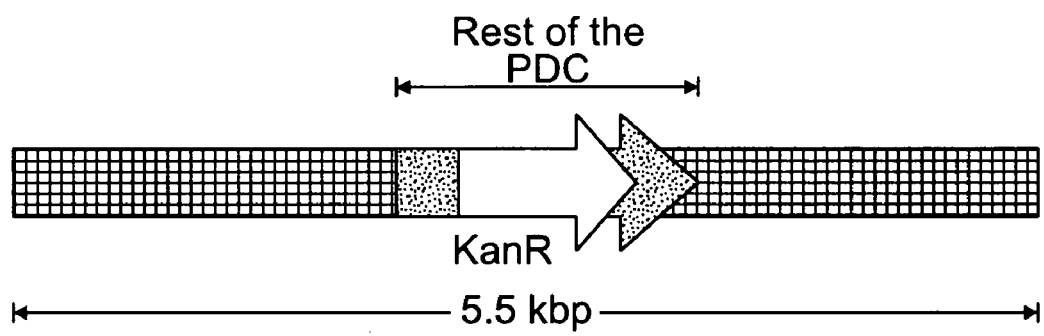
FIG. 6c is a diagram depicting the deletion of 400 bp of the 5.5 kbp PDC homologous region and the insertion of a gene for kanamycin resistance.
Figure 6D:
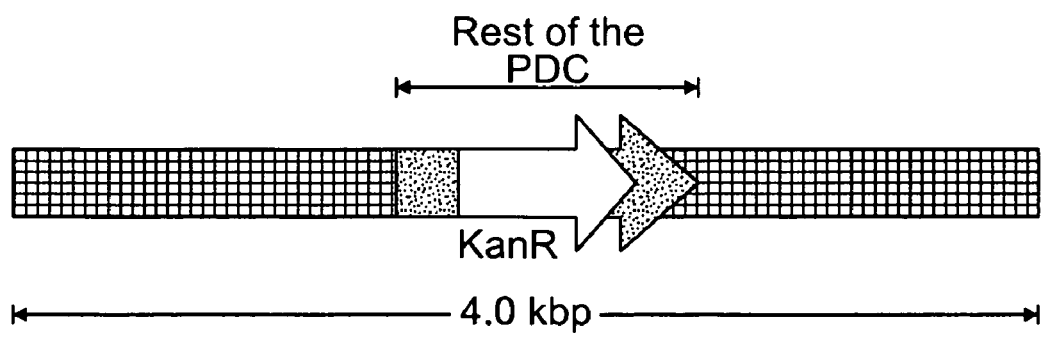
FIG. 6d is a diagram depicting the 4 kb region containing the kanamycin resistance gene and the surrounding 2.3 kbp of the PDC1.
Figure 6E:
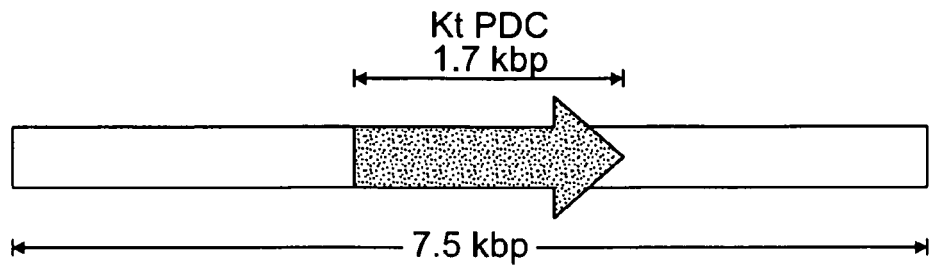
FIG. 6e is a diagram depicting the 7.5 kbp K. thermotolerans PDC1 and surrounding region.

The resulting construct contains the G418 resistance gene surrounded by approximately 5 kbp of the pdc region as shown in FIG. 6c. A similar DNA construct was made which contained the internal G418 gene surrounded by 2.3 kbp of K. marxianus PDC1 in the pCRII vector as shown in FIG. 6d.

Example 7

Use of Linear DNA Fragment to Disrupt the Endogenous PDC Coding Sequence and Insert an LDH Coding Sequence Simultaneously The linear DNA fragment generated by PCR described in Example 5 is used to transform K. marxianus, Yamadazyma stipitis, or Hansenula polymorpha. The protocol used for transformation is as described by Wesolowski-Louvel et al. (NONCONVENTIONAL YEASTS IN BIOTECHNOLOGY: KLUYVEROMYCES LACTIS, ed. Klaus Wolf, Springer Verlag, Berlin, p. 138–201 (1996)). Briefly, 5 mL of an overnight culture is spun down and washed with electroporation buffer (10 nM Tris-HCl, 270 nM sucrose, 1 nM $MgCl_2$, pH 7.5). The washed cells then are incubated for 30 minutes at 30° C. in incubation buffer (5 g/L yeast extract, 10 g/L peptone broth, 10 g/L glucose, 25 nM DTT, 20 nM HEPES, pH 8.0). At the end of this period, the cells are washed again and resuspended in 400 uL incubation buffer. DNA (200 ng) is added to these cells, and the cells are pulsed using the Bio-Rad Gene Pulser at 1800 volts, 1000 Cl, and 25 µF in a 0.4 cm cuvette.

The cells are plated on regular YPD (10 g/L yeast extract, 20 g/L peptone broth, 20g/L glucose, 15% agar plates, and colonies are allowed to regenerate over 72 hours. Each of the plates with colonies are replica plated on fresh YPD plates and incubated for 48 hours. The colonies then are overlayed with 6.5% soft agar (0.5% agar in 300 mM Tris-HCl, 187 mM glutamate, pH 8.3). A staining mixture (3.2 mL of 1% agar, 1.6 mL of 120 mM Tris, 75 mM glutamate, pH 8.3, 0.4 mL of 2 mg/mL phenazine methosulfate, 7 units of glutamate pyruvate transaminase, and 7 units of L(+)-pig muscle lactate dehydrogenase) is added to the overlayed plates.

Yeast strains with high L(+) form blue halos within 10–120 minutes. This method is similar to the method suggested by Subden et al. (*Canadian J. Microbiol.*, 28:883–886 (1982)), and modified by Witte et al. (*J. Basic Microbial.* 29:707–716 (1989)). The colonies are selected, and the DNA isolated from the colonies is tested by PCR analysis and sequenced to detect the disrupted pyruvate decarboxylase gene.

In another embodiment, the clones described in Example 6 above and depicted in FIGS. 6c and 6d are digested with two restriction enzymes (see, Sambrook et al., ibid.) to yield approximately 3 micrograms of fragment DNA containing the homologous PDC region that includes the mid-sequence inserted kanamycin resistance gene. K. marxianus is transformed with the fragment using known techniques, such as electroporation, to disrupt the pdc of K. marxianus.

Generally, electroporation is performed as follows: a) grow a culture of the microorganism in YPAD overnight (~15 h) in a volume of 20 mL; b) transfer 500 uL from the culture to a microfuge tube, spin @4L 4 mm, discard supernatant; c) wash the pellet with 1 mL cold EB (EB=Electroporation Buffer: 10 mM Tris-HCl, pH 7.5; 270 mM Sucrose; 1 mM $MgCl_2$.); d) resuspend in 1 mL IB (IB=Incubation Buffer: YPD; 25 mM DTT; 20 mM HEPES, pH8.0.); e) shake @ 800 rpm, 30° C. for 30 min in an Eppendorf Thermomixer; f) spin down, wash once with EB, resuspend in 400 uL EB; g) add three micrograms fragment DNA (in water 10 mM Tris-Cl, pH 8.5), incubate on ice 30 mm; h) transfer to 0.4 cm electroporation cuvette. Bio-Rad Gene Pulser settings: 1000V, 1000 Cl, 50 TF. Time constant after pulse: ~20 msec; i) transfer to 3 mL Morton Closure tube, incubate without shaking at 30° C. for 1 hour. Add 400 uL liquid YPAD media (YPAD: 10 g Yeast Extract; 20 g Peptone; 20 g Glucose; 100 mg Adenine Hemisulphate. Volume=1 L. No pH adjustment), shake @ 800 rpm, 30° C. for 1 hour in Eppendorf Thermomixer. Add 400 uL liquid YPAD and recover 4–6 hours; j) spin down in microfuge tube 4K, 4 mm, discard supernatant, resuspend in 400 uL 1M Sorbitol; k) plate onto 200 ug/ml G418 selective plates; and 1) incubate at 30° C. for three to five days.

The colonies are screened first by a second patching onto 300 ug/ml G418. The genomic DNA is isolated from the secondary yeast patch by standard genomic preparations (Sambrook). These are then screened via PCR for 1) the presence of the kanamycin fragment using suitable primers and conditions (Sambrook) and 2) the absence of the disrupted pdc region using suitable primers and PCR conditions.

Colonies positive for the selection marker and negative for the pdc disruption region were then grown and analyzed by HPLC for physiology. Genomic DNA from those strains was further analyzed by southern hybridization analysis.

Example 8

Growth Characteristics of Cells

1. Low pH/high Temperature

Overnight cultures of K marxianus were inoculated into 50 mL yeast minimal medium according to Kiers et al. (*Yeast*, 14(5):459–469 (1998)). Glucose (100 g/L) was used as the carbon source. The overnight cultures were maintained at 40° C., and inoculated into medium that was also maintained at 40° C. Addition of the inoculant changed the pH of the medium from 5.5 to 2.5. During the experiment, the pH remained 2.5. Glucose concentration was measured by YSI-membrane, and optical density (OD) was measured using a spectrophotometer.

Figure 7:
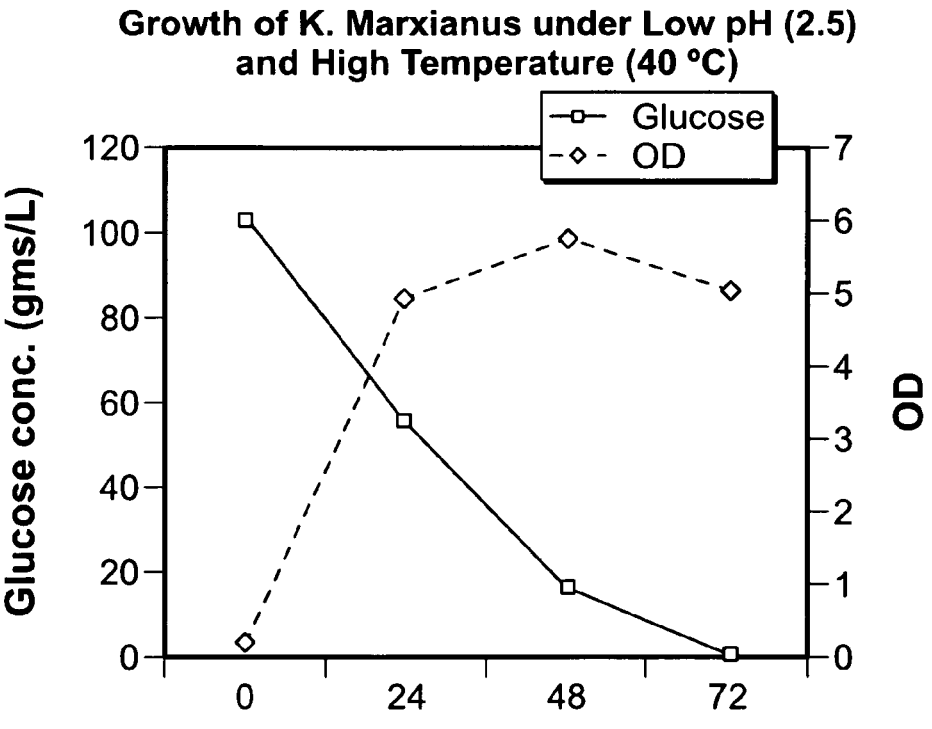
FIG. 7 is a graph plotting growth (optical density; OD) verses time (hours) for *Kluyveromyces marxianus* cultured under low pH (pH 2.5) and high temperature (40° C.) conditions.

Glucose was utilized in 72 hours, indicating that metabolic activity occurs under low pH and high temperature culture conditions during that time period (FIG. 7). In addition, biomass decreased slightly during the 48 to 72 time period, indicating that cell catabolism out paces anabolism (FIG. 7).

2. Pentose Carbon Sources

Overnight cultures of K. marxianus were inoculated into three 50 mL flasks containing yeast minimal medium according to Kiers et al. (*Yeast*, 14(5):459–469 1998)). Each of the three flasks contained a different carbon source. The first contained 10 percent glucose, the second contained 10 percent D-xylose, and the third contained 10 percent L-arabinose. The flasks were incubated at 30° C., and the OD measurements were made periodically.

Figure 8:
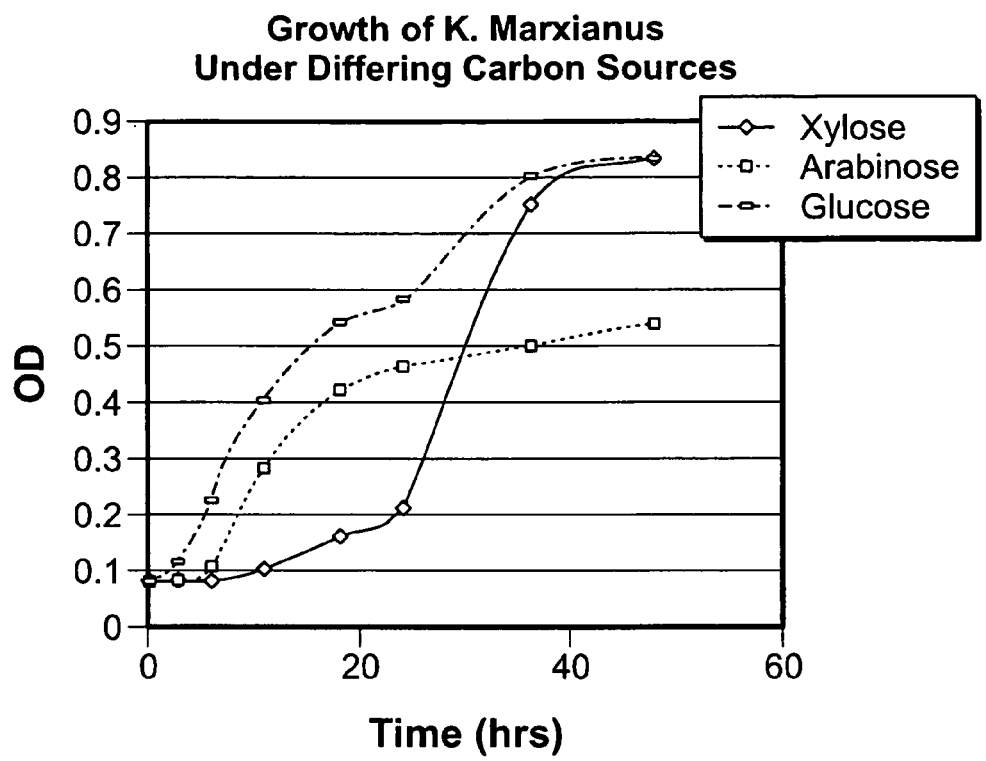
FIG. 8 is a graph plotting growth (OD) verses time (hours) for *K. marxianus* cultured with glucose, xylose, or arabinose at 30° C.

After 40 hours, the biomass yield for yeast cultured with glucose or xylose was similar, while the biomass yield for yeast cultured with arabinose was lower (FIG. 8). Comparing the growth of yeast cultured with glucose to those cultured with xylose or arabinose revealed an initial lag time in growth. The yeast cultured with arabinose exhibited a lag time of a few hours, while the lag time for yeast cultured with xylose was much more pronounced (FIG. 8). The presence of this lag tune indicates that the yeast cells need time to adapt to the xylose and arabinose carbon sources. Presumably, this time is needed to induce the synthesis of polypeptides not normally expressed.

3. Corn Fiber Hydrolysate at Low pH

Overnight cultures of *K. marxianus* were inoculated into flasks containing yeast minimal medium according to Kiers et al. (*Yeast*, 14(5):459–469 (1998)). Each flask contained 30% corn fiber hydrolysate as the carbon source. Briefly, the corn fiber hydrolysate was made by reacting corn fiber with 1.2% sulfuric acid at 145° C. for 25 minutes. During the reaction, the hemicellulose was broken down into the monomeric products arabinose, xylose, and glucose. Because of the high temperature during the reaction, some arabinose and xylose was degraded into furfural, while some glucose was degraded into hydroxymethlyfurfural. HPLC analysis of the hydrolysate revealed the presence of 38.7 grams/L glucose, 39.1 grams/L xylose, 20.7 grams/L arabinose, and 1.6 grams/L furfural. In addition, the hydrolysate had a pH of 1.51. Before culturing the yeast the pH of the corn fiber hydrolysate was adjusted to 3.0. During the culturing experiment, OD measurements were made periodically.

Figure 9:
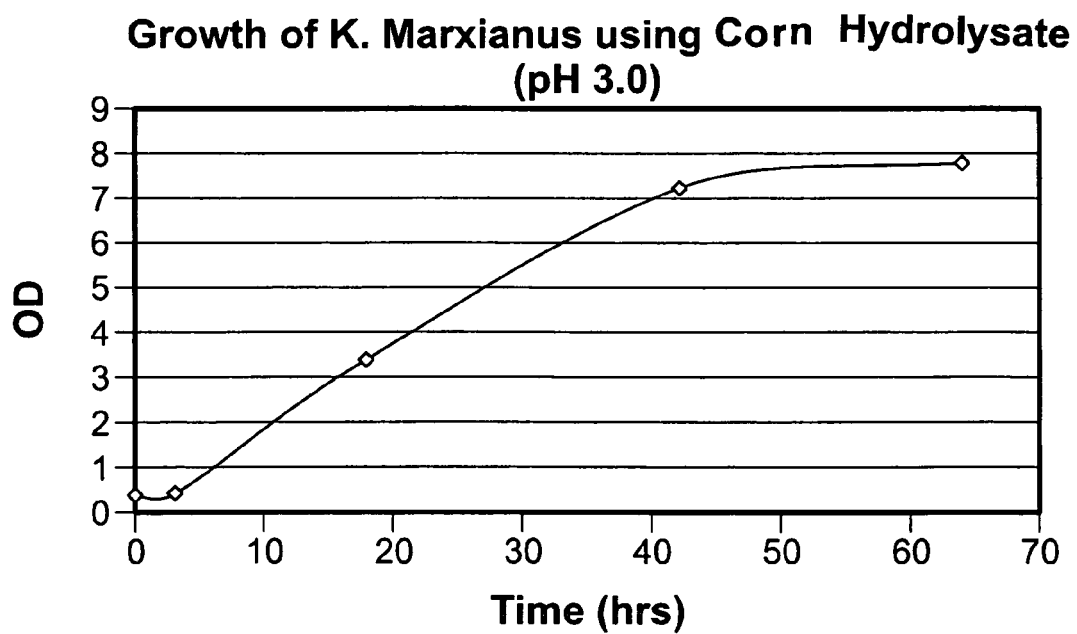
FIG. 9 is a graph plotting growth (OD) verses time (hours) for *K. marxianus* cultured with a corn fiber hydrolysate at 30° C.

The yeast cells were capable of generating biomass when cultured with corn fiber hydrolysate (FIG. 9).

4. Various pH Conditions

Figure 10:
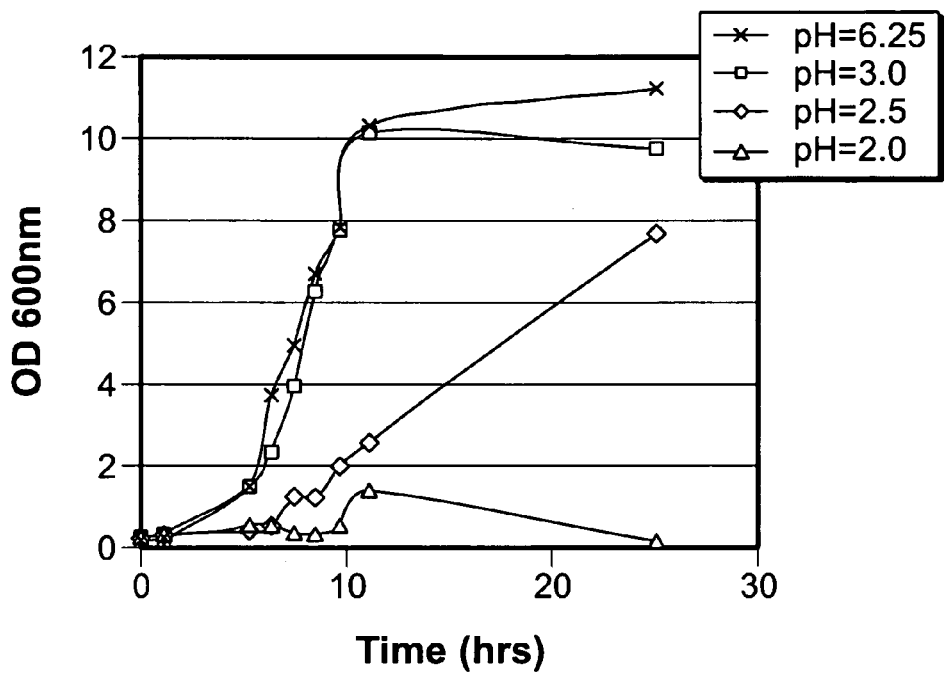
FIG. 10 is a graph plotting growth (OD) verses time (hours) for *K. marxianus* cultured at 30° C. and the indicated pH.

Overnight cultures of *K. marxianus* were inoculated into four flasks containing 50 mL yeast YPD medium (10 g/L yeast extract, 20 g/L peptone broth, 20 g/L glucose). Each flask had a different pH, which was adjusted using HCl. During the culturing experiment, the temperature was maintained at 30° C., and OD measurements were made periodically. Growth was observed within each flask (FIG. 10).

5. Various pH Conditions/Lactic Acid

Figure 11:
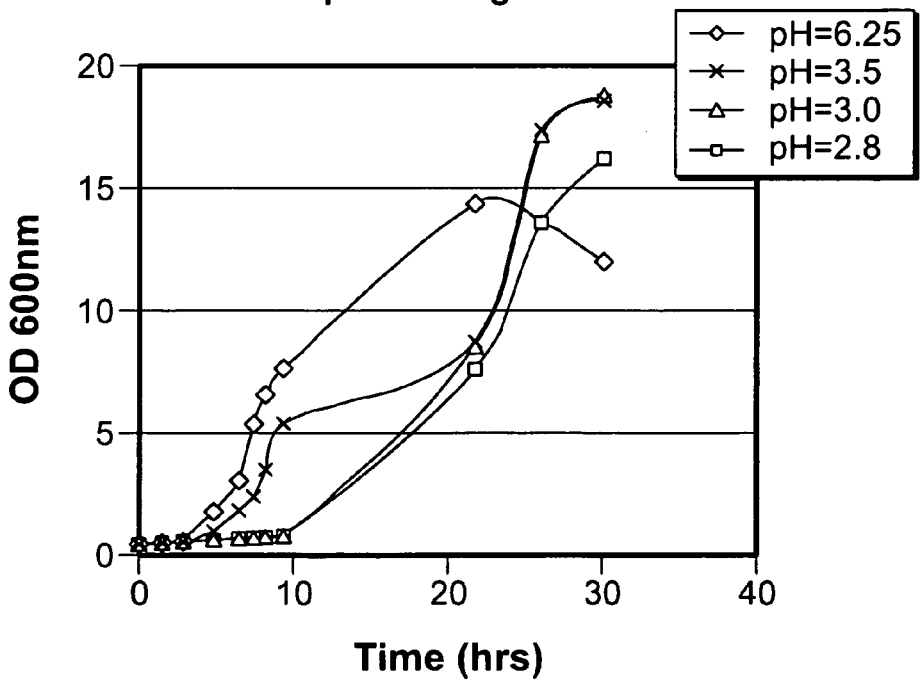
FIG. 11 is a graph plotting growth (OD) verses time (hours) for *K. marxianus* cultured at 30° C. and the indicated pH in the presence of 40 grams of lactic acid.
Figure 12A:
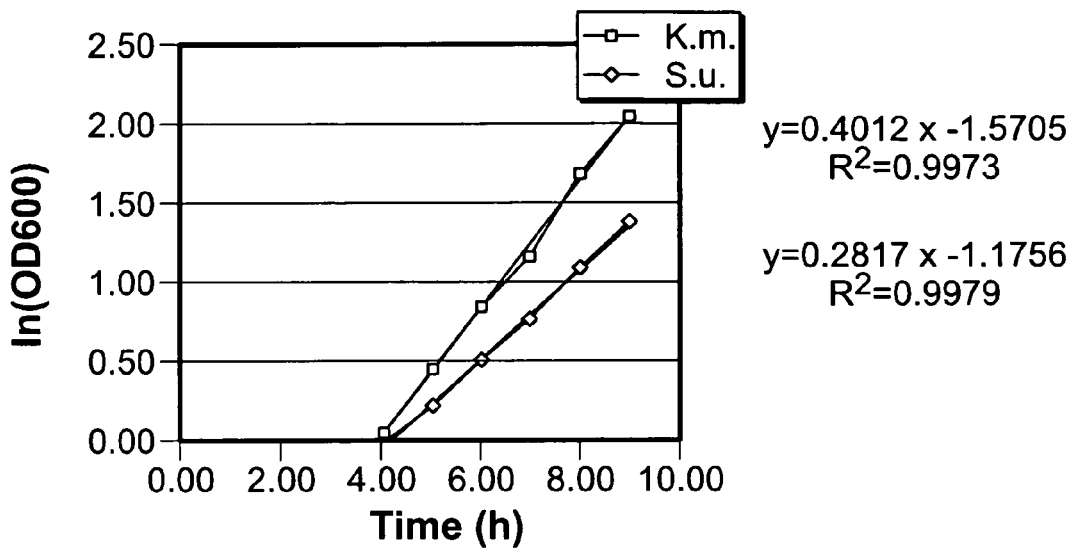
FIG. 12 shows three graphs plotting (A) biomass production; (B) glucose consumption; and (C) ethanol production of *S. uvarum* and *K. marxianus* when cultured on mineral medium with 2% glucose under aerobic conditions.
Figure 12B:
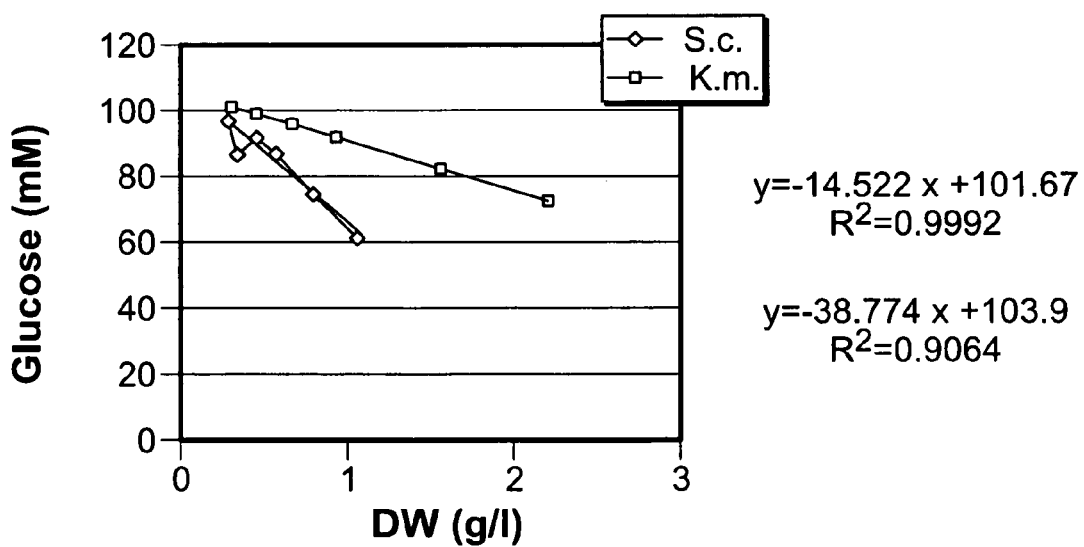
Figure 12C:
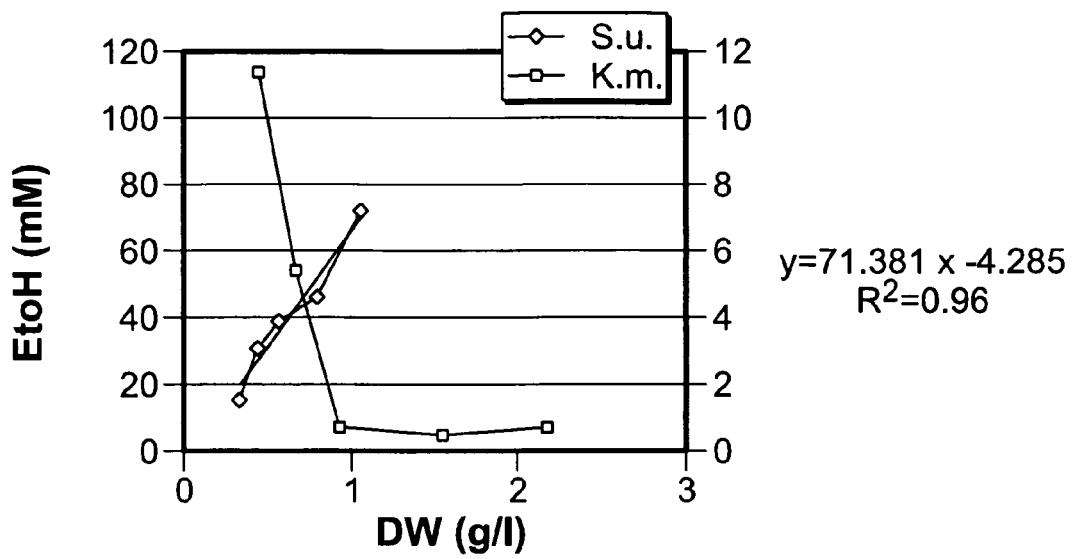
Figure 13A:
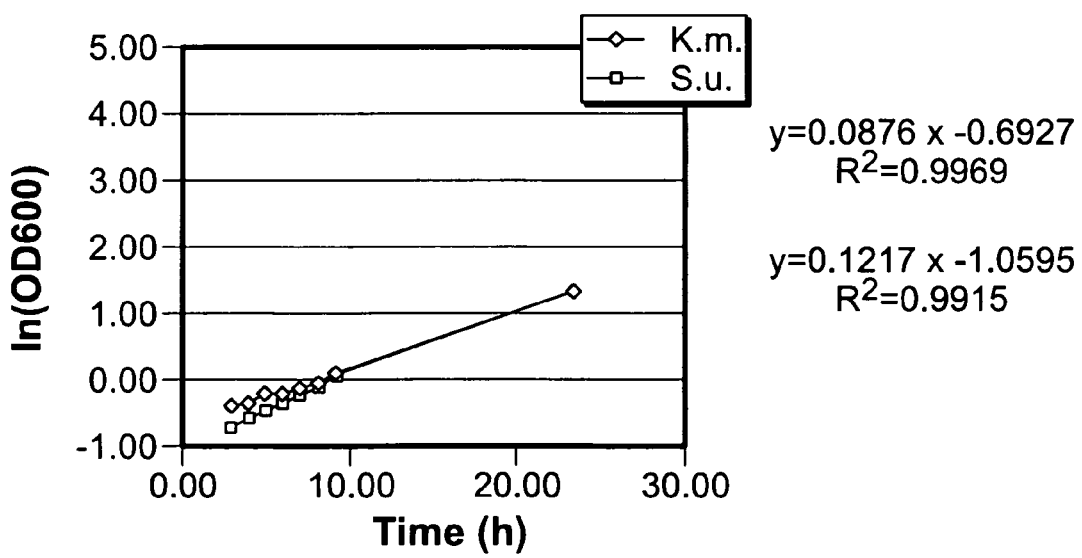
FIG. 13 shows three graphs plotting (A) biomass production; (B) glucose consumption; and (C) ethanol production of *S. uvarum* and *K. marxianus* when cultured on mineral medium with 2% glucose under anaerobic conditions.
Figure 13B:
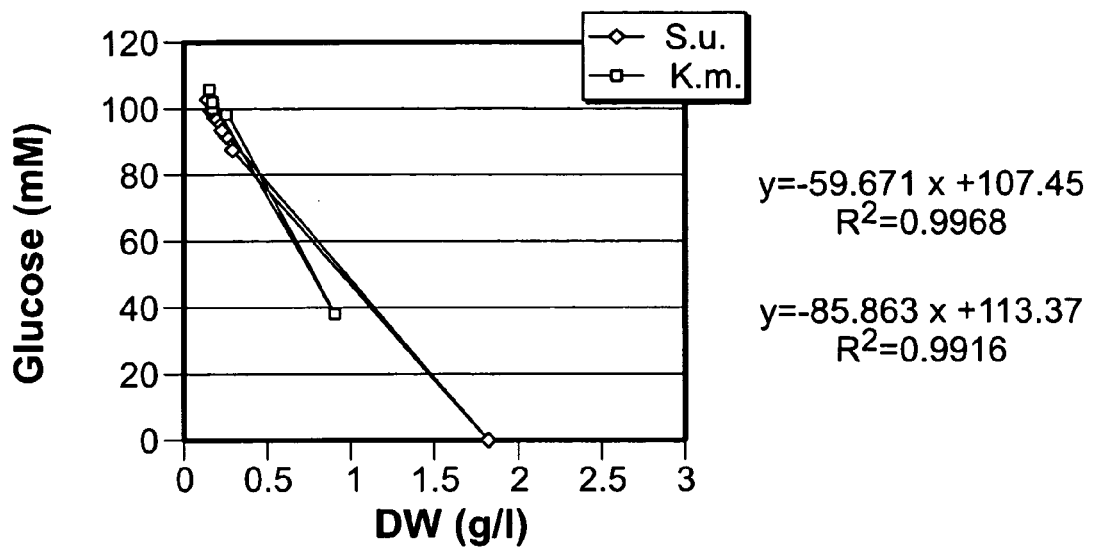
Figure 13C:
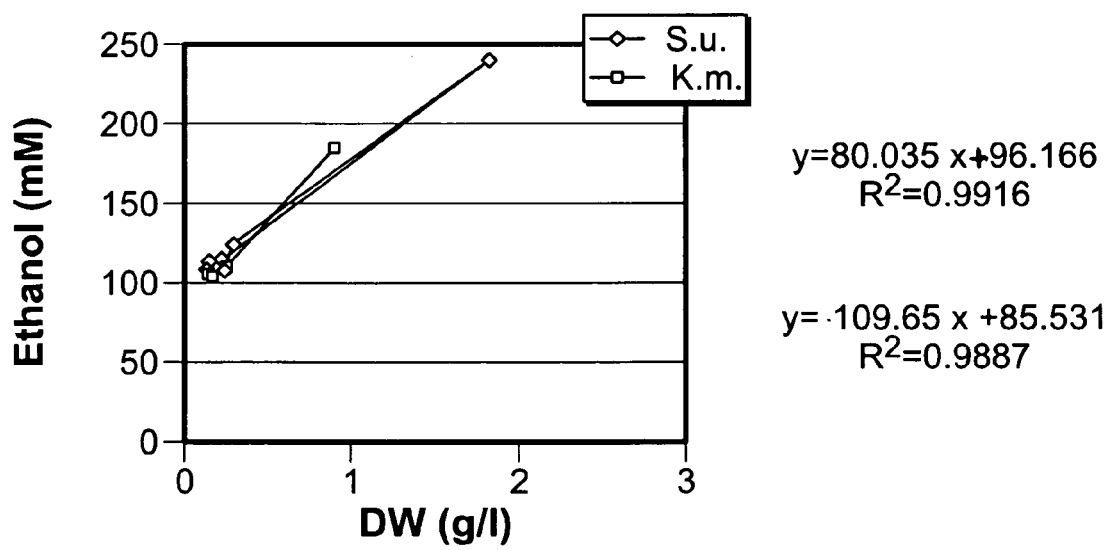

Overnight cultures of *K. marxianus* were inoculated into four flasks containing 50 mL yeast YPD medium (10 g/L yeast extract, 20 g/L peptone broth, 20 g/L glucose) as well as 40 g/L lactic acid. The addition of the lactic acid resulted in a pH of 2.8. Thus, the pH within three flasks was adjusted to the indicated pH using NaOH. During the culturing experiment, the temperature was maintained at 30° C., and OD measurements were made periodically. Growth was observed within each flask (FIG. 11).

Example 9

Recombinant Cells Capable of Producing acrylyl-CoA

An organism incapable of utilizing acrylate as a carbon source (e.g., *E. coil*) is transformed with a *Clostridium propionicum* genomic DNA library. The *C. propionicum* genomic library is generated using the pHES plasmid and expresses thereby 10 kbp fragments of the *C. propionicum* genome. The transformed *E. coil* are plated on selection media with acrylic acid as the only carbon source. Only those cells that have the ability to assimilate acrylate will grow. Acrylate is normally assimilated by its enzyme-mediated conversion into lactate. In turn, lactate can be converted into pyruvate and utilized by the cells via the Krebs cycle.

Once a transformed *E. coil* is selected, the DNA plasmid from the genomic library is isolated, and the inserted fragment sequenced. Once sequenced, the fragment is scanned for open reading frames to determine the coding sequence for enzymes involved in the conversion between lactate and acrylate (e.g., lactoyl-CoA dehydrogenase and CoA transferases).

The isolated clones containing the coding sequence for these enzymes is introduced into the yeast cells described in Example 6, which contain lactate dehydrogenase and lack pyruvate decarboxylase activity. Selection of recombinant yeast cells that contain the introduced nucleic acid is performed using G418 (300 g/L). Once isolated, the recombinant yeast cells are grown aerobically on glucose, and then switched to anaerobic conditions. The broth then is collected and assayed to acrylate using standard HPLC methods as described by Danner et al. (Biotechnological production of acrylic acid from biomass, In: *Applied Biochemistry and Biotechnology*, Vol. 70–72 (1998)).

Example 10

Recombinant Cells Capable of Producing Ascorbate

Expression vectors are engineered such that the following polypeptides are expressed: 2,5-dioxovalerate dehydrogenase, 5-dehydro-4-deoxy-D-glucarate dehydratase, glucarate dehydratase, aldehyde dehydratase, glucuronolactone reductase, and L-gluonolactone oxidase. The nucleic acid sequence encoding these polypeptides are isolated from various microorganisms. Once engineered, the expression vectors are transformed into a yeast cells by electroporation. Once transformed, the yeast cells are analyzed to determine whether or not they produce L-ascorbate.

Example 11

Recombinant Cells Capable of Producing D-xylose

Expression vectors are engineered such that the following polypeptides are expressed: 2-dehydro-3-deoxy-D-pentanoate aldolase, xylonate dehydratase, xylonotactonase, and D-xylose dehydrogenase. The nucleic acid sequences encoding these polypeptides are isolated from *Pseudomonas* spp. Once engineered, the expression vectors are transformed into yeast cells by electroporation. Once transformed, the yeast cells are analyzed to determine whether or not they produce D-xylose or other pentose carbon compounds.

Example 12

Recombinant Cells Capable of Producing Citrate

PCR primers are designed based on the *S. cerevisiae* aconitase (ACOI, Genbank accession number M33 13 t) nucleic acid sequence. These primers are used to clone the aconitase encoding nucleic acid from a *Kluyveromyces, Yamadazyma,* or *Hansenula* species. Once sequenced, linear constructs are made as described in Example 5, and used to disrupt the aconitase encoding nucleic acid within yeast cells. The selection marker used is the antibiotic G418 instead of lactate production as described in Example 5. The nucleic acid providing resistance to antibiotic G418 is the neomycin/kanamycin gene. This gene is obtained from the pPIC9K vector (InVitrogen), and inserted into the pHES vector. Yeast cells are transformed with PCR generated linear fragments that are engineered to have ends homologous to the ACO1 as described above. The linear fragment is designed to encode the G418 resistance gene. Only cells that have integrated the linear fragment in the location of the aconitase encoding nucleic acid are resistant to the antibiotic. Those cells are analyzed for the appropriate integration using PCR. The yeast cells obtained by this method have a partially functional TCA cycle, and thus can overproduce citrate.

The citrate is transported across the mitochondrial membrane and into the broth. In addition, these yeast cells are given an exogenous nucleic acid molecule that encodes an enzyme such as ATP-citrate lyase such that they can catalyze the conversion of accumulated citrate into oxaloacetate (see Example 13).

Example 13

Recombinant Cells Capable of Expressing Citrate Lyase in the Cytosol

A crabtree positive yeast cell is transformed with the pHES plasmid containing a nucleic acid sequence that encodes a polypeptide having ATP-citrate lyase activity. This nucleic acid is isolated from *E. coil, Krebsiella pneumoniae* (Genbank accession number X798 17), or other published sources. Once transformed, the yeast cells are analyzed to determine whether or not they can utilize sugars to produce large amounts of lipid accumulation. In addition, the yeast cells are analyzed to determine whether or not they exhibit ATP-citrate lyase activity as described by Holdsworth et al. (*J. Gen. Microbiol.*, 134:2907–2915(1998)). The yeast cells having ATP-citrate lyase activity are capable of providing cytosolic acetate under aerobic conditions by a route other than the breakdown of aldehyde to acetate via aldehyde dehydrogenase. In addition, when such yeast lack pyruvate decarboxylase or aldehyde dehydrogenase activity, they should be able to provide acetate for biosynthesis via the Krebs cycle.

Example 14

Recombinant Cells Unable to Utilize Lactate as Carbon Source

Yeast cells are engineered such that the activity of a carboxylic acid transporter similar to the *S. cerevisiae* JENI polypeptide is reduced. Such yeast cells will have a reduced ability to transport lactate, and hence utilize lactate less efficiently. The activity of the carboxylic acid transporter within yeast cells is reduced by disrupting the locus containing the coding sequence for this polypeptide. First, the homologue of the JEN1 polypeptide is isolated from a host cell using degenerate primers designed based on the available sequence for JEN1 (Genbank accession number U24 155). Once the nucleic acid is isolated from the host cell, it is sequenced. Disruption of the coding sequence for this polypeptide is done using the procedures described in Example 11. Linear fragments are generated encoding homologous regions to the JEN1 sequence as well as the entire G418 resistance gene. This linear fragment is integrated into the JEN1 genomic sequence causing disruption of the activity. Cells lacking carboxylic acid transporter activity are identified by their inability to transport carboxylic acid, and hence their inability to grow when cultured on lactate.

In addition, cells are modified such that the activity of a functional equivalent of the *S. cerevisiae* cytochrome b2 polypeptide is reduced. The cytochrome b2 polypeptide enables *S. cerevisiae* cells to metabolize lactate within the mitochondria. First, degenerate primers are -designed from the *Saccharomyces* cytochrome b2 sequence (Genbank accession number Z46729). Once isolated, the clone is sequenced. The disruption of the yeast host homologue of cytochrome b2 is done using methods described in Methods in Yeast Genetics (Eds. Alison et al., Cold Spring Harbor Press (1997)). This recombinant yeast cell will be unable to utilize lactate as a carbon source.

Example 15

Large-Scale Production of Lactate

Multiple variants of *K. marxianus* cells having reduced PDC activity are produced and isolated. Each variant is engineered to contain a different copy number of an exogenous nucleic acid molecule encoding a polypeptide having LDH activity. The LDH polypeptide is from multiple different sources. Such variant cells can have different specific productivity for lactic acid at 40° C.

Each variant is grown in a vessel under aerobic conditions with an air flow of 1.5 VVM and a dissolved oxygen content of 30% to reach a cell density of about 60 g/L, dry basis. Once the density is sufficient, the air flow is turned off, and the conditions within the vessel are switched to anaerobic conditions. No base is added.

The variants with the highest specific productivity during the anaerobic phase can be found not only to produce lactic acid faster, but also to achieve a higher concentration at a lower pH, than the variants with lower specific productivity.

Product yield on glucose during the production phase can exceed 90%. Certain variants are selected and subjected to the same culturing methods except that the air flow is reduced to 0.1 VVM, rather than being completely shut off Under such conditions, the final pH within the vessel can be lower, and the lactate concentration can be higher than the conditions with no air flow. Product yield on glucose can be reduced but can remain at about 90%. When the test is repeated, hut with an air flow of 0.5 VVM, the product yield on glucose can be reduced to less than 80%.

Example 16

Large-Scale Production of Lactate Using a Series of Batch Fermentations

A culture of *K. marxianus* lacking PDC activity and having LDH activity is used as the inoculum in a series of batch fermentations. Each fermentation is carried out in progressively larger vessels, each of which is sterilized immediately prior to use. In addition, each vessel is provided with an air flow of 1.5 VYM and stirring sufficient to maintain a dissolved oxygen content above 10%. The final vessel has a volume of 6,000 L. The vessels also are maintained at a temperature of 45° C. to enhance survival of the genetically modified *K. marxianus* cells over wild-type yeast and other microorganisms. Each vessel is filled with standard culture medium for optimal growth.

The contents of the final vessel, with a cell density of 100 grams of cells/L, dry basis, are transferred to a recently steamed production vessel having a volume of 300,000 L. Optionally, additional cells obtained from the filtration of a previous production process are added. The cell density in the production vessel is 6 grams of cells/L, dry basis. Glucose is added to a level of 80 g/L. The conditions within the vessel are anaerobic with the temperature being 42° C. for a period of 25 hours. The specific productivity is greater than 0.5 grams lactate/(gram biomass * hour) until near the end of the process, at which time the productivity begins to drop. Once productivity begins to drop, the cells are removed and saved for reuse. The final lactate concentration can be 75 g/L with the pH being 2.8. After biomass removal, the solution is concentrated by evaporation to a concentration of 50% lactate. The free acid (about 86% of total lactate) is extracted by liquid extraction into an organic and back extracted at a higher temperature into water. The raffinate containing the lactate salt is either cleaned and recycled as a buffer in the growth vessel, or acidified with, for example, sulfuric acid and purified.

Example 17

Comparison of Aerobic Production of a Crabtree Negative (*K. marxianus*) and a Crabtree Positive (*S. uvarum*) Organisms A crabtree negative (*K. marxianus*) and a crabtree positive (*S. uvarum*) organism were each grown in aerobic and anaerobic batch fermenters. Batch cultivation was performed at 30° C. in laboratory fermenters with a working volume of 1.5 L. The pH was maintained at 5.0±0.1 by automated addition of 2 mol/L potassium hydroxide (KOH). The fermentor was flushed with air (aerobic cultures) or nitrogen gas (anaerobic cultures) at a flow rate of 0.8 L/min and stirred at 800 rpm. The dissolved-oxygen concentration was continuously monitored with an oxygen electrode (Ingold, type 34 100 3002). in the aerobic cultures, the dissolved oxygen concentration was maintained above 60%. Ten mL samples were withdrawn at appropriate intervals for determination of dry weight and metabolite concentrations. Tween-80 and ergosterol were added to anaerobic cultures to supply the compounds required for fatty acid synthesis.

During exponential growth, both the dry weight and OD660 of yeast cultures, and the glucose and ethanol concentration in the supernatant were determined at appropriate intervals. The specific ethanol production rate ($q_{ethanol}$ mmol/g * h) was calculated by the following equation using linear regression analysis:

$$q_{ethanol} = (dE/dC_x) * \mu_{max}$$

where dE/dt (the rate of increase of the ethanol concentration in the culture; mmol/l 8 h) and $dC_x/dt$ (the rate of increase of the biomass concentration; g/l * h) were calculated using differentiation of plots of ethanol concentration and biomass concentration versus time, $\mu_{max}$ ($h^{-1}$). The maximum specific growth rate on glucose was estimated from the exponential part of a plot of $C_x$ versus time. To calculate the specific glucose consumption rate ($q_{glucose}$, mmol/g * h), dE was replaced by dG (the amount of glucose consumed per hour).

In the aerobic hatch cultures, the *Kluyveromyces* and the *Saccharomyces* strains exhibited a maximum specific growth rate on glucose of 0.4 $h^{-1}$ and 0.28 $h^{-1}$, respectively. The high glucose concentration and the resulting high specific growth rate of the *Saccharomyces* culture resulted in high rates of aerobic alcoholic fermentation (Table 3, FIG. 1). The specific rate of glucose consumption was about 2-fold higher in the *Saccharomyces* strain compared to the *Kluyveromyces* strain due to the vigorous alcoholic fermentation. From an energetic standpoint, alcoholic fermentation is a less efficient way for the cell to generate ATP. The biomass yield on glucose was 0.38 g/g for *Kluyveromyces* and 0.14 g/g for the *Saccharomyces uvarum*. The ethanol yield on glucose was zero for the crabtree-negative phenotype *Kluyveromyces* strain and 1.83 mmol/mmol for the *Saccharomyces*, the crabtree-positive phenotype, culture.

TABLE 3

Maximum specific growth rate, specific rates
(q, mmol (g biomass)$^{-1}$ h$^{-1}$) of
ethanol production and glucose consumption, the biomass yield (g/g),
product yield (mmol/mmol), and carbon recovery
(in %; only calculated for anaerobic cultures)
during exponential growth in batch cultures of
*Saccharomyces uvarum* and *Kluyveromyces marxianus* on
mineral medium containing 2% (wt/vol) glucose.

|  | *K. marxianus* | | *S. uvarum* | |
| --- | --- | --- | --- | --- |
|  | aerobic | anaerobic | aerobic | anaerobic |
| $T_{max}$ (h$^{-1}$) | 0.38 | 0.09 | 0.28 | 0.12 |
| $q_{glucose}$ | 5.8 | 7.6 | 10.9 | 7.2 |
| $q_{ethanol}$ | 0 | 9.9 | 20 | 9.7 |
| $Y_{p/s}$ | 0 | 1.3 | 1.83 | 1.35 |
| $Y_{x/s}$ | 0.38 | 0.07 | 0.14 | 0.09 |
| C-rec | — | 84.6 | — | 73.3 |

In anaerobic batch cultures, the specific growth rate and biomass yield for both strains was very low compared to that found under aerobic conditions (Table 3, FIGS. 1 and 2). For the *Kluyveromyces* and the *Saccharomyces* strains, the biomass yield was 0.07 and 0.09 g/g, respectively. Both the strains perform equally well with respect to the specific rate of alcoholic fermentation under anaerobic conditions. This was confirmed using $CO_2$ production data.

Generally, this Example demonstrates that aerobic production of biomass is much faster than anaerobic, and that yield of biomass under aerobic conditions is higher for crabtree negative organisms (because, in crabtree positive organisms, some alcoholic fermentation takes place, using up glucose). This Example also demonstrates that the fermentation product (ethanol, in this case) is produced at the same rate for both crabtree positive and negative organisms under anaerobic conditions. Thus, an aerobic growth stage provides the high biomass yield, and a subsequent anaerobic fermentation stage channels metabolic energy into product formation (rather than more growth). Overall, a process in which production is separated from growth provides greater process flexibility and better control over the overall process yield.

Example 18

Improved Lactate Production in a Host Strain that Naturally Makes L-lactic Acid: Amplification of Linear Fragments of Homologous DNA for Gene Disruptions of Pyruvate Decarboxylase The yeast *Kluyveromyces thermotolerans* (*K. thermotolerans*) is a natural producer of L-lactic acid (Kurtzman and Fell, (1998) "*The Yeasts, A Taxonomic Study*" pp. 240–241; Elsevier Science B.V.; Amsterdam, The Netherlands). *K. thermotolerans* has a naturally occurring lactate dehydrogenase (ldh) gene that allows for the production of L-lactic acid. The amount of lactic acid produced under anaerobic conditions is approximately 4% g/g of glucose utilized, while the remainder of the glucose is essentially converted into ethanol (42,5% g/g glucose consumed), glycerol (3% g/g of glucose consumed) and acetate (0.3 g/g % of glucose consumed).

TABLE 4

Results of anaerobic fermentation using *K. thermotolerans*, starting with 100 g/l glucose in YPAD media (rich media).

| Time | Glucose | Lactic | Acetate | Glycerol | Ethanol | Lactic YSI |
|---|---|---|---|---|---|---|
| 0 | 92.937 | 0 | 0 | 0 | 0.025 | 0.06 |
| 12 | 76.603 | 0.476 | 0 | 0.41 | 3.345 | 0.6 |
| 36 | 38.618 | 2.135 | 0 | 2.011 | 25.642 | 2.08 |
| 54 | 11.662 | 3.525 | 0.2 | 2.789 | 41.522 | 3.34 |
| 78 | 1.539 | 4.322 | 0.209 | 3.213 | 42.5 | 3.88 |
| 98 | 0.286 | 4.365 | 0.307 | 3.24 | 42.5 | 3.74 |

Figure 6F:
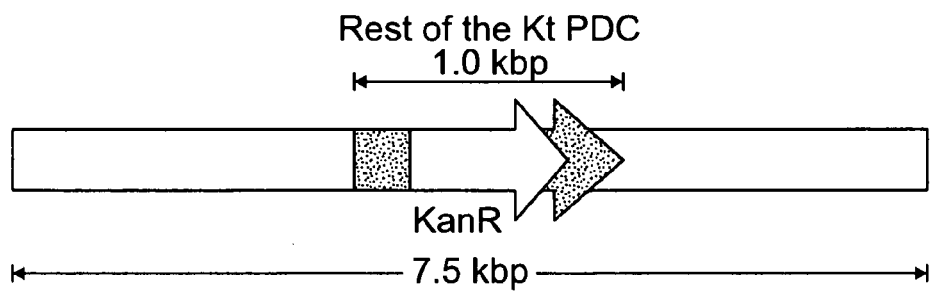
FIG. 6f is a diagram depicting the deletion of 750 bp from the 1.7 kbp PDC1 gene and the insertion of the kanamycin resistance gene.

A 600 bp region of the PDC1 was isolated from *K. thermotolerans* using consensus primers constructed from a sequence derived by comparing the PDC1 gene sequence from *K. marxianus* and *K. lactis*. The PDCI fragment was then sequenced (Sanger), and used to isolate a 7.5 kbp fragment surrounding the *K. thermotolerans* pdcl (FIG. 6e) using PCR and genome walking techniques (Clonetech). The 7.5 kbp fragment was then cloned into the pCRII TA cloning vector (Invitrogen). A portion of approximately 730 bp near the middle of the coding region of PDCI was removed from the *K. thermotolerans* 7.5 kbp fragment. The portion of *K. thermotolerans* pdcl removed by restriction digests (Sambrook) contained the following sequence:

TTACCACTGTCTTCGGTCTGCCAGGT-GACTTCAATCTGCGTCTGTTGGAC GAGATCTAC-GAGGTCGAGGGTATGAGATGGGCCGG-TAACTGTAACGAGT TGAACGCTTCTTACGCTGCCGACGCT-TACGCCAGAATCAAGGGTATGTCC TGTTTGAT-CACCACCTTCGGTGTCGGTGAGTTGTC-CGCTTTGAACGGTAT CGCCGGTTCTTACGCTGAGCACGTCGGT-GTCTTGCACATTGTCGGTGTCC CATCCGTCTC-CGCCCAGGCCAAGCAGCTATTGTTGCAC-CACACCTTGGGT AACGGTGACTTCACTGTCTTCCACA-GAATGTCCGCCAACATCTCTGAGAC CACTGC-TATGATCACTGATCTAGCTACCGC-CCCATCTGAGATCGACAGAT GTATCAGAACCACCTACATTAGACA-GAGACCTGTCTACTTGGGTTTGCCA TCTAACT-TCGTTGACCAGATGGTCCCAGCCTCTC-TATTGGACACCCCAAT TGACTTGGCCTTGAAGCCAAACGACCAG-CAGGCTGAGGAGGAGGTCATC TCTACTTTGTTG-GAGATGATCAAGGACGCTAAGAAC-CCAGTCATCTTGGC TGACGCTTGCGCTTCCAGACACGATGT-CAAGGCTGAGACCAAGAAGTTG ATTGACAT-CACTCAGTTCCCATCTTTCGTTAC-CCCAATGGGTAAGGGTTC CATTGACOAGAAGCACCCAAGATTCG-GTGGTGTCTACGTCGGTACCTTGT (Sequence ID No. 11). A gene encoding kanamycin resistance, including its promoter, was then isolated from pPTC9K vector (Invitrogen) by restriction digestion (Sambrook), and cloned into the site in the 7.5 kbp that from which the 730 bp fragment was removed. The sequence of the kanamycin resistance gene and its promoter from pPIC9K (Invitrogen) was as follows:

GTACAACTTGAGCAAGTTGTCGAT-CAGCTCCTCAAATTGGTCCTCTGTAA CGGAT-GACTCAACTTGCACATTAACTTGAAGCT-CAGTCGATTGAGTGAAC TTGATCAGGTTGTGCAGCTGGTCAGCAG-CATAGGGAAACACGGCTTTTCC TACCAAACT-CAAGGAATTATCAAACTCTGCAACACT-TGCGTATGCAGGT AGCAAGGGAAATGTCATACTTGAAGTCG-GACAGTGAGTGTAGTCTTGAG AAATTCTGAAGC-CGTATTTTTATTATCAGTGAGTCAGT-CATCAGGAGATC CTCTACGCCGGACGCATCGTGGCCGAC-CTGCAGGGGGGGGGGGGGCGCT GAGGTCTGC-CTCGTGAAGAAGGTGTTGCTGACTCAT-ACCAGGCCTGAAT CGCCCCATCATCCAGCCAGAAAGTGAGG-GAGCCACGGTTGATGAGAGCT TTGTTGTAGGTG-GACCAGTTGGT-GATTTTGAACTTTTGCTTTGCCACGGA ACGGTCTGCGTTGTCGGGAAGATGCGT-GATCTGATCCTTCAACTCAGCAA AAGTTCGATT-TATTCAACAAAGCCGCCGTCCCGT-CAAGTCAGCGTAATGC TCTGCCAGTGTTACAACCAATTAAC-CAATTCTGATTAGAAAAACTCATCG AGCAT-CAAATGAAACTGCAATTTATTCATAT-CAGGATTATCAATACCATA TTTTTGAAAAAGCCGTTTCTGTAAT-GAAGGAGAAAACTCACCGAGGCAG TTCCATAG-GATGGCAAGATCCTGGTATCGGTCTGC-GATTCCGACTCGTCC AACATCAATACAACCTATTAATTTC-CCCTCGTCAAAAATAAGGTTATCAA GTGAGAAATCACCATGAGTGACGACT-GAATCCGGTGAGAATGGCAAAAG CTTATG-CATTTCTTTCCAGACTTGTTAACAGGC-CAGCCATTACGCTCGT CATCAAAATCACTCGCATCAACCAAAC-CGTTATTCATTCGTGATTGCGCC TGAGCGAGAC-GAAATACGCGATCGCTGTTAAAAGGA-CAATTACAAACAG GAATCGAATGCAACCGGCGCAGGAA-CACTGCCAGCGCATCAACAATATT TTCACCT-GAATCAGGATATTCTTCTAATACCTG-GAATGCTGTTTTCCCGG GGATCGCAGTGGTGAGTAACCATGCAT-CATCAGGAGTACGGATAAAATG CTTGATGGTCG-GAAGAGGCATAAATTCCGTCAGCCAGTT-TAGTCTGACCA TCTCATCTGTAACATCATTGGCAACGC-TACCTTTGCCATGTTTCAGAAAC AACTCTGGCG-CATCGGGCTTCCCATACAATCGATAGAT-TGTCGCACCTGA TTGCCCGACATTATCGCGAGCCCATT-TATACCCATATAAATCAGCATCCA TGTTGGAATT-TAATCGCGGCCTCGAGCAAGACGTTTC-CCGTTGAATATGG CTCATAACACCCCTTGTATTACTGTT-TATGTAAGCAGACAGTTTTATTGTT CATGAT-GATATATTTTTATCTTGTGCAATGTAA-CATCAGAGATTTTGAGA CACAACGTGGCTTTCCCCCCCCCCCTG-CAGGTCGGCATCACCGGCGCCA CAGGTGCGGT-TGCTGGCGCCTATATCGCCGACATCAC-CGATGGGGAAGA TCGGGCTCGCCACTTCGGGCTCAT-GAGCGCTTGTTTCGGCGTGGGTATGG TGGCAG-GCCCCGTGGCCGGGGACTGTTGGGCGC-CATCTCCTTGCATG (Sequence ID No.12). The resulting construct includes the kanamycin resistance gene (G418) surrounded by approximately 6.8 kbp of the PDC region as shown in FIG. 6f. The construct depicted in FIG. 6f is digested with two restriction enzymes (Sambrook) to yield approximately 3 micrograms of fragment DNA containing the homologous PDC region and the mid-sequence inserted kanamycin resistance gene. *K. thermotolerans* is transformed with the fragment using known transformation techniques, such as electroporation to disrupt the PDC of *K. thermotolerans*. The method of electroporation is as follows: a) grow culture in YPAD overnight (~15 h) in a volume of 20 mL; b) transfer 500 uL of culture to a microfuge tube, spin @4K, 4 mm, discard supernatant; c) wash with 1 mL cold EB.(EB Electroporation Buffer: 10 mM Tris-HCl, pH 7.5; 270 mM Sucrose; 1 mM MgCl$_2$); d) resuspended in 1 mL IB (IB=Incubation Buffer: YPD; 25 mM DTT; 20 mM HEPES, pH8.0.); e) shake 800 rpm, 30° C. for 30 mm in an Eppendorf Thermomixer; f) spin down, wash once with EB, resuspend in 400 uL EB; g) add three micrograms fragment DNA (in water 10 mM Tris-Cl, pH 8.5), incubate on ice 30 mm; h) transfer to 0.4 cm electroporation cuvette. Bio-Rad Gene Pulser settings: 1000V, 1000A, 50 TF. Time constant after pulse: ~20 msec; i) transfer to 3 mL Morton Closure tube, incubate without shaking at 30° C. for 1 hour; j) add 400 uL liquid YPAD media (YPAD: 10 g Yeast Extract; 20 g Peptone; 20 g Glucose; 100 mg Adenine Hemisulphate. Volume 1L. No pH adjustment), shake 800 rpm, 30° C. for 1 hour in Eppendorf Thermomixer; k) add 400 uL liquid YPAD and recover 4–6 hours; l) spin down in microfuge tube @ 4K, 4 mm. discard supernatant, resuspend in 400 uL 1M Sorbitol and plate onto 100 ug/ml G418 selective plates; and m) incubate at 30° C. for three to five days.

Colonies are screened first by a second patching onto a culture dish containing 200 ug/ml 0418. The genomic DNA is isolated from the secondary yeast patch using standard genomic preparations (Sambrook). The isolated genomic is then screened via PCR for 1) the presence of the kanamycin fragment using suitable primers and conditions (Sambrook); and 2) the absence of the disrupted PDC region using suitable primers and PCR conditions. Colonies positive for the selection marker and negative for the PDC disruption region are then grown for further study, for example, genomic DNA from these strains is further analyzed by southern hybridization analysis.

Example 19

Cloning of Yeast, Fungal and Bacterial LDH Genes

LDH-encoding genes were isolated from two species of yeast, *Kluyveromyces thermotolerans* and *Torulaspora pretoriensis*. These species were known to produce lactic acid (Witte et al., 1989, *J. Basic Microbiol.* 29: 707–716). All conventional procedures were performed according to procedures set forth in Sambrook et al., ibid., except as otherwise noted.

*Kluyveromyces thermotolerans* LDH

*K. thermotolerans* was obtained from the American Type Culture Collection (ATCC Accession #52709) and grown under standard conditions. Genomic DNA was purified from these cells using an Invitrogen "Easy-DNA" kit according to the manufacturer's protocol. Degenerate amplification primers were designed by reverse translating conserved regions identified in alignments of L-LDH encoding genes from *Rhizopus oryzae*, *Homo sapiens*, *Drosophila melanogaster*, *Aribidopsis thaliana*, and *Lactobacillus helveticus*. Two degenerate oligonucleotides were used successfully in polymerase chain reaction (PCR) amplifications. These oligonucleotides were:

```
EJP4    GTBATYGGYTCHGGTAC      (SEQ ID No. 13)
and

EJP5    SWRTCDCCRTGYTCACC.     (SEQ ID No. 14)
```

PCR amplification reactions were performed using Perkin Elmer buffer II (1.5 mM MgCl$_2$) and AmpliTaq Gold polymerase. Each reaction contained *K. thermotolerans* genomic DNA at a concentration of 6 ng/uL, each of 4 dNTPs at a concentration of 0.2 mM, and each of the EJP4 and EJP5 primers at 1 uM. Reactions were performed according to the following cycling conditions: an initial incubation for 10 min at 95° C., followed by 35 cycles consisting of 30 sec at 95° C., 40 sec. at 52° C., 40 sec at 72° C. A faint product fragment of 116 basepairs (bp) was gel purified using conventional procedures, reamplified using the same conditions and amplification conditions disclosed herein, cloned, and sequenced.

The resulting sequence could be translated into a polypeptide that exhibited excellent homology to known L-LDH-encoding genes. Two non-degenerate primers, EJP8 and EJP9, were designed based on this sequence:

```
EJP8    GTACAGTTCTGGATACTGCTCG    (SEQ ID No. 15)
and

EJP9    ACAGGCATCGATGCTGTC.       (SEQ ID No. 16)
```

A genomic DNA library was constructed using *K. thermotolerans* DNA by inserting random fragments generated by partial Sau3A digests of the DNA into the BamH1 site of plasmid Yep9T (ref). The complete *K. thermotolerans* LDH-encoding gene was isolated by PCR using primers EJP8 and EJP9 in combination with primers in the vector arms. These vector primers were

```
EJP10   CTACTTGGAGCCACTATCGAC     (SEQ ID No. 17)
and

EJP11   GTGATGTCGGCGATATAGG.      (SEQ ID No. 18)
```

In these amplification reactions, the conditions were as described above except that the extension time was increase to 2 min and the annealing temperature was increased to 58° C. Amplification products were cloned and sequenced and shown to contain the remainder of the *K. thermotolerans* LDH-encoding gene from based on homology to known sequence.

Finally, the full-length gene was re-isolated directly from *K. thermotolerans* genomic DNA using a high-fidelity polymerase (Pfu) in PCR amplification reactions using primers EJP12 and EJP13:

```
EJP12   GATCTCCTGCTAAGCTCTTGC     (SEQ ID No. 19)
and

EJP13   GCAGTTTTGGATATTCATGC.     (SEQ ID No. 20)
```

These amplification reactions were performed as described above. The coding sequence of this independently generated PCR product agreed completely with the AmpliTaq Gold generated sequences. The nucleic acid sequence of the coding region of the *K. thermotolerans* LDH-encoding gene is presented below as SEQ ID No. 20.

The translation of the complete coding sequence showed significant sequence identity to L-LDH-encoding genes from *Schizosaccharomyces pombe* (49.5%), *Bacillus megaterium* (45.1%), *Lactobacillus helveticus* (36.8%), cow (35.3%), and *Rhizopus oryae* (32.6%), among others.

Nucleotide Sequence of *K. thermotolerans* lactate dehydrogenase:
```
ATGTTCCAAG ATACAAAGTC TCAAGCAGTA AGAACTGATG CCAAAACAGT AAAAGTTGTG   60 (SEQ ID No. 21)

GTAGTGGGAG TGGGAAGTGT TGGGTCTGCC ACAGCGTATA CGTTGCTTCT CAGCGGCATC  120

GTTTCCGAGA TTGTCCTTAT CGACGTGAAC AAAGACAAAG CAGAGGGTGA AGCATGGAC   180

TTAAACCACG CAGCACCTTC AAATACAAGG TCTCGAGCGG GTGATTATCC TGACTGCGCT  240

GGCGCGGCCA TTGTTATTGT CACATGTGGG ATTAACCAAA AAAATGGACA ACAAGGATG   300

GATCTTGCTG CAAAAAATGC CAACATTATG CTGGAAATCA TCCCCAATGT TGCCAAATAT  360

GCTCCTGATA CCATCCTGCT TATTGCCACG AATCCTGTCG ATGTTTTGAC CTATATTAGC  420

TATAAGGCGT CAGGGTTTCC ACTAAGCAGA GTTATCGGCT CAGGTACAGT TCTGGATACT  480

GCTCGTTTTA AATACATCCT CGGAGAGCAC TTCAAGATCT CATCGGACAG CATCGATGCC  540

TGTGTAATTG GAGAACATGG TGATTCGGGT GTGCCTGTCT GGTCTCTTAC CAACATCGAC  600

GGCATGAAGC TCCGGGATTA CTGCGAAAAA GCCAACCACA TATTTGATCA GAATGCGTTC  660

CATAGAATCT TTGAGCAAAC GCGAGACGCT GCTTACGATA TCATCAAGCG CAAAGGCTAT  720

ACTTCATATG GAATCGCAGC GGGATTACTT CGCATAGTAA AGGCGATTTT AGAGGATACA  780

GGATCCACAC TTACAGTTTC AACCGTTGGT GATTATTTTG GGGTTGAACA AATTGCTATA  840

AGCGTCCCTA CCAAACTCAA TAAAAGTGGG GCTCATCAAG TGGCTGAACT TTCACTCGAT  900

GAGAAGGAAA TAGAATTGAT GGAAAAATCA GCTAGTCAGA TCAAATCAGT GATTGAGCAT  960

CATGGAGATCAAT                                                      972
```

Amino Acid Sequence of *K. thermotolerans* lactate dehydrogenase:
```
Met Phe Gln Asp Thr Lys Ser Gln Ala Val Arg Thr Asp Ala Lys Thr   (SEQ ID No. 22)
1               5                   10                  15

Val Lys Val Val Val Gly Val Gly Ser Val Gly Ser Ala Thr Ala
                20                  25                  30

Tyr Thr Leu Leu Leu Ser Gly Ile Val Ser Glu Ile Val Leu Ile Asp
            35                  40                  45

Val Asn Lys Asp Lys Ala Glu Gly Glu Ser Met Asp Leu Asn His Ala
        50                  55                  60

Ala Pro Ser Asn Thr Arg Ser Arg Ala Gly Asp Tyr Pro Asp Cys Ala
65                  70                  75                  80

Gly Ala Ala Ile Val Ile Val Thr Cys Gly Ile Asn Gln Lys Asn Gly
                85                  90                  95

Gln Thr Arg Met Asp Leu Ala Ala Lys Asn Ala Asn Ile Met Leu Glu
                100                 105                 110

Ile Ile Pro Asn Val Ala Lys Tyr Ala Pro Asp Thr Ile Leu Leu Ile
            115                 120                 125

Ala Thr Asn Pro Val Asp Val Leu Thr Tyr Ile Ser Tyr Lys Ala Ser
        130                 135                 140

Gly Phe Pro Leu Ser Arg Val Ile Gly Ser Gly Thr Val Leu Asp Thr
145                 150                 155                 160

Ala Arg Phe Lys Tyr Ile Leu Gly Glu His Phe Lys Ile Ser Ser Asp
                165                 170                 175

Ser Ile Asp Ala Cys Val Ile Gly Glu His Gly Asp Ser Gly Val Pro
            180                 185                 190

Val Trp Ser Leu Thr Asn Ile Asp Gly Met Lys Leu Arg Asp Tyr Cys
        195                 200                 205

Glu Lys Ala Asn His Ile Phe Asp Gln Asn Ala Phe His Arg Ile Phe
    210                 215                 220
```

```
Glu Gln Thr Arg Asp Ala Ala Tyr Asp Ile Ile Lys Arg Lys Gly Tyr
225                 230                 235                 240

Thr Ser Tyr Gly Ile Ala Ala Gly Leu Leu Arg Ile Val Lys Ala Ile
            245                 250                 255

Leu Glu Asp Thr Gly Ser Thr Leu Thr Val Ser Thr Val Gly Asp Tyr
260                 265                 270

Phe Gly Val Glu Gln Ile Ala Ile Ser Val Pro Thr Lys Leu Asn Lys
        275                 280                 285

Ser Gly Ala His Gln Val Ala Glu Leu Ser Leu Asp Glu Lys Glu Ile
        290                 295                 300

Glu Leu Met Glu Lys Ser Ala Ser Gln Ile Lys Ser Val Ile Glu His
305                 310                 315                 320

Leu Glu Ile Asn
```

Torulaspora pretoriensis LDH

The L-LDH-encoding gene of *T. pretoriensis* was isolated in a similar manner to the *K. thermotolerans* gene. The strategy was again to isolate a segment of the gene using PCR amplification of *T. preoriensis* genomic DNA using degenerate primers and to isolate the remainder of the gene via PCR-based chromosome walking. *T. pretoriensis* was obtained from the American Type Culture Collection (ATCC Accession No. 36245). Genomic DNA was purified from these cells using the Invitrogen "Easy-DNA" kit according to the manufacturer's protocol. Degenerate primers were designed based on conserved sequences as described above. Two degenerate oligonucleotides were used successfully in polymerase chain reaction (PCR) amplifications:

```
EJP1    GTYGGTGCHGGTGCHGTHGG       (SEQ ID No. 23)
and

EJP6    SWRTCDCCRTGYTCBCC.         (SEQ ID No. 24)
```

Thermocycling parameters and reaction conditions were as described above, except that *T. pretoriensis* genomic DNA was used at a concentration of 20 ng/uL. A strong product DNA fragment of 508 bp was cloned and sequenced. The resulting 169 amino acid translation product exhibited excellent homology to known L-LDH-encoding genes.

The remainder of the gene was isolated by "walking" in both directions from the known sequence. This was accomplished using a GenomeWalker kit (Clontech #K1807-1) and Advantage Genomic Polymerase Mix (Clontech #8418-1) according to the manufacturer's instructions. Four gene-specific nested primers were used in addition to the adaptor primers provided in the kit. The gene-specific primers were:

```
EJP20
ATCCACAACAGCTTACACGTTATTGAG      (SEQ ID No. 25)

EJP21
GTTTGGTTGCTGGAAGTGGTGTTGATAG     (SEQ ID No. 26)

EJP22
AACATTGAATAGCTTGCTCAGGTTGTG      (SEQ ID No. 27)
and

EJP23
GATAATAAACGCGTTGACATTTCAGATG.    (SEQ ID No. 28)
```

Products were cloned and sequenced and found to contain the remainder of the LDH-encoding gene from *T. pretoriensis*, based on homology to known sequences. Translation of the complete coding sequence showed significant sequence identity to L-LDH-encoding genes from *Schizosaccharomyces pombe* (48.8%), *Bacillus megaterium* (42%), *Lactobacillus helveticus* (38.2%), cow (34.9%), and *Rhizopus oryzae* (32.2%), among others. The nucleic acid sequence of the coding region of the *T. pretoriensis* LDH-encoding gene is presented below as SEQ ID No. 28, and the predicted amino acid sequence of the LDH protein encoded therein is identified as SEQ ID No. 29.

```
Nucleotide Sequence of T. pretoriensis lactate dehydrogenase:
ATGCATAGAT GTGCTAAAGT GGCCATCGTC GGTGCCGGCC AAGTTGGATC CACAACAGCT    60 (SEQ ID No. 29)

TACACGTTAT TATTGAGTAG TTTGGTTGCT GAAGTGGTGT TGATAGATGT CGATAAAAGA   120

AAGGTCGAAG GCCAATTTAT GGATCTGAAC CACGCGGCTC CTTTAACGAA GGAGTCACGA   180

TTCAGTGCTG GGGACTATGA AAGTTGTGCT GATGCTGCGG TTGTAATCGT AACGGGCGGG   240

GCTAATCAGA AACCTGGTCA AACTAGAATG GAGCTAGCCG AGAGGAACGT TAAAATCATG   300

CAGGAAGTGA TCCCTAAGAT TGTGAAATAC GCCCCCAACG CAATTTTGCT GATTGCAACA   360

AACCCTGTCG ATGTACTTAC CTATGCTAGT TTGAAAGCGT CGGGATTCCC AGCAAGCCTT   420

GTTATTGGTT CTGGGACAGT TCTCGACTCT GCTCGTATAC AGCACAACCT GAGCAAGCTA   480
```

-continued

```
TTCAATGTTT CATCTGAAAG TGTCAACGCG TTTATTATCG GGGAACATGG TGACTCAAGT    540

GTGCCCGTCT GGTCGCTTGC TGAGATTGCC GGCATGAAAG TGGAGGATTA CTGTAGGCAG    600

TCCAAGAGAA AGTTTGACCC CAGCATTCTG ACCAAAATAT ATGAGGAGTC GCGTGACGCG    660

GCAGCCTACA TCATAGAACG CAAAGGCTAT ACCAATTTCG GGATTGCAGC AGGTTTGGCT    720

AGGATAGTGA GAGCTATTCT GAGAGATGAA GGTGCCCTAT TAACTGTGTC TACTGTAGGT    780

GAGCACTTTG GCATGAAAGA TGTTTCATTG AGTGTTCCAA CTAGGGTAGA CAGGAGCGGC    840

GCTCACCATG TCGTCGACCT TCTGCTAAAC GACAAGGAGC TGGAGCAAAT TAAACATCT    900

GGAGCCAAGA TAAAGTCAGC CTGTGATGAA CTTGGCATT                            939
```

Amino Acid Sequence of *T. pretoriensis* lactate dehydrogenase:
(SEQ ID No. 30)

```
Met His Arg Cys Ala Lys Val Ala Ile Val Gly Ala Gly Gln Val Gly
1               5                   10                  15

Ser Thr Thr Ala Tyr Thr Leu Leu Ser Ser Leu Val Ala Glu Val
            20                  25                  30

Val Leu Ile Asp Val Asp Lys Arg Lys Val Glu Gly Gln Phe Met Asp
            35                  40                  45

Leu Asn His Ala Ala Pro Leu Thr Lys Glu Ser Arg Phe Ser Ala Gly
        50                  55                  60

Asp Tyr Glu Ser Cys Ala Asp Ala Ala Val Val Ile Val Thr Gly Gly
65                  70                  75                  80

Ala Asn Gln Lys Pro Gly Gln Thr Arg Met Glu Leu Ala Glu Arg Asn
                85                  90                  95

Val Lys Ile Met Gln Glu Val Ile Pro Lys Ile Val Lys Tyr Ala Pro
            100                 105                 110

Asn Ala Ile Leu Leu Ile Ala Thr Asn Pro Val Asp Val Leu Thr Tyr
        115                 120                 125

Ala Ser Leu Lys Ala Ser Gly Phe Pro Ala Ser Arg Val Ile Gly Ser
        130                 135                 140

Gly Thr Val Leu Asp Ser Ala Arg Ile Gln His Asn Leu Ser Lys Leu
145                 150                 155                 160

Phe Asn Val Ser Ser Glu Ser Val Asn Ala Phe Ile Ile Gly Glu His
                165                 170                 175

Gly Asp Ser Ser Val Pro Val Trp Ser Leu Ala Glu Ile Ala Gly Met
            180                 185                 190

Lys Val Glu Asp Tyr Cys Arg Gln Ser Lys Arg Lys Phe Asp Pro Ser
            195                 200                 205

Ile Leu Thr Lys Ile Tyr Glu Glu Ser Arg Asp Ala Ala Ala Tyr Ile
        210                 215                 220

Ile Glu Arg Lys Gly Tyr Thr Asn Phe Gly Ile Ala Ala Gly Leu Ala
225                 230                 235                 240

Arg Ile Val Arg Ala Ile Leu Arg Asp Glu Gly Ala Leu Leu Thr Val
                245                 250                 255

Ser Thr Val Gly Glu His Phe Gly Met Lys Asp Val Ser Leu Ser Val
            260                 265                 270

Pro Thr Arg Val Asp Arg Ser Gly Ala His His Val Val Asp Leu Leu
        275                 280                 285

Leu Asn Asp Lys Glu Leu Glu Gln Ile Lys Thr Ser Gly Ala Lys Ile
        290                 295                 300

Lys Ser Ala Cys Asp Glu Leu Gly Ile
305                 310
```

*B. megaterium* LDH

*B. megaterium* DNA encoding the LDH gene was isolated as follows. *B. megaterium* was obtained from the American Type Culture Collection (ATCC Accession #6458) and grown under standard conditions. Genomic DNA was purified from these cells using an Invitrogen "Easy-DNA" kit according to the manufacturer's protocol. Primers were designed on the basis of the available sequence in Genbank for the L-LDH from *B. megaterium* (Genbank accession # M22305). PCR amplification reactions were performed using Perkin Elmer buffer II (1.5 mM MgCl$_2$) and AmpliTaq Gold polymerase. Each reaction contained *B. megaterium* genornic DNA at a concentration of 6 ng/uL, each of 4 dNTPs at a concentration of 0.2 mM, and each of two amplification primers BM1270 and BM179 at a concentration of 1 uM, where these primers have the sequence:

```
BM1270    CCTGAGTCCACGTCATTATTC       (SEQ ID No. 31)
and

BM179     TGAAGCTATTTATTCTTGTTAC.     (SEQ ID No. 32)
```

Reactions were performed according to the following themocycling conditions: an initial incubation for 10 min at 95° C., followed by 35 cycles consisting of 30 sec at 95° C., 30 sec. at 50° C., 60 sec at 72° C. A strong product fragment of 1100 base pairs (bp) was gel purified using conventional procedures, cloned, and sequenced. The resulting sequence could be translated into a polypeptide that exhibited excellent homology to known L-LDH-encoding genes.

The coding sequence for the *B. megaterium* LDH-encoding gene (SEQ ID No. 32) disclosed herein was operatively linked to a promoter from the phosphoglycerate kinase gene and a transcriptional terminator from the GAL10 gene, both from the yeast *Saccharomyces cerevisiae*. In making this construct, the following oligonucleotides were prepared and used to amplify the coding sequence from a plasmid containing an insert having the sequence identified as SEQ ID No. 29. Two oligonucleotide primers, Bmeg5' and Bmeg3', were designed based on this sequence to introduce restriction sites at the ends of the coding sequence of the gene:

```
Bmeg5'
GCTCTAGATGAAAACACAATTTACACC     (SEQ ID No. 33)
and

Bmeg3'
ATGGATCCTTACACAAAAGCTCTGTCGC.   (SEQ ID No. 34)
```

This amplification reaction was performed using dNTP and primer concentrations described above using Pfu Turbo polymerase (Stratagene) in a buffer supplied by the manufacturer. Thermocycling was done by initially incubating the reaction mixture for 3 min at 95° C., then by 20 cycles of 30 sec at 95° C., 30 sec at 50° C., 60 sec at 72° C., followed by a final incubation for 9 min at 72° C. The product was digested with restriction enzymes XbaI and BamHI and then ligated into the XbaI and BamHI sites of plasmid pNC101 (NREL). This ligation resulted in the PGK promoter and GAL10 terminator becoming operably linked (i.e., trascriptionally-active in a yeast cell) to the *B. megaterium* LDH coding sequence. Once the *B. megaterium* LDH had been operably linked to these transcription control sequence, the NotI-NotI fragment was excised and re-cloned into a vector capable of replicating in *Kluyveromyces* species (plasmid pNC003, NREL). The resulting plasmid contained the LDH-containing NotI-NotI fragment as well as a 4,756 bp sequence between the SphI sites from the *K. lactis* plasmid pKD1.

Figure 17:
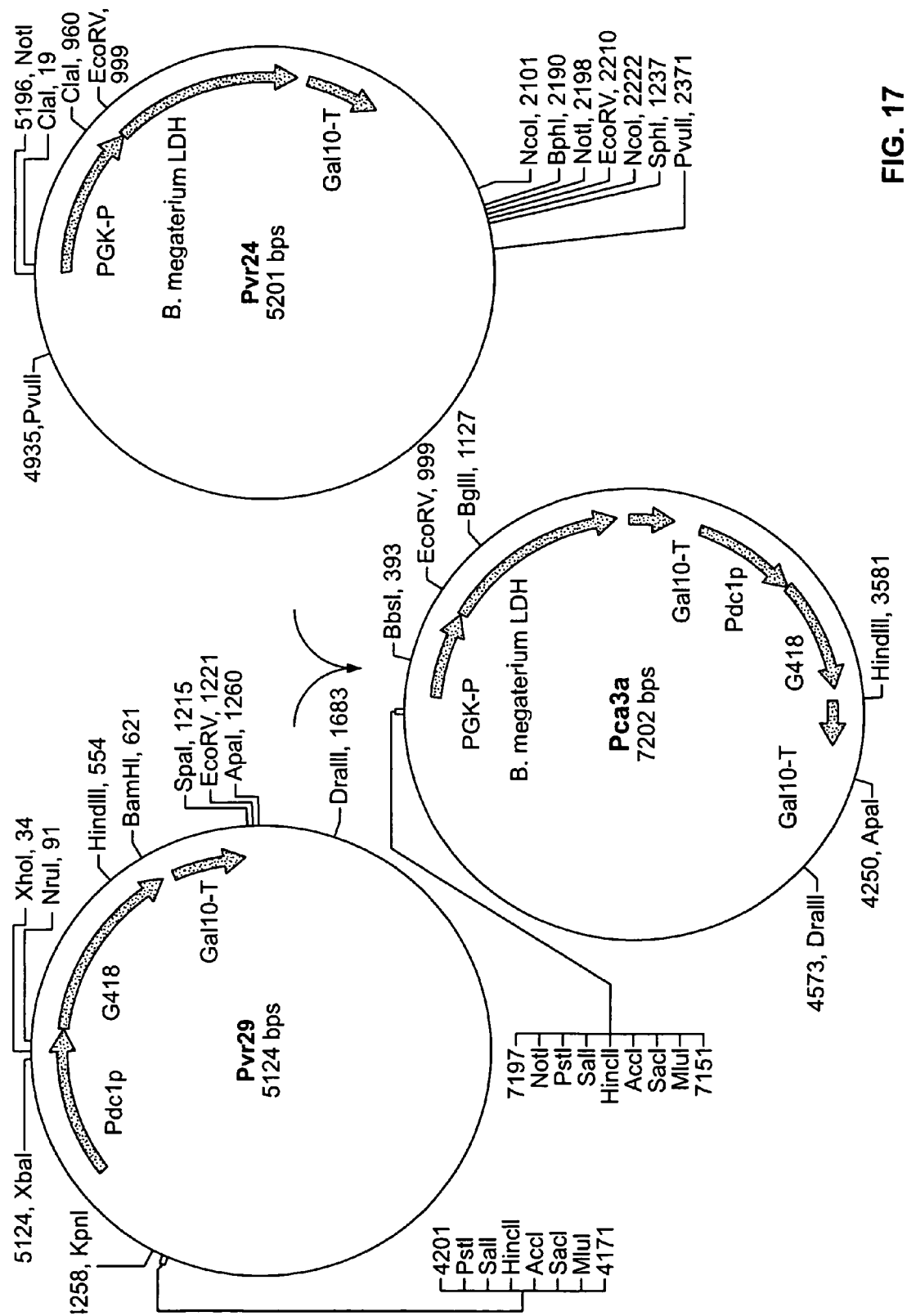
FIG. 17 is a diagram of recombinat expression constructs pvr29 and pvr24, and construct pca3a prepared therefrom.

These plasmids are shown in FIG. 17.

*Rhizopus oryzae* LDH

L-LDH was isolated from *Rhizopus oryzae* as follows. *Rhizopus oryzae* cells were obtained from the American Type Culture Collection (ATCC Accession #9363) and grown under standard conditions. Genomic DNA was purified from these cells using an Invitrogen "Easy-DNA" kit according to the manufacturer's protocol. Primers were designed on the basis of the available sequence in Genbank for the L-LDH from *R. oryzae* (Genbank accession # AF226154). PCR amplification reactions were performed using Perkin Elmer buffer II (1.5 mM MgCl$_2$) and AmpliTaq Gold polymerase. Each reaction contained *R. oryzae* genomic DNA at a concentration of 6 ng/uL, each of 4 dNTPs at a concentration of 0.2 mM, and each of the amplification primers Ral-5' and Ral-3' primers at 1 uM. The amplification primers had the sequence:

```
Ral-5'
CTTTATTTTTCTTTACAATATAATTC      (SEQ ID No. 35)
and

Ral-3'
ACTAGCAGTGCAAAACATG.            (SEQ ID No. 36)
```

Reactions were performed according to the following cycling conditions: an initial incubation for 10 min at 95° C., followed by 35 cycles consisting of 30 sec at 95° C., 30 sec. at 41° C., 60 sec at 72° C. A strong product fragment of 1100 base pairs (bp) was gel purified using conventional procedures, cloned in TA vector (Invitrogen, Carlsbad, Calif.) and sequenced. The resulting sequence could be translated into a polypeptide that exhibited excellent homology to known *Rhizopus oryzae* L-LDH-encoding gene sequence in Genbank (Accession # AF226154).

The coding sequence for the *R. oryzae* LDH-encoding gene disclosed herein was operatively linked to a promoter from the phosphoglycerate kinase gene and a transcriptional terminator from the GAL10 gene, both from the yeast *S. cervisiae*. In making this construct, the following oligonucleotides were prepared and used to amplify the coding sequence from the plasmid containing the *Rhizopus* LDH insert. Two oligonucleotide primers, Rapgk5 and Papgk3', were designed based on this sequence to introduce restriction sites at the ends of the coding sequence of the gene.

```
Rapgk5
GCTCTAGATGGTATTACACTCAAAGGTCG   (SEQ ID No. 37)
and

Papgk3
GCTCTAGATCAACAGCTACTTTTAGAAAAG. (SEQ ID No. 38)
```

This amplification reaction was performed using dNTP and primer concentrations as described above using Pfu Turbo polymerase (Stratagene) in a buffer supplied by the manufacturer. Thermocycling was done by initially incubating the reaction mixture for 3 min at 95° C., then by 20 cycles of 30 sec at 95° C., 30 sec at 53° C., 60 sec at 72° C., followed by a final incubation for 9 min at 72° C. The product was digested with restriction enzymes XbaI and then ligated into the XbaI site of plasmid pNC101 (NREL).

This ligation resulted in the PGK promoter and GAL10 terminator becoming operably linked (i.e., trascriptionally-active in a yeast cell) to the R. oryzae L-LDH coding sequence. Once the R. oryzae LDH had been operably linked to these transcription control sequence, the NotI-NotI fragment was excised and re-cloned into a vector capable of replicating in Kluyveromyces species (plasmid pNC003, NREL). The resulting plasmid contained the LDH-containing NotI-NotI fragment as well as a 4,756 bp sequence between the SphI sites from the K. lactis plasmid pKD1.

G418 Resistance Marker Vectors Encoding an LDH Gene Isolated from K. thermotolerns, R. oryzae or B. megaterium.

The G418 antibiotic selection marker obtained from Invitrogen (Carlsbad, Calif.) was modified and operatively linked to a promoter from the pyruvate decarboxylase gene and a transcriptional terminator from the GAL10 gene, both from the yeast S. cerevisiae. In making this construct, the following oligonucleotides were prepared and used to amplify the coding sequence from the plasmid containing the G418 resistance gene insert. Two oligonucleotide primers, G5' and G3', were designed based on this sequence to introduce restriction sites at the ends of the coding sequence of the gene.

G5' AAATCTAGATGAGCCATATTCAACGGGA (SEQ ID No. 39) and

G3' CCGGATCCTTAGAAAAACTCATCGAGCAT. (SEQ ID No. 40)

These oligonucleotides were used to amplify the G418 gene from pPIC9K vector (Invitrogen, Carlsbad, Calif.). This amplification reaction was performed using dNTP and primer concentrations described above using Pfu Turbo polymerase (Stratagene) in a buffer supplied by the manufacturer. Thermocycling was done by initially incubating the reaction mixture for 3 min at 95° C., then by 20 cycles of 30 sec at 95° C., 30 sec at 50° C., 60 sec at 72° C., followed by a final incubation for 9 min at 72° C. The product was digested with restriction enzymes XbaI and BamHI and then ligated into the XbaI and BamHI site of plasmid pNC104 (NREL)

The LDH gene from the B. megaterium, operatively linked to a promoter from the phosphoglycerate kinase gene and a transcriptional terminator from the GAL10 gene, both from the yeast S. cerevisiae, was introduced into this vector at the SphI site at the 3' end of the Gal10 Terminator of the G418 gene. This essentially coupled the G418 selection marker gene and the B. megaterium LDH gene to give plasmid pCA5. Plasmid pCA5 was restriction digested to excise the 4 kilobasepair (Kbp) fragment that consisted of the G418 selection marker gene and the B. megaterium LDH gene. This 4 Kbp fragment was used to transform K. marxianus using chemical and electroporation methods discussed herein.

Example 20

Transforming Yeast with Novel LDHs

The coding sequence for the K. thermotolerans LDH-encoding gene (SEQ ID No. 20) disclosed herein was operatively linked to a promoter from the phosphoglycerate kinase gene and a transcriptional terminator from the GAL10 gene, both from the yeast Saccharomyces cervisiae. In making this construct, the following oligonucleotides were prepared and used amplify the coding sequence from a plasmid containing the insert:

EJP14 GCTCTAGAATTATGTTCCAAGATACAAAGTCTCAAG (SEQ ID No. 41) and

EJP15 CCGGAATTCATCCTCAATTGATCTCCAGATGCTC, (SEQ ID. No. 42)

This amplification reaction was performed using dNTP and primer concentrations described above using Pfu Turbo polymerase (Stratagene) in a buffer supplied by the manufacturer. Thermocycling was done by initially incubating the reaction mixture for 3 min at 95° C., then by 20 cycles of 30 sec at 95° C., 40 sec at 60° C., 60 sec at 72° C., followed by a final incubation for 9 min at 72° C. The product was digested with restriction enzymes XbaI and EcoRI and then ligated into the XbaI and EcoRI sites of plasmid pNC101 (SOURCE). This ligation resulted in the PGK promoter and GAL10 terminator becoming operably linked (i.e., trascriptionally-active in a yeast cell) to the K. thermotolerans LDH coding sequence. A NotI-NotI fragment of this plasmid, containing the resulting fusion of promoter, K. thermotolerans LDH coding sequence and terminator, is disclosed herein identified as SEQ ID No. 43:

```
GCGGCCGCGG ATCGCTCTTC CGCTATCGAT TAATTTTTTT TTCTTTCCTC TTTTTATTAA    60

CCTTAATTTT TATTTTAGAT TCCTGACCTT CAACTCAAGA GGGACAGATA TTATAACATC   120

TGCACAATAG GCATTTGCAA GAATTACTCG TGAGTAAGGA AAGAGTGAGG AACTATCGCA   180

TACCTGCATT TAAAGATGCC GATTTGGGCG CGAATCCTTT ATTTTGGCTT CACCCTCATA   240

CTATTATCAG GGCCAGAAAA AGGAAGTGTT TCCCTCCTTC TTGAATTGAT GTTACCCTCA   300

TAAAGCACGT GGCCTCTTAT CGAGAAAGAA ATTACCGTCG CTCGTGATTT GTTTGCAAAA   360

AGAACAAAAC TGAAAAAACC CAGACACGCT CGACTTCCTG TCTTCCTATT GATTGCAGCT   420

TCCAATTTCG TCACACAACA AGGTCCTAGC GACGGCTCAC AGGTTTTGTA ACAAGCAATC   480

GAAGGTTCTG GAATGGCGGG AAAGGGTTTA GTACCACATG CTATGATGCC CACTGTGATC   540

TCCAGAGCAA AGTTCGTTCG ATCGTACTGT TACTCTCTCT CTTTCAAACA GAATTGTCCG   600

AATCGTGTGA CAACAACAGC CTGTTCTCAC ACACTCTTTT CTTCTAACCA AGGGGGTGGT   660
```

-continued

```
TTAGTTTAGT AGAACCTCGT GAAACTTACA TTTACATATA TATAAACTTG CATAAATTGG    720

TCAATGCAAG AAATACATAT TTGGTCTTTT CTAATTCGTA GTTTTTCAAG TTCTTAGATG    780

CTTTCTTTTT CTCTTTTTTA CAGATCATCA AGGAAGTAAT TATCTACTTT TTACAACAAA    840

TCTAGAATTA TGTTCCAAGA TACAAAGTCT CAAGCAGTAA GAACTGATGC CAAAACAGTA    900

AAAGTTGTGG TAGTGGGAGT GGGAAGTGTT GGGTCTGCCA CAGCGTATAC GTTGCTTCTC    960

AGCGGCATCG TTTCCGAGAT TGTCCTTATC GACGTGAACA AAGACAAAGC AGAGGGTGAA   1020

AGCATGGACT TAAACCACGC AGCACCTTCA AATACAAGGT CTCGAGCGGG TGATTATCCT   1080

GACTGCGCTG GCGCGGCCAT TGTTATTGTC ACATGTGGGA TTAACCAAAA AAATGGACAA   1140

ACAAGGATGG ATCTTGCTGC AAAAAATGCC AACATTATGC TGGAAATCAT CCCCAATGTT   1200

GCCAAATATG CTCCTGATAC CATCCTGCTT ATTGCCACGA ATCCTGTCGA TGTTTTGACC   1260

TATATTAGCT ATAAGGCGTC AGGGTTTCCA CTAAGCAGAG TTATCGGCTC AGGTACAGTT   1320

CTGGATACTG CTCGTTTTAA ATACATCCTC GGAGAGCACT TCAAGATCTC ATCGGACAGC   1380

ATCGATGCCT GTGTAATTGG AGAACATGGT GATTCGGGTG TGCCTGTCTG GTCTCTTACC   1440

AACATCGACG GCATGAAGCT CCGGGATTAC TGCGAAAAAG CCAACCACAT ATTTGATCAG   1500

AATGCGTTCC ATAGAATCTT TGAGCAAACG CGAGACGCTG CTTACGATAT CATCAAGCGC   1560

AAAGGCTATA CTTCATATGG AATCGCAGCG GGATTACTTC GCATAGTAAA GGCGATTTTA   1620

GAGGATACAG GATCCACACT TACAGTTTCA ACCGTTGGTG ATTATTTTGG GGTTGAACAA   1680

ATTGCTATAA GCGTCCCTAC CAAACTCAAT AAAAGTGGGG CTCATCAAGT GGCTGAACTT   1740

TCACTCGATG AGAAGGAAAT AGAATTGATG GAAAAATCAG CTAGTCAGAT CAAATCAGTG   1800

ATTGAGCATC TGGAGATCAA TTGAGGATGA ATTCGGATCC GGTAGATACA TTGATGCTAT   1860

CAATCCAGAG AACTGGAAAG ATTGTGTAGC CTTGAAAAAC GGTGAAACTT ACGGGTCCAA   1920

GATTGTCTAC AGATTTTCCT GATTTGCCAG CTTACTATCC TTCTTGAAAA TATGCACTCT   1980

ATATCTTTTA GTTCTTAATT GCAACACATA GATTTGCTGT ATAACGAATT TTATGCTATT   2040

TTTTAAATTT GGAGTTCAGT GATAAAAGTG TCACAGCGAA TTTCCTCACA TGTAGGGACC   2100

GAATTGTTTA CAAGTTCTCT GTACCACCAT GGAGACATCA AAAATTGAAA ATCTATGAAA   2160

AGATATGGAC GGTAGCAACA AGAATATAGC ACGAGCCGCG GATTTATTTC GTTACGCATG   2220

CGCGGCCGC                                                          2229
```

Once the *K. thermotolerans* LDH had been operably linked to these transcription control sequence, the NotI-NotI fragment was excised and re-cloned into a vector capable of replicating *Kluyveromyces* species (plasmid pNC003, Invitrogen, Carlsbad, Calif.). The resulting plasmid contained the LDH-containing NotI-NotI fragment (SEQ ID No. 43) as well as a 4,756 bp sequence between the SphI sites from the *K. lactis* plasmid pKD1 (Chen et al., 1986, *Nucleic Acids Res.* 14: 4471–4481). In addition, pNC003 carries the zeocin resistance gene under the control of the yeast TEF promoter (Hwang et al., 1993, *EMBO J.* 12: 2337–2348). Both orientations of the NotI-NotI fragment were obtained and were termed pNC102 andpNC103.

These plasmids were introduced into *K. marxianus* and *K. lactis* substantially as described below. Plasmids pNC102 and pNC103 were introduced into the yeast cells by the chemical transformation method. Plasmid pNC003, which does not contain an LDH-encoding gene, was introduced into yeast cells as a control. Transformants were selected on YPD plates containing 200 ug/mL zeocin and grew up after 2 days at 30° C. For the *K. marxianus* transformed cultures, only one transformant of pNC003 and one of pNC 103 were obtained. In *K. lactis* transformed cultures, multiple transformants of each plasmid were obtained.

Transformants were then analyzed for their ability to produce L-lactic acid. Cultures (2 mL) of YPD broth containing 20 g/L glucose and 300 ug/mL zeocin were inoculated directly from colonies on the transformation plates. The cultures were incubated without shaking for 52 hours at 30° C. At the end of that period, the cells were removed by centrifugation and the culture supernatant was assayed for glucose and L-lactic acid using a YSI. The results of these assays are shown in Table 5 below. Both *K. marxianus* and *K. lactis* cells containing the *K. thermotolerans* LDH plasmid were able to produce L-lactic acid to significant levels, whereas the control cells containing the empty vector produced no detectable L-lactic acid. Thus, *K. thermotolerans* LDH is clearly able to functions in other species of yeast to channel carbon into the production of lactic acid.

TABLE 5

| Host | Plasmid | Transformant# | Glucose g/l | L-lactic acid g/l |
|---|---|---|---|---|
| K. lactis | pNC003 | 1 | 10.0 | 0.01 |
| K. lactis | pNC003 | 2 | 9.9 | 0.02 |
| K. lactis | pNC102 | 1 | 10.1 | 2.4 |
| K. lactis | pNC102 | 2 | 10.5 | 2.4 |
| K. lactis | pNC102 | 3 | 10.0 | 2.5 |
| K. lactis | pNC102 | 4 | 10.1 | 2.4 |
| K. lactis | pNC102 | 5 | 10.6 | 2.4 |
| K. lactis | pNC103 | 1 | 11.0 | 2.2 |
| K. lactis | pNC103 | 2 | 10.0 | 2.4 |
| K. lactis | pNC103 | 3 | 9.3 | 2.5 |
| K. lactis | pNC103 | 4 | 11.0 | 2.4 |
| K. lactis | pNC103 | 5 | 9.9 | 2.5 |
| K. marxianus | pNC003 | 1 | 0.01 | 0.02 |
| K. marxianus | pNC103 | 1 | 0.00 | 1.3 |
| YPD only | | | 19.0 | 0.02 |

Example 21

Lactic Acid Production from D-xylose in *Kluyveromyces marxianus*

In order to demonstrate that sugars other than glucose could be used to produce lactic acid, xylose fermentation to lactic acid was conducted in 250-mL baffled shake flasks by genetically engineered strains of *Kluyveromyces marxianus* derived from *K. marxianus* 1 (ATCC Accession No. 52486). More specifically, the three strains used in this example are as follows: (i) NC39: *K. marxianus* 1 carrying the multi-copy plasmid pNC7 that contains the Zeocin selection marker on plasmid pNC3 and the *Bacillus megaterium* lactate dehydrogenate (LDH) under control of a phosphoglycerate kinase promoter as described below; (ii) NC103: *K. marxianus* 1 carrying the multi-copy plasmid pNC103 containing Zeocin selection marker on plasmid pNC003 and the *Kluyveromyces thermotolerans* LDH under control of a phosphoglycerate promoter as described above; and (iii) NC102: *K. marxianus* 1 carrying the multi-copy plasmid pNC102 containing the Zeocin marker on a pKD1 vector. The latter strain was used as the control. Presence of Zeocin in the media minimized plasmid loss.

The innoculum was prepared by transferring a single colony into a 10 mL tube that contained 3 mL of defined complete medium supplemented with 300 μg/mL Zeocin. The medium used in all experiments contained (per liter): 6.7 g Yeast-Nitrogen-Base (YNB; without amino acids and ammonium sulfate), 3 g urea and 0.3 g Zeocin. As a carbon and energy source either 20 g/L D-glucose or D-Xylose were added. The initial pH was adjusted to 5.0 with potassium hydroxide. Cells were grown overnight on a rotary shaker at 250 rpm and 30° C. and then transferred to a 250 mL baffled shake-flask containing 100 mL of the above described YNB media. Cells were again grown overnight at pH 5.0 and 30° C. and subsequently stored in suspension in 15% (w/v) glycerol at −80° C. These stock cultures were used as an inoculum for the experiments described below.

Lactic Acid Production on Glucose with NC39 and NC103

Cultures of strain NC102 NC 103 and NC39 were grown to stationary phase on 2% (w/v) glucose in the above-described YNB media at 250 rpm and 30° C. After this, cells were pelleted and transferred to YNB media supplemented with 2% (w/v) glucose at an initial $OD_{600}$ of 20. The cells were incubated at 100 rpm and 30° C. to reduce oxygen supply to the culture. Liquid samples were withdrawn from the culture at time intervals to measure growth (using $OD_{600}$), metabolites and pH. Metabolite analysis was performed by HPLC using an Aminex HPX-87H column (operating at 55° C. with 10 mM $H_2SO_4$ as the mobile phase at a flow rate of 0.5 mL/min) hooked up to a Waters 410 Refractive Index detector. When the pH dropped below 3.5, 2 g of sterile $CaCO_3$ was added to increase the pH to about 5.5.

Twenty-four hours after the transfer of cells to fresh medium, the glucose was fully depleted in all strains studied. In strains NC39 and NC103, 6.4 g/L (32% yield) and 3.8 g/L (19% yield) lactic acid had been produced, respectively. No lactic acid production could be detected in the control strain NC102. Strain NC 39 and NC103 also produced 2.3 and 2.9 g/L of ethanol, respectively; the control strain NC102 produced 5.8 g/L of ethanol. No other typical fermentation products (pyruvate, succinic acid, glycerol and acetate) could be detected>1.0 g/L in all cultures.

These results established that *Kluyveromyces marxianus* (a crabtree-negative yeast strain) expressing a heterologous LDH (either from *B. megaterium* or *K. thermotolerans*) could be used to produce lactic acid from glucose.

Lactic Acid Production on xylose from NC39 and NC 103.

Lactic acid production using xylose as a carbon source was demonstrated using culture and fermentation conditions substantially as set forth above, except that glucose in the culture media was replaced by D-xylose. A maximum of 4.8 g lactic acid was produced from 20 g xylose (i.e., a yield of 0.23 g/g) in strain NC39 after 72 hours fermentation. No lactic acid was produced in strain NC103 or control strain NC102. In addition, no other fermentation products (such as pyruvate, acetate, glycerol, ethanol) could be detected at >1.0 g/L.

These results established that *Kluyveromyces marxianus* (a crabtree-negative yeast strain) expressing a heterologous LDH (either from *B. megaterium* or *K. thermotolerans*) could be used to produce lactic acid from xylose, albeit at a slower rate than with glucose.

Figure 15:
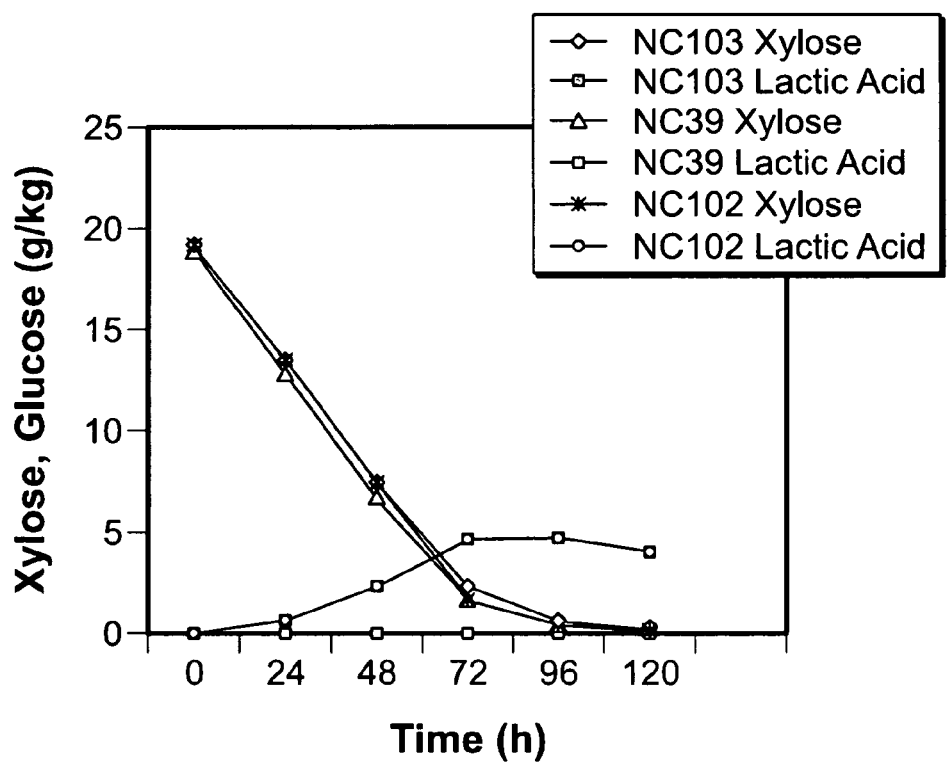
FIG. 15 is a graph showing production of lactic acid by yeast containing the NC39 construct of the invention.

These results are also shown in FIG. 15.

Example 22

L-Lactic Acid Production from Pentose Sugars in Yeasts

Figure 16:
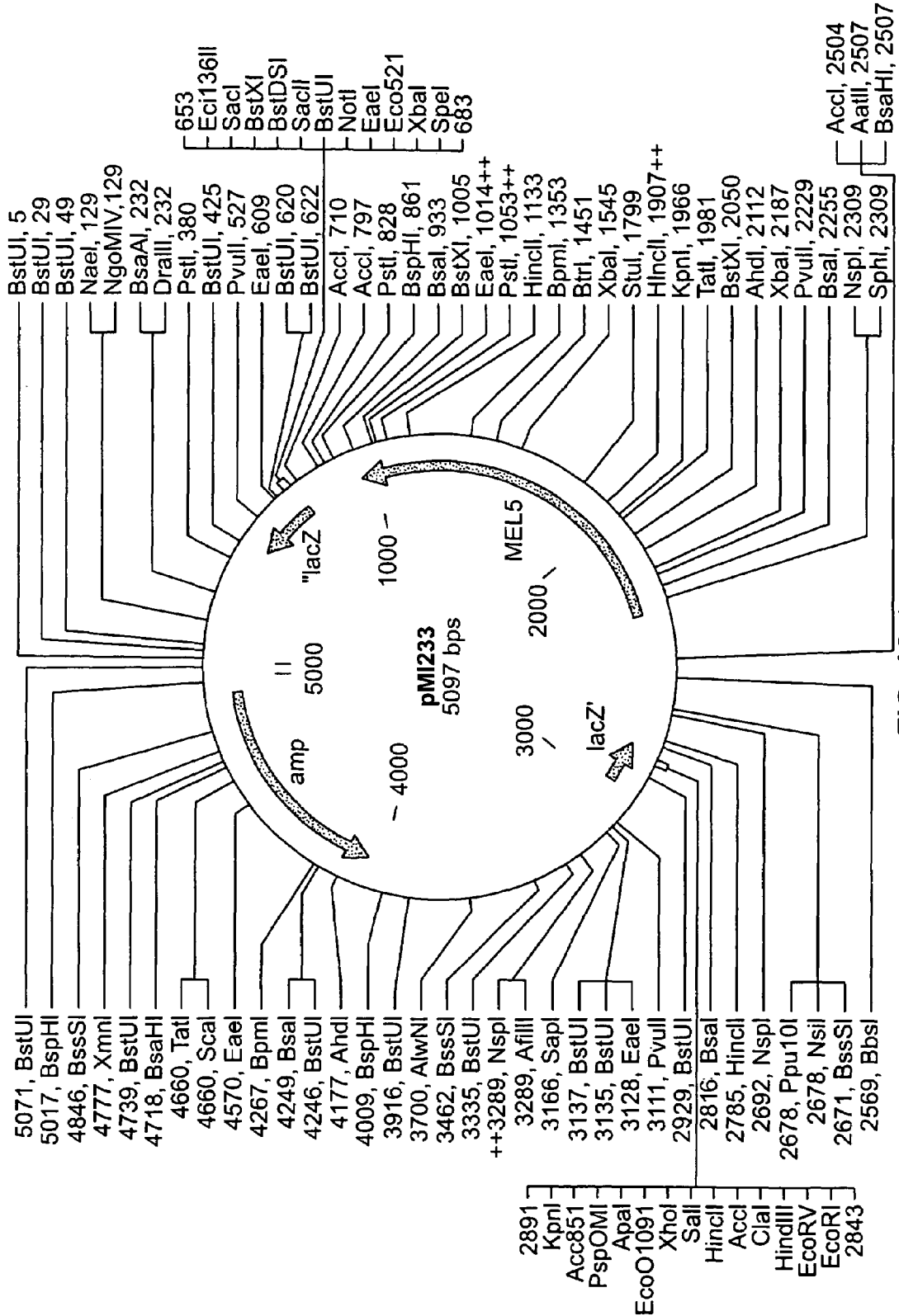
FIG. 16 is a diagram of recombinant expression constructs pMI233, pMI234, pMI238, pvr1, pMI214, pMI227, pMI248, pMI247, pMI207, pMI205 and pMI-203.
Figure 16B:
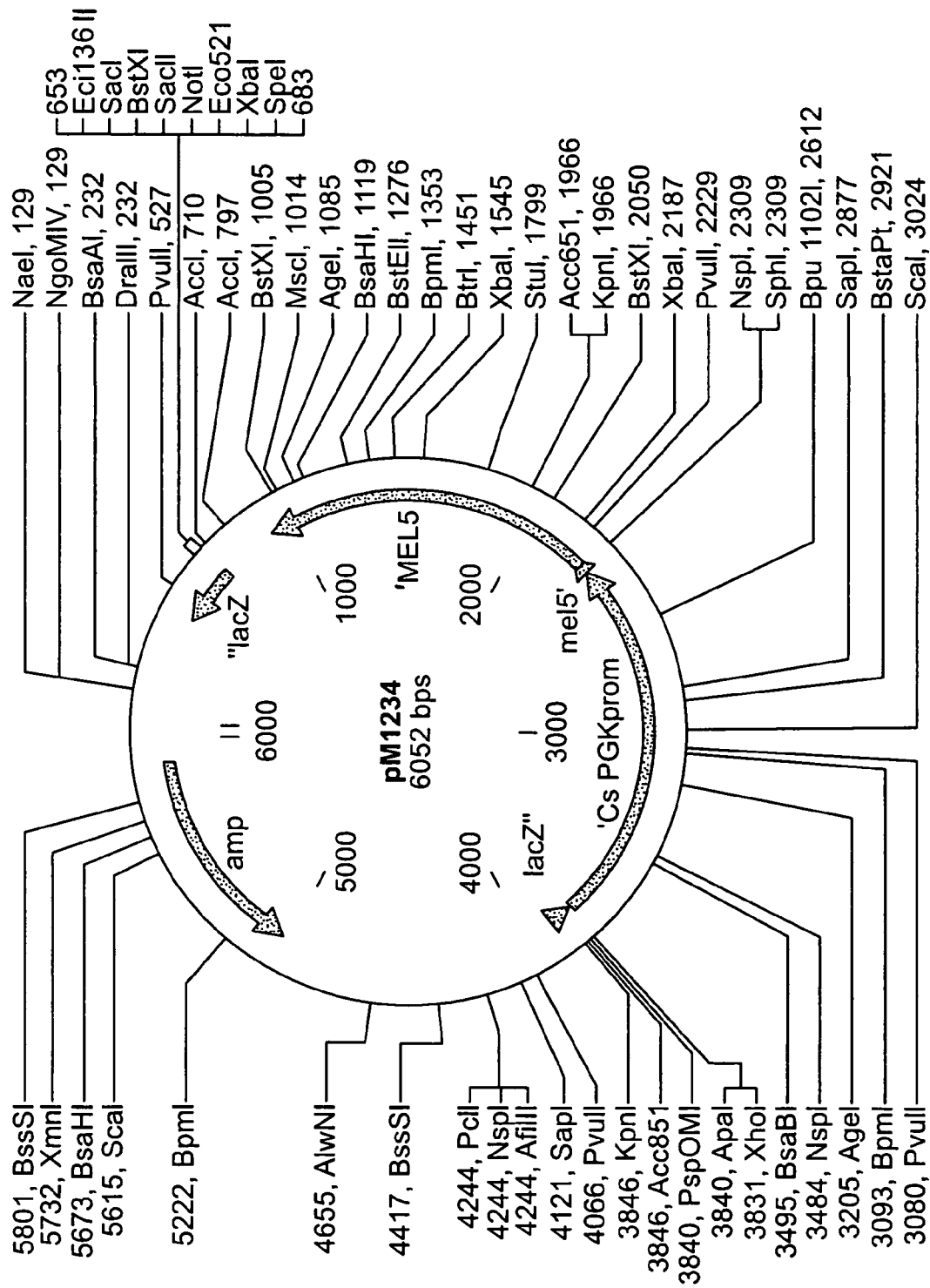
Figure 16:
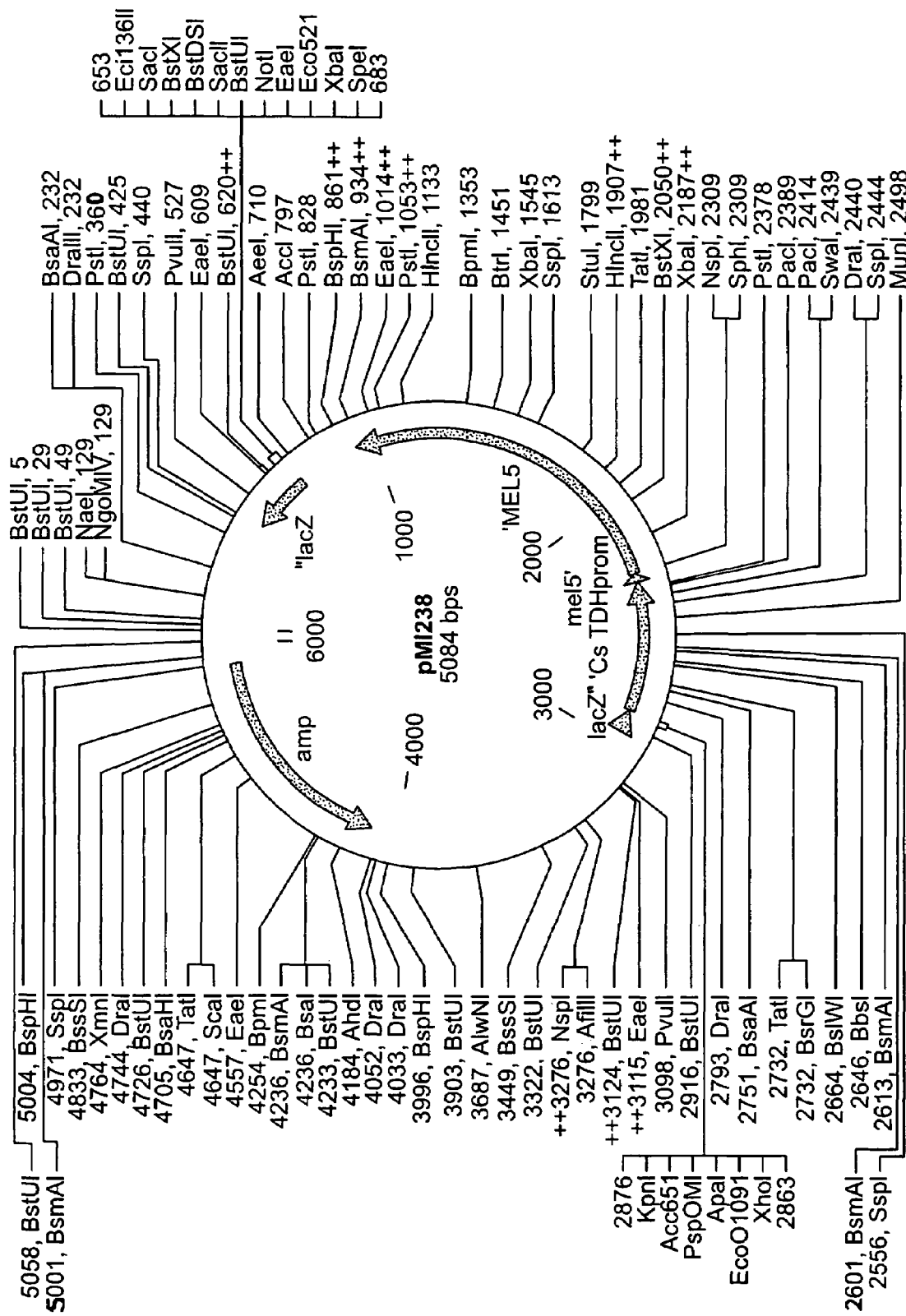
Figure 16:
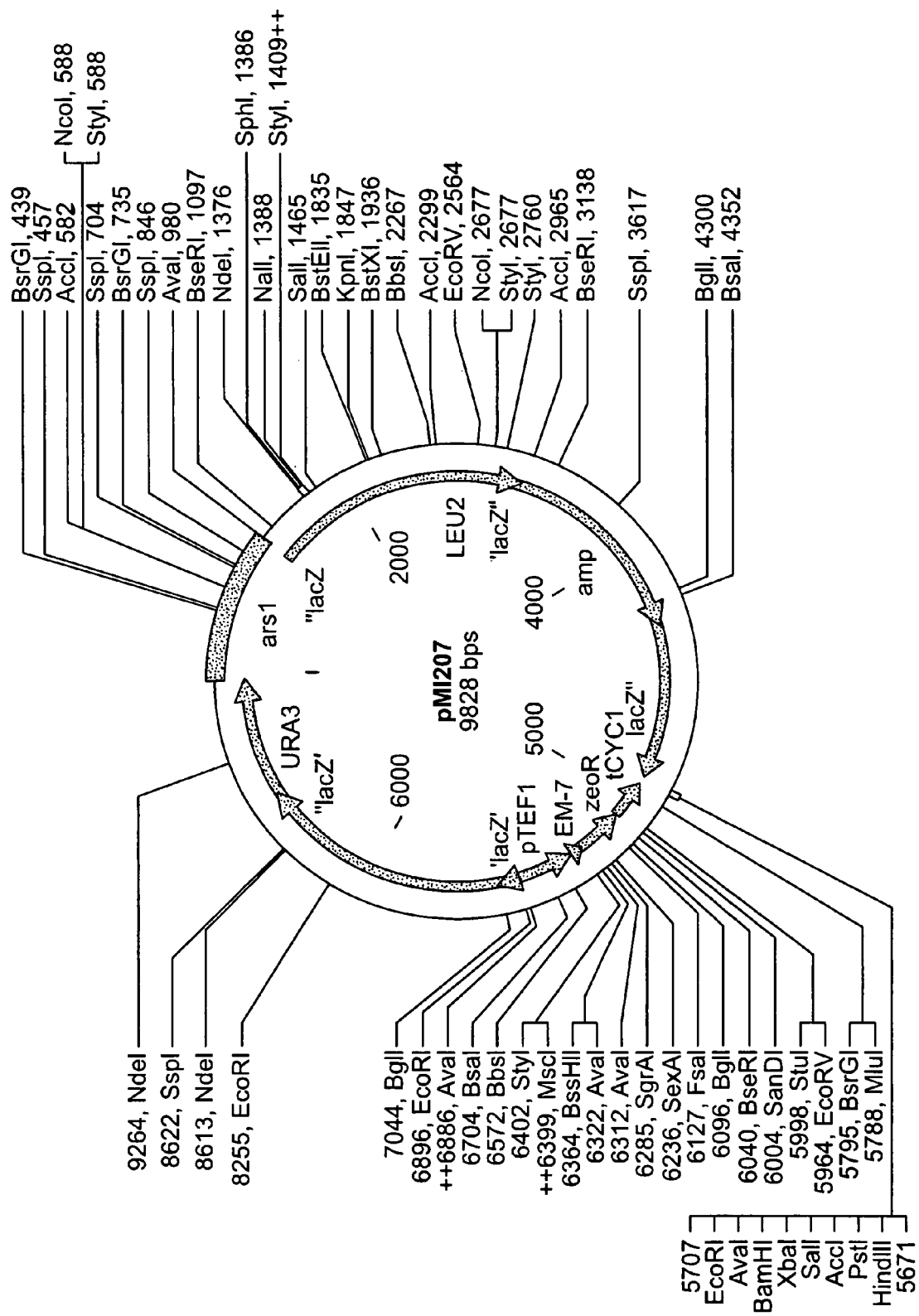
Figure 16:
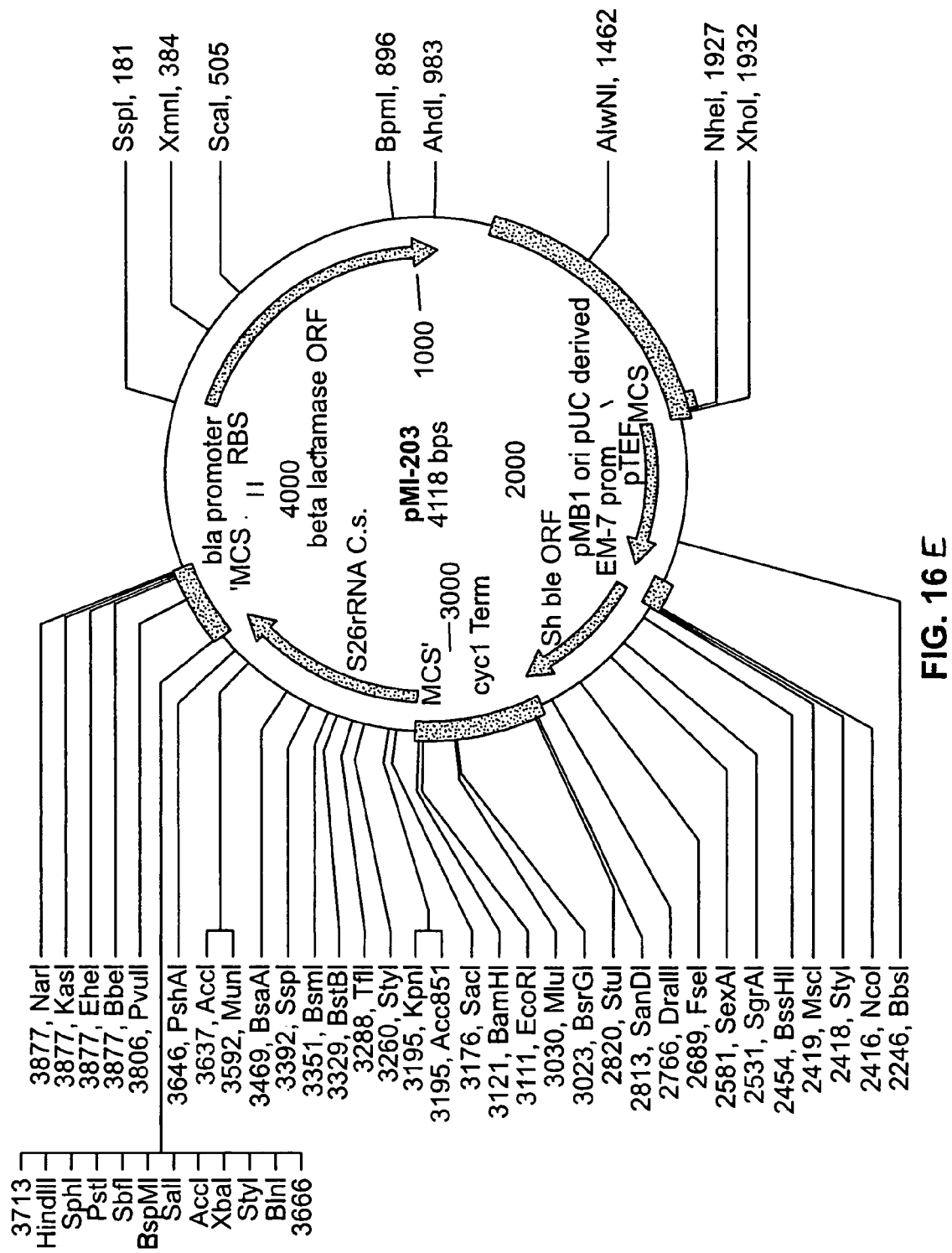
Figure 16:
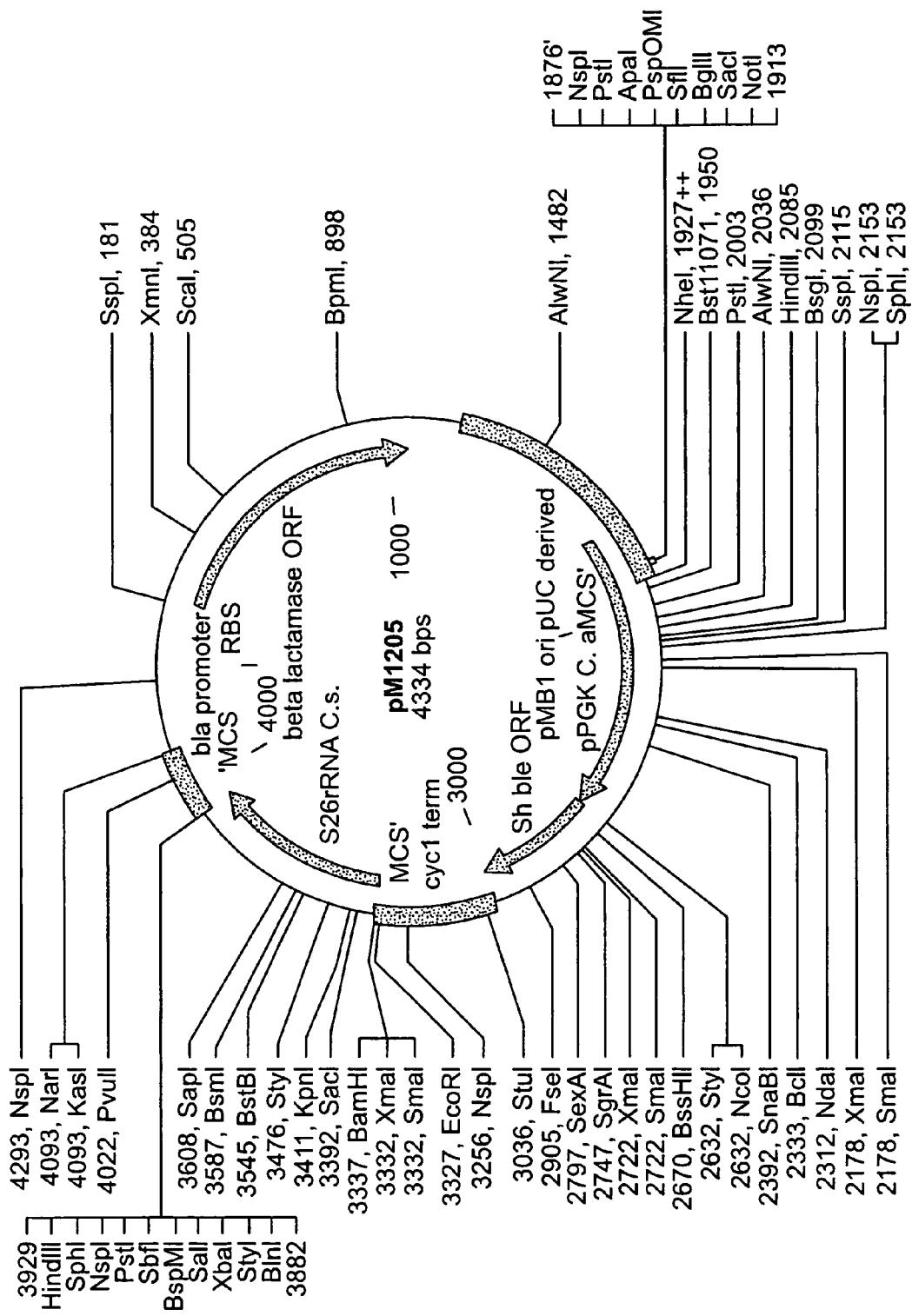
Figure 16:
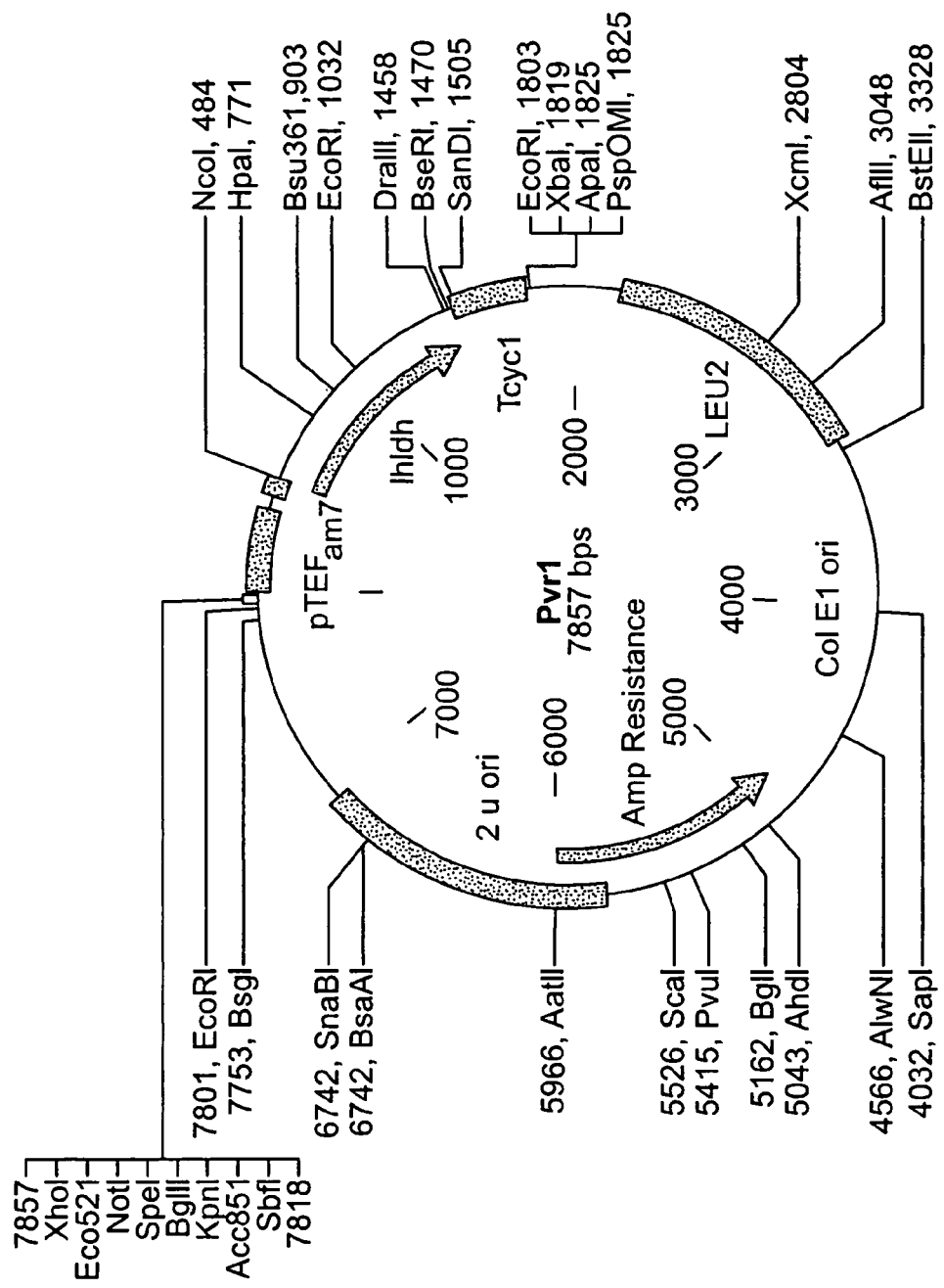
Figure 16:
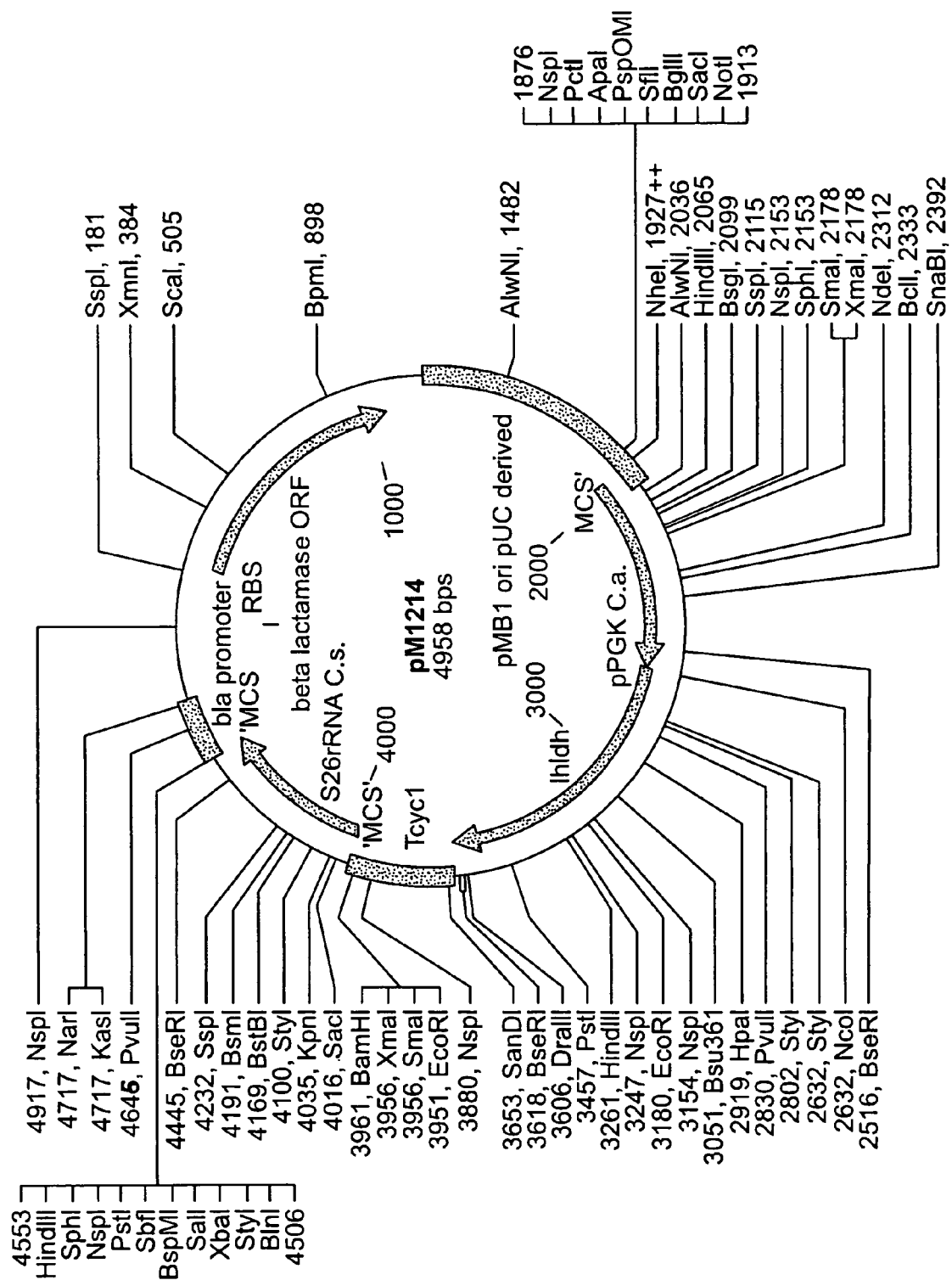
Figure 16:
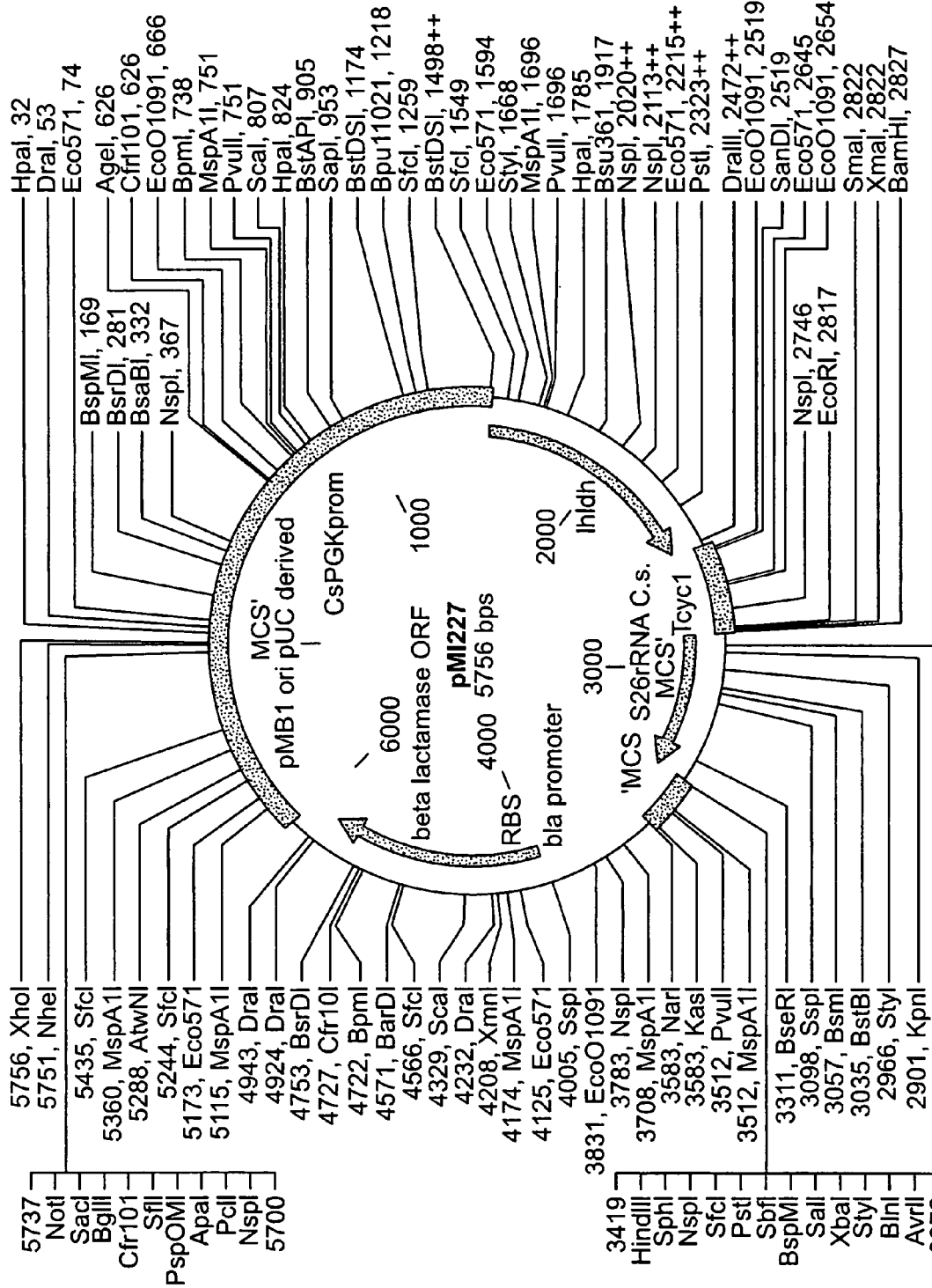
Figure 16:
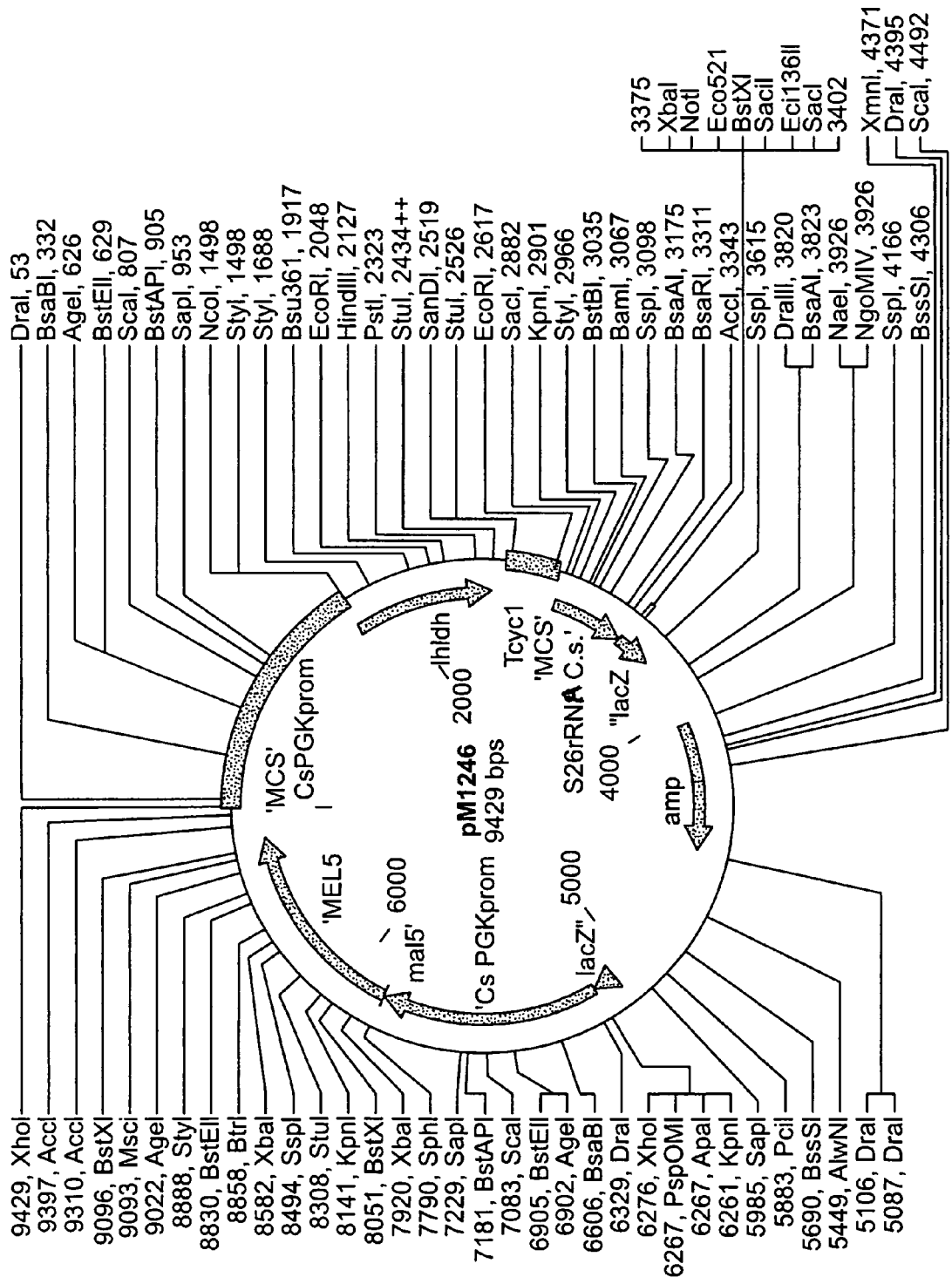
Figure 16:
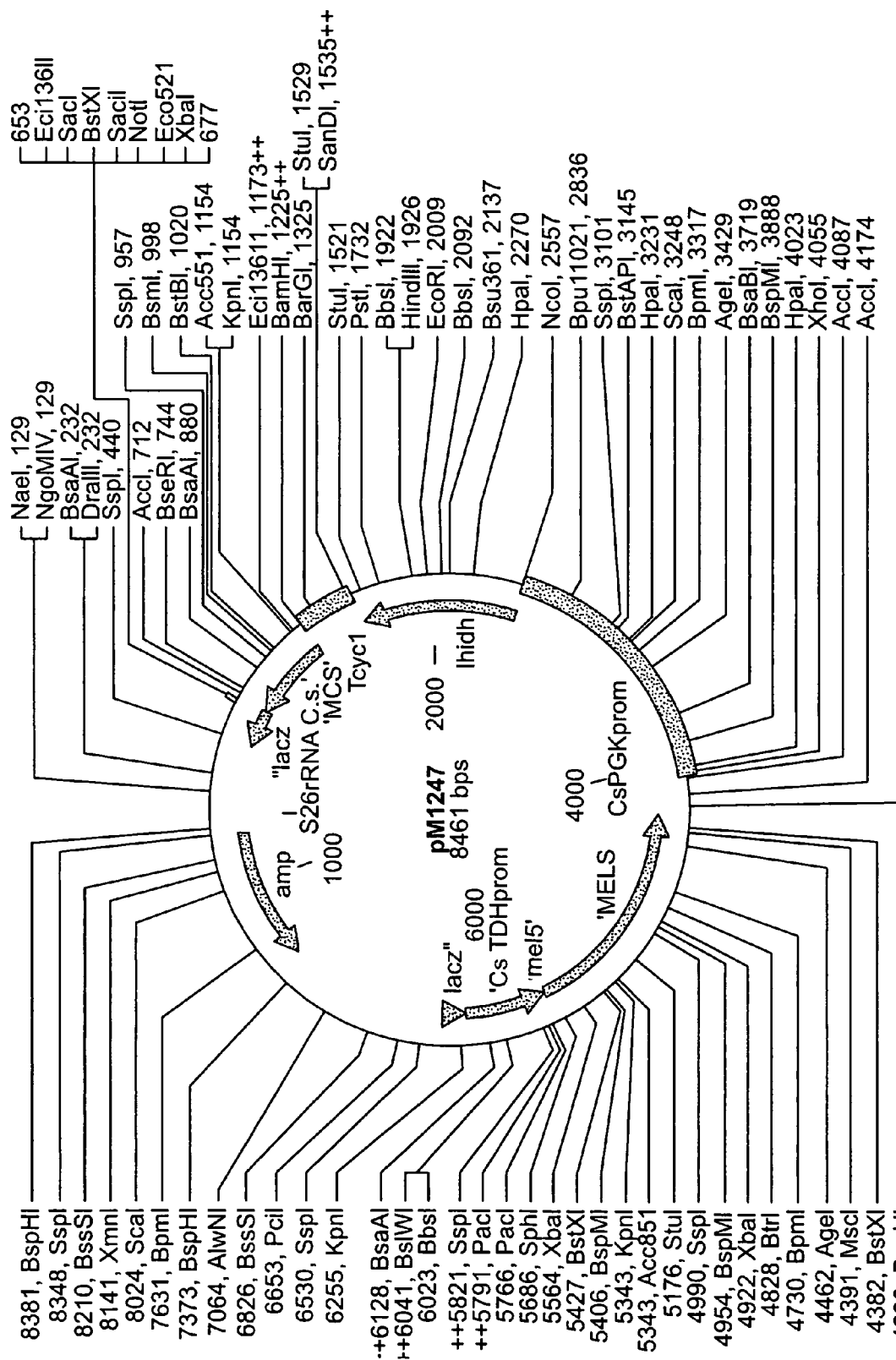

*Candida* species were genetically engineered to use pentose sugars to produce lactic acid. Vectors and other constructs are shown in FIG. 16.

Zeocin Resistance Vectors for *C. sonorensis*

The plasmid pTEF1/Zeo (Invitrogen) containing the zeocin resistance marker under control of *S. cerevisiae* TEF1 promoter was modified by adding a *C. sonorensis* rDNA fragment to provide a target for homologous recombination. The following oligonucleotide primers:

```
                                      (SEQ ID No. 44)
TGG ACT AGT AAA CCA ACA GGG ATT GCG TTA GT
and
                                      (SEQ ID No. 45)
GTA GTC TAG AGA TCA TTA CGC CAG CAT CCT AGG,
``` which correspond to *C. sonorensis* 26 S rRNA (Genbank Accession No. U70185), were used to amplify *C. sonorensis* genomic DNA to provide a PCR-amplified fragment of the 26S rDNA gene. The resulting PCR product fragment was digested with restriction enzymes SpeI and XbaI and ligated with pTEF/Zseo plasmid digested with XbaI. The resulting plasmid, pMI203, is shown in FIG. 16.

The TEF1 promoter contained in pMI203 was replaced by a promoter of a gene from another *Candida* species, the *C. albicans* PGK1 promoter. The following oligonucleotide primers:

(SEQ ID No. 46)
GCG AT<u>C TCG AGG</u> TCC TAG AAT ATG TAT ACT AAT TTG C
and (SEQ ID No. 47)
ACT TGG <u>CCA TGG</u> TGA TAG TTA TTC TTC TGC AAT TGA were designed based on the available *C. albicans* PGK1 sequence (Genbank Accession No. U25180) were used to amplify a 700 bp fragment from the region upstream of the *C. albicans* PGK1 open reading frame, using *C. albicans* genomic DNA as the template. Restriction sites XbaI and SpeI (underlined above) were added to the primers to facilitate cloning of the fragment. After amplification, the fragment was isolated and digested with restriction enzymes XhoI and NcoI and then ligated to plasmid pMI203 digested with XhoI and NcoI. The resulting plasmid, pMI205, is shown in FIG. 16.

Isolation of *C. sonorensis* Genes

In order to develop appropriate genetic tools for *C. sonorensis*, a genomic library was constructed from this species. Genes of interest were isolated from the library on the basis of known amino acid and nucleotide sequences of genes from related yeasts. Promoters and terminators of strong constitutively expressed genes such as PGK1 and TDH1 were isolated and used to express heterologous genes. The PDC genes were isolated because the corresponding enzymes carry out reactions that compete with lactic acid production. Therefore it is desirable to delete the PDC genes from the strains that will be used for lactic acid production.

Genomic DNA of *C. sonorensis* (ATCC Accession No. 32109) was isolated from cells grown overnight in YPD using the Easy DNA kit (Invitrogen). DNA was partially digested with Sau3A and size fractionated by sucrose gradient centrifugation (Sambrook et al. 1989, Molecular Cloning, 2$^{nd}$ ed., Cold Spring Harbor Laboratory, N.Y.), and DNA fragments of about 22 kb were ligated to BamHI digested, phosphatase treated lambda DASH™ vector arms (Stratagene) and the ligation mixture was packaged into lambda particles using Gigapack II Gold Packaging Extract (Stratagene). The lambda particles were used to infect *E. coli* MRA P2.

The probes used for isolation of *C. sonorensis* genes from the library were prepared by PCR amplification using the Dynazyme EXT polymerase (Finnzymes, Espoo, Finland), sequence specific primers and genomic DNA of *S. cerevisiae*, *C. albicans* or *C. sonorensis* as a template as follows:.

Oligonucleotides TGT CAT CAC TGC TCC ATC TT (SEQ ID No.48) and TTA AGC CTT GGC AAC ATA TT (SEQ ID No. 49) corresponding to the *S. cerevisiae* TDH1 gene were used to amplify a fragment of the TDH gene from genomic *S. cerevisiae* DNA.

Oligonucleotides GCG AT<u>CTCGAGG</u> TCC TAG AAT ATG TAT ACT AAT TTG C (SEQ ID No. 50) and CGC GAA TTC <u>CCATGG</u> TTA GTT TTT GTT GGA AAG AGC AAC (SEQ ID No.51) corresponding to the *C. albicans* PGK1 gene were used to amplify a fragment of the PGK1 gene from genomic *C. albicans* DNA.

Oligonucleotides TGG <u>ACTAGT</u> AAA CCA ACA GGG ATT GCC TTA GT (SEQ ID No. 52) and CTA G <u>TCTAGA</u> GA TCA TTA CGC CAG CAT CCT AGG (SEQ ID No. 53) corresponding to the *C. sonorensis* 26 S rRNA were used to amplify a fragment of the 26S rDNA gene from *C. sonorensis* genomic DNA.

Oligonucleotides CCG <u>GAATTCGATATC</u> TGG GCW GGK AAT GCC AAY GAR TTR AAT GC (SEQ ID No. 54) and CGC <u>GGATTCAGGCCT</u> CAG TAN GAR AAW GAA CCN GTR TTR AAR TC (SEQ ID No.55) were designed based on portions of pyruvate decarboxylase amino acid sequence WAGNANELNA (SEQ ID No. 56) and DFNTGSFSYS (SEQ ID No. 57), that are conserved between *S. cerevisiae* PDC 1, *Pichia stipitis* PDC 1 and PDC2, and incomplete sequences of *Candida albicans* PDC1 and PDC3. These primers were used were used to amplify a fragment of the PDC gene(s) from *C. sonorensis* genomic DNA. PCR reaction with these primers produced two fragments of different nucleotide sequence termed PDC 1 and PDC2.

Oligonucleotides TCTGTTMCCTACRTAAGA (SEQ ID No. 58) and GTYGGTGGTCACGAAGGTGC (SEQ ID No. 59) were designed based on conserved regions found in fungal alcohol dehydrogenase sequences. These primers were used to amplify a fragment of the ADH gene(s) from *C. sonorensis* genomic DNA. PCR reaction with these primers produced three fragments of different nucleotide sequences termed ADH1, ADH2, and ADH3.

The library was screened with PCR fragments produced as described above, and products were labeled with $^{32}$P α-dCTP using the Random Primed Labeling Kit (Boehringer Mannheim). Hybridization with the radioactive probes was performed by incubation overnight at 42° C. in a solution containing 50% formamide, 5× Denhardt's, 5×SSPE, 0.1% SDS, 100 µg/mL herring sperm DNA, 1 µg/mL polyA DNA. For TDH1, PGK1, and PDC1 probes, filters were washed after hybridization at room temperature in a solution of 2×SSC for 5 min and repeated, followed by two 30 min washes in a solution of 1×SSC–0.1% SDS at 68° C. The post hybridization washes for rDNA and PDC2 probes were performed twice for 5 min at room temperature in 2×SSC, followed by two 30 min. washes in 0.1×SSC–0.1% SDS at 68° C.

Positive plaques were isolated and purified according to manufacturers instructions (Stratagene). Bacteriophages were purified using conventional methods (Sambrook et al., ibid.), modified by eliminating DNAseI treatment and precipitating phage particles released from lysed host cells using PEG6000, which phage particles were then dissolved in SM buffer and extracted with chloroform, pelleted by centrifugation at 25,000 rpm in Kontron TST41.14 rotor for 2 h, and again dissolved in SM buffer. Lambda DNA was isolated by digesting the phage particles with proteinase K followed by phenol extraction and ethanol precipitation.

The *C. sonorensis* genomic DNA inserts were partially sequenced using sequence-specific primers. The nucleotide sequences and the amino acid sequences deduced therefrom were compared against sequence data bases in order to identify genes encoded in whole or part by the phage insert by homology to known genes or proteins. The sequences obtained had significant similarity to fungal rDNA, phosphoglycerate kinases, glyceraldehyde-3-phosphate dehydrogenases, or pyruvate decarboxylases depending on the probe used for isolating each clone. The start and end points of the open reading frames encoding sequences of *C. sonorensis* PGK1, PDC1 and TDH1 were identified thereby.

Use of MEL5 Gene Selection for Selecting *C. sonorensis* Transformants

In order to develop a positive selection for *C. sonorensis* transformants, the *S. cerevisiae* MEL5 gene (Naumov et al., 1990, *MGG* 224:119–128; Turakainen et al., 1994, *Yeast* 10: 1559–1568; Genbank Accession No. Z37511) was obtained as the 2160 bp EcoRI-SpeI fragment from plasmid pMEL5-39 and ligated to pBluescript II KS(−) (Stratagene) digested with EcoRI and SpeI cut. The EcoRI site in the MEL5 gene is located 510 bp upstream of the initiator ATG, and the SpeI site is located 250 bp downstream of the stop codon of MEL5. The resulting plasmid was designated pMI233, and is shown in FIG. 16.

The 1500 bp PGK1 promoter of *C. sonorensis* was amplified with primers GCG ATCTCGAGA AAG AAA CGA CCC ATC CAA GTG ATG (SEQ ID No. 60) and TGG ACTAGT ACA TGCATGCGG TGA GAA AGT AGA AAG CAA ACA TTG TAT ATA GTC TTT TCT ATT ATT AG (SEQ ID No. 61) using DNA from the PGK1 lambda clone isolated above as template. The 3' primer (SEQ ID No. 61) can create a fusion between the *C. sonorensis* PGK1 promoter and *S. cerevisiae* MEL5, since it corresponds to nucleotides present in the PGK1 promoter immediately upstream of the open reading frame and nucleotides corresponding to the 5' end of MEL5 open reading frame. The resulting amplified fragment was digested with restriction enzymes SphI and XhoI and ligated to plasmid pMI233 digested with SphI and XhoI. The resulting construct in the plasmid contains *C. sonorensis* PGK1 promoter upstream of and operatively linked to the MEL5 open reading frame, and is identified as pMI234 in FIG. 16.

In a similar fashion, a 650 bp of the *C. sonorensis* TDH1 promoter was amplified with primers GCG ATCTCGAGA AAA TGT TAT TAT AAC ACT ACA C (SEQ ID No. 62) and TGG ACTAGT ACA TGCATGCGG TGA GAA AGT AGA AAG CAA ACA TTT TGT TTG ATT TGT TTG TTT TGT TTT TGT TTG (SEQ ID No. 63) using DNA from the TDH1 lambda clone isolated above as the template. The 3' primer (SEQ ID No. 63) can create a fusion between *C. sonorensis* TDH1 promoter and *S. cerevisiae* MEL5, since it corresponds to nucleotides present in the TDH1 promoter immediately upstream of the open reading frame and nucleotides corresponding to the 5' end of MEL5 open reading frame. The amplified fragment was cut with SphI and XhoI and ligated to plasmid pMI233 digested with SphI and XhoI. The resulting plasmid, identified as pMI238 in FIG. 16, contains *C. sonorensis* TDH1 promoter upstream of and operatively linked to the MEL5 open reading frame.

The MEL5 expression cassette was released from vector sequences by restriction enzyme digestion with SpeI and XhoI, and 1 μg of the linear DNA was transformed into *C. sonorensis* by electroporation according to the method of Backer et al. (1999, *Yeast* 15: 1609–1618). Cells were transformed after growth overnight in 50 mL of YPD, harvesting by centrifugation and after being resuspended in a solution of 0.1 M LiAc/10 mM DTT/10 mM Tris-HCl and incubated at room temperature for 1 h. The cells were collected by centrifugation and washed with cold water and IM sorbitol and resuspended in cold 1M sorbitol. DNA (1–3 μg) was added into 40 μL of cell suspension and the mixture was pipetted into a 0.2 cm electroporation cuvette. The Bio-Rad Gene Pulser was used at settings of 1.5 kV, 25 F, 200 Ω for electroporation. After the electric pulse 1 mL of cold 1M sorbitol was added onto the cells. The cells were then incubated at 30° C. without shaking for 1 h; alternatively, 2 mL YPD was added and the incubation was continued at 30° C. for 2–3 h. The cells were plated onto appropriate agar plates for regeneration.

In additional alternatives, the cells were transformed according to the protocol of Gietz et al. (1992, *Nucleic Acids Res.* 20:1425). Transformants were grown on YPD agar plates (comprising 10 g/L yeast extract, 20 g/L peptone 20 g/l, 20 g/L glucose and 2% agar) supplemented with the chromogenic substrate of α-galactosidase, 5-bromo-4-chloro-3-indolyl-α-D-galactopyranoside (X-gal; ICN Biochemicals) at a concentration of 40 μg/mL. The plates were incubated at 30° C. for 1–3 days and then transferred to 4° C. In the presence of X-gal yeast colonies transformed with a functional MEL5 expression cassette turned blue, whereas the untransformed colonies were white. The transformation frequency obtained in these experiments was 2–20 transformants/μg DNA. Blue colonies were purified by restreaking them onto fresh indicator plates.

The transformants also acquired the ability to grow on melibiose as the sole carbon source. This indicates that melibiose was hydrolysed into glucose and galactose by the MEL5-encoded α-galactosidase that was secreted into the medium.

A parallel strategy to screening the transformants on X-gal containing medium is selecting them on a medium containing melibiose as the sole carbon source. After transformation the cells are spread onto agar plates containing 0.67% Yeast Nitrogen base (Difco) and 2% melibiose and the plates are incubated at 30° C. for 5–10 days. Under these conditions the untransformed cells are unable to grow to a visible colony whereas the MEL5 transformants form colonies.

*L. helveticus* LDH Expression Cassette and Vector Containing the MEL5 Marker for *C. sonorensis*

Plasmid pMI205 was used to produce a plasmid containing the MEL5 gene as a selectable marker and the LDH gene for enabling production of lactic acid in *C. soronensis*. In the resulting plasmid, the zeocin resistance gene in pMI205 was replaced by the *L. helveticus* LDH gene.

A 1329 bp NcoI-BamHI fragment of pVR1 containing the LDH gene and the CYC1 terminator was ligated to the 3413 bp NcoI-BamHI fragment of pMI205 bringing the *L. helveticus* LDH gene under control of the *C. albicans* PGK1 promoter; the resulting plasmid was named pMI214 and is shown in FIG. 16. In a second step the *C. albicans* PGK1 promoter was replaced by the *C. sonorensis* PGK1 promoter. The *C. sonorensis* PGK1 promoter was isolated by amplification from an isolated lambda clone as described above using primers GCG ATCTCGAGA AAG AAA CGA CCC ATC CAA GTG ATG (SEQ ID No. 64) and ACT TGG CCATGG TAT ATA GTC TTT TCT ATT ATT AG (SEQ ID No. 65), and the PCR product was digested with XhoI and NeoI and ligated into pMI214 digested with XhoI and NcoI. This plasmid was designated pMI277 and is shown in FIG. 16.

The LDH expression cassette from pMI227 and MEL5 marker cassette from pMI234 were combined into the same vector by ligating a 3377 bp AvrII-NheI fragment of pMI227 with SpeI-digested pMI234. The resulting plasmid was designated pMI246 and is shown in FIG. 16.

The LDH expression cassette from pMI227 and the MEL5 marker cassette from pMI238 were combined into the same vector by ligating a 3377 bp AvrII-NheI fragment of pMI227 with SpeI-digested pMI238. The resulting plasmid was designated pMI247 and is shown in FIG. 16.

Transformation of C. sonorensis for Lactic Acid Production LDH-encoding vectors were introduced into C. sonorensis cells using transformation methods developed in the art for other yeast species. Before transformation, plasmids pMI246 and pMI247 were linearized by restriction enzyme digestion BstBI, an enzyme that cuts within the rDNA sequences, thus targeting integration into the rDNA locus. Alternatively, the transforming plasmids were digested with ApaI and BamHI, followed by purification from agarose gel, thereby releasing the marker and LDH cassettes from vector sequences and facilitating random integration in the genome.

C. sonorensis was transformed with pMI246 or pMI247 by the lithium acetate method (Gietz et al., 1992, Nucleic Acids Res. 20:1425) or by electroporation as described above and transformants were screened and purified based on the blue color formed on YPD plates supplemented with X-gal.

Alpha-galactosidase producing colonies were tested for the production of lactic acid. The transformants were grown in YPD liquid medium overnight at 30° C. and aliquots of the culture medium were withdrawn and analyzed for the presence of lactic acid enzymatically using an L-lactic acid determination kit (Boehringer Mannheim). At least 10 times more lactic acid was detected in culture supernatants of the transformants than those of the host strain.

Transformants originating from transformation of C. sonorensis with BstBI cut pMI246 were designated as 246-1 through 246-9. Transformants originating from transformation of C. sonorensis with BstBI cut pMI247 were designated as 247-1 through 247-4. Transformants originating from transformation of C. sonorensis with ApaI-BamHI cut pMI246 were designated as 246-10 through 246-15. Transformants originating from transformation of C. sonorensis with ApaI-BamHI cut pMI247 were designated as 247-5 through 247-10.

Production of L-lactic Acid in Rich Media by C. sonorensis Harboring the L. helveticus LDH Gene Integrated into the Genome.

C. sonorensis cells and the transformants disclosed above (246-1, 246-2, 246-3, 247-1, 247-2, 247-3 and 247-4) were cultivated in YPD media. Precultures were grown in YPD-medium to an $OD_{600}$ of 11–17, and then resuspended in 50 mL of YPD to an $OD_{600}$ of 0.5 for the cultivation experiments. At the outset of cultivation, yeast cells were cultured in 250 mL Erlenmeyer flasks with 250 rpm shaking. After 4 hours cultivation yeast cells were moved into 100 mL Erlenmeyer flasks and additional glucose (corresponding to a final concentration of 20 g/L) was added and cultivations continued with 40 rpm shaking. Samples were withdrawn during cultivation, $OD_{600}$, measured, and cells harvested by centrifugation and the growth media analyzed by HPLC for lactic acid and glucose (using the L-lactic acid UV method and glucose/GOD-Periodate method of Boehringer Mannheim).

After 24 hours of cultivation transformants produced 2.4–3.3 g/L lactic acid (equivalent to 11–63% yield) from glucose, whereas control strain produced 0.05 g/L lactic acid (a 0.1% yield).

This example demonstrated that overexpression of LDH in C. sonorensis cells enhanced L-lactic acid production on glucose-containing media.

Production of L-lactic Acid in Minimal Glucose Media by C. sonorensis Harboring the L. helveticus LDH Gene Integrated into the Genome.

C. sonorensis cells and the transformants disclosed above (246-1, 246-3, 247-2) were cultivated in were cultivated in YD medium (yeast nitrogen base without amino acids supplemented-with 2% glucose). Precultures were grown in YD medium to an $OD_{600}$ of 10–13, cells collected by centrifugation, washed once with YD medium and then resuspended in 50 mL of YD to an $OD_{600}$ of 0.4 for the cultivation experiments. Yeast were cultivated in 100 mL Erlenmeyer flasks with 40 rpm shaking (microaerobic conditions). Samples were withdrawn during cultivation, $OD_{600}$ measured, and cells harvested by centrifugation and the growth media analyzed by HPLC for lactic acid and glucose. HPLC analyses were carried out with a Waters 510 HPLC pump, Waters 717+ autosampler and Water System Interphase Module liquid chromatography complex with refractive index detector (Waters 410 Differential refractometer) and UV-detector (Waters 2487 dual λ UV detector). An Aminex HPX-87H Ion Exclusion Column (300 mm×7.8 mm, Bio-Rad) used was equilibrated with 5 mM $H_2SO_4$ in water at 35° C. and samples were eluted with 5 mM $H_2SO_4$ in water at a flow rate of 0.6 mL/min. Data acquisition and control was done with Waters Millennium software.

After 70 hours cultivation the transformants produced 2.2–2.5 g/L lactic acid (equivalent to 10–13% yield) from glucose, whereas the control strain did not produce detectable lactic acid.

This example demonstrated that C. sonorensis cells overexpressing a heterologous LDH gene was capable of producing lactic acid from glucose.

Production of L-lactic Acid in Minimal Glucose Media under Anaerobic Conditions by C. sonorensis Cells Harboring the L. helveticus LDH Gene Integrated into the Genome.

C. sonorensis cells and the transformant disclosed above (246-1) were cultivated in were cultivated in YD medium (yeast nitrogen base without amino acids supplemented with 2% glucose) in anaerobic shake flasks. Precultures were grown in YD medium to an $OD_{600}$ of 22–24, cells collected by centrifugation, washed once with YD medium and then resuspended in 100 mL of YD to an $OD_{600}$ of 0.75 for the cultivation experiments. Yeast were cultivated in 100 mL Erlenmeyer flasks equipped with waterlocks with 40 rpm shaking (anaerobic conditions). Samples were withdrawn during cultivation, $OD_{600}$ measured, and cells harvested by centrifugation and the growth media analyzed by HPLC for lactic acid and glucose. HPLC analyses were carried out with a Waters 510 HPLC pump, Waters 717+ autosampler and Water System Interphase Module liquid chromatography complex with refractive index detector (Waters 410 Differential refractometer) and UV-detector (Waters 2487 dual λ UV detector). An Aminex HPX-87H Ion Exclusion Column (300 mm×7.8 mm, Bio-Rad) used was equilibrated with 5 mM $H_2SO_4$ in water at 35° C. and samples were eluted with 5 mM $H_2SO_4$ in water at a flow rate of 0.6 mL/min. Data acquisition and control was done with Waters Millennium software.

After 160 hours of cultivation the strain 246-1 produced 1.1 g/L lactic acid (equivalent to 16% yield) from glucose, whereas the control strain produced lactic acid 0.03 g/L (0.1% yield).

This example demonstrated that C. sonorensis cells overexpressing a heterologous LDH gene was capable of producing lactic acid from glucose under anaerobic conditions.

Production of L-lactic Acid in Minimal Xylose Media by C. sonorensis Harboring the L. helveticus LDH Gene Integrated into the Genome.

C. sonorensis cells and the transformants (246-1, 246-3, 247-2) described above were cultivated in YX-medium (yeast nitrogen base without amino acids and supplemented with 2% xylose). Precultures were grown in YPD-medium to an $OD_{600}$ of 10–13, and thereafter the cells were collected by centrifugation, washed once with YX-medium and resuspended to an $OD_{600}$ of 0.75 in 50 mL of YX-medium for cultivation experiments. Yeast cultures were cultivated in 100 mL Erlenmeyer flasks with 40 rpm shaking. Samples were withdrawn during cultivation, $OD_{600}$ measured, and cells harvested by centrifugation and the growth media analyzed by HPLC for lactic acid and xylose. The HPLC analyses were carried out with a Waters 510 HPLC pump, Waters 717+ autosampler and Water System Interphase Module liquid chromatography complex with refractive index detector (Waters 410 Differential refractometer) and UV-detector (Waters 2487 dual λ UV detector). An Aminex HPX-87H Ion Exclusion Column (300 mm×7.8 mm, Bio-Rad) was equilibrated with 5 mM $H_2SO_4$ in water at 35° C. and samples were eluted with 5 mM $H_2SO_4$ in water at a flow rate of 0.6 mL/min. Data acquisition and control was done with Waters Millennium software. L-lactic acid was analyzed by the L-lactic acid UV method of Boehringer Mannheim.

After 70 hours of cultivation the transformants produced 0.1 g/L lactic acid (equivalent to 9–17% yields) from xylose, whereas the control strain produced lactic acid 0.003 g/L (0.2% yield).

This example demonstrated that *C. sonorensis* overexpressing a heterologous lactate dehydrogenase encoding gene was capable of producing lactic acid from xylose.

Production of L-lactic Acid in Minimal Xylose Media by *C. sonorensis* Harboring the *L. helveticus* LDH Gene Integrated into the Genome.

*C. sonorensis* cells and the transformants (246-1, 246-3, 247-2) described above were cultivated in YX-medium (yeast nitrogen base without amino acids and supplemented with 2% xylose). Precultures were grown in YPD-medium to an $OD_{600}$ of 12–18, and thereafter the cells were collected by centrifugation, washed once with YX-medium and resuspended to an $OD_{600}$ of 2.0 in 50 mL of YX-medium for cultivation experiments. Yeast cultures were cultivated in 100 mL Erlenmeyer flasks with 40 rpm shaking (microaerobic conditions). Samples were withdrawn during cultivation, $OD_{600}$ measured, and cells harvested by centrifugation and the growth media analyzed by HPLC for lactic acid and xylose. The HPLC analyses were carried out with a Waters 510 HPLC pump, Waters 717+ autosampler and Water System Interphase Module liquid chromatography complex with refractive index detector (Waters 410 Differential refractometer) and UV-detector (Waters 2487 dual λ UV detector). An Aminex HPX-87H Ion Exclusion Column (300 mm×7.8 mm, Bio-Rad) was equilibrated with 5 mM $H_2SO_4$ in water at 35° C. and samples were eluted with 5 mM $H_2SO_4$ in water at a flow rate of 0.6 mL/min. Data acquisition and control was done with Waters Millennium software. L-lactic acid was analyzed by the L-lactic acid UV method of Boehringer Mannheim.

After 165 hours of cultivation the transformants produced 0.2 g/L lactic acid (equivalent to 5–6% yield) from xylose, whereas the control strain did not produce detectable lactic acid.

This example demonstrated that *C. sonorensis* overexpressing a heterologous lactate dehydrogenase encoding gene was capable of producing lactic acid from xylose.

Production of L-lactic Acid in Minimal Arabinose Media by *C. sonorensis* Harboring the *L. helveticus* LDH Gene Integrated into the Genome.

*C. sonorensis* cells and the transformants (246-1, 246-3, 247-2) were cultivated in YA-medium (yeast nitrogen base without amino acids and supplemented with 2% L-arabinose). Precultures were grown in YPD-medium to an $OD_{600}$ of 12–18, and thereafter the cells were collected by centrifugation, washed once with YA-medium and resuspended to an $OD_{600}$ of 2.0 in 50 mL of YA-medium for cultivation experiments. Yeast cultures were cultivated in 100 mL Erlenmeyer flasks with 40 rpm shaking (microaerobic conditions). Samples were withdrawn during cultivation, $OD_{600}$ measured, and cells harvested by centrifugation and the growth media analyzed by HPLC for lactic acid and arabinose. The HPLC analyses were carried out with a Waters 510 HPLC pump, Waters 717+ autosampler and Water System Interphase Module liquid chromatography complex with refractive index detector (Waters 410 Differential refractometer) and UV-detector (Waters 2487 dual λ UV detector). An Aminex HPX-87H Ion Exclusion Column (300 mm×7,8 mm, Bio-Rad) used was equilibrated with 5 mM $H_2SO_4$ in water at 35° C., and samples were eluted with 5 mM $H_2SO_4$ in water at a flow rate of 0.6 mL/min. Data acquisition and control were performed with the Waters Millennium software.

After 165 hours of cultivation the transformants produced 0.04–0.05 g/L lactic acid (equivalent to a 2–3% yield) from arabinose, whereas the control strain produced lactic acid 0.007 g/L (a 0.5% yield).

This example demonstrated that *C. sonorensis* overexpressing a heterologous lactate dehydrogenase encoding gene was capable of producing lactic acid from arabinose.

Production of L-lactic Acid in Minimal Melibiose Media by *C. sonorensis* Strain Harboring the *L. helveticus* LDH Gene Integrated into the Genome

*C. sonorensis* cells and the transformants described above (246-1, 246-10, 247-2, 247-5) were cultivated in YM medium (yeast nitrogen base without amino acids supplemented with 2% melibiose). Precultures were grown in YPD medium to an $OD_{600}$ of 18–25, cells were collected by centrifugation and washed once with YM medium and resuspended in 50 mL of YM medium to an $OD_{600}$ of 1.5 for cultivation experiments. Yeast were cultivated in 100 mL Erlenmeyer flasks with 40 rpm shaking (microaerobic conditions). Samples were withdrawn during cultivation, $OD_{600}$ measured, and cells harvested by centrifugation and the growth media analyzed by HPLC for lactic acid (by the L-lactic acid UV method of Boehringer Mannheim).

After 165 hours of cultivation the transformants produced 0.8–2.6 g/L lactic acid.

This example discloses that *C. sonorensis* cells overexpressing a heterologous LDH gene was capable of producing lactic acid from melibiose.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. An isolated nucleic acid encoding a yeast lactate dehydrogenase protein having an amino acid sequence Seq. ID No. 22.

2. An isolated nucleic acid according to claim 1 encoding a yeast lactate dehydrogenate protein that hybridizes to the nucleic acid probe of Seq. ID No. 21 under conditions of a temperature of 42° C. in a solution containing 50% formamide, 5× Denhardt's, 5×SSPE, 0.1% SDS, 100 µg/mL herring sperm DNA, 1 µg/mL polyA DNA, wherein hybridization is detected after washing under conditions of room temperature in a solution of 2×SSC for 5 min and repeated, followed by two 30 minute washes in a solution of 1×SSC −0.1% SDS at 68° C.

3. A recombinant expression construct comprising the nucleic acid having the nucleotide sequence encoding a yeast lactate dehydronase protein according to claim 1, wherein the nucleic acid is expressed in a yeast cell.

4. A recombinant expression construct according to claim 3, further comprising a yeast promoter operably linked to the nucleic acid encoding a yeast lactate dehydronase protein.

5. A recombinant expression construct according to claim 3, further comprising a yeast transcriptional terminator element operably linked to the nucleic acid encoding a yeast lactate dehydronase protein.

6. A recombinant expression construct according to claim 3, further comprising a yeast replication element of a yeast 2-micron circle plasmid.

7. A yeast cell transformed with the recombinant expression construct of claim 3 wherein the transformed cell expresses the yeast lactate dehydrogenate protein.

8. A yeast cell according to claim 7, wherein the yeast cell is a yeast from genera *Saccharomyces, Kluyveromyces, Hansenula, Candida, Trichosporon, Yamadazyma, Torulaspora* or *Pichia*.

9. A yeast cell according to claim 7, wherein the yeast cell expresses a crabtree-negative phenotype.

10. A yeast cell according to claim 7, wherein the yeast cell is a yeast species selected from the group consisting of *C. soronensis* and *K. marxianus*.

11. A yeast cell according to claim 7, wherein the yeast cell produces a glycolytic enzyme selected from the group consisting of pyruvate decarboxylase, alcohol dehydrogenate, and acetyl-CoA synthase in an amount lower than the amount produced in a *C. soronensis* or *K. marxianus* yeast cell.

12. A method for producing lactic acid comprising the step of fermenting the yeast cell culture according to claim 7 in a nutrient medium containing a sugar under conditions whereby at least 50% of the sugar is converted by the yeast cell to lactic acid.

13. The method of claim 12, wherein the yeast cell is grown at a temperature from about 35° C. to about 55° C.

14. The method of claim 12, wherein the nutrient culture has a pH less than about pH 5.0.

15. The method of claim 12, wherein the yeast is grown under substantially anaerobic conditions.

16. The method of claim 12, wherein the yeast cell is a crabtree-negative yeast cell.

17. The method of claim 16, wherein the yeast cell is *K. marxianus* or *C. sonorensis*.

18. The method of claim 12, wherein the yeast cell produces a glycolytic enzyme selected from the group consisting of pyruvate decarboxylase, alcohol dehydrogenate, and acetyl-CoA synthase in an amount lower than the amount produced in a *C. soronensis* or *K. marxianus* yeast cell.

19. The method of claim 12, wherein the sugar is glucose, xylose, ribose, arabinose, mannose, galactose, fructose, maltose or lyxose.

* * * * *

UNITED STATES PATENT AND TRADEMARK OFFICE
CERTIFICATE OF CORRECTION

| | | |
|---|---|---|
| PATENT NO. | : 7,109,010 B2 | Page 1 of 1 |
| APPLICATION NO. | : 09/992430 | |
| DATED | : September 19, 2006 | |
| INVENTOR(S) | : Vineet Rajgarhia et al. | |

It is certified that error appears in the above-identified patent and that said Letters Patent is hereby corrected as shown below:

Column 1, line 6, after priority claim, please add the paragraph -- This invention was made with U.S. Government support under contract No. DE-FC36-00GO10598 awarded by the Department of Energy. The Government has certain rights in this invention. --

Signed and Sealed this

Thirty-first Day of July, 2007

JON W. DUDAS
*Director of the United States Patent and Trademark Office*